(12) United States Patent
Qiu et al.

(10) Patent No.: US 12,098,194 B2
(45) Date of Patent: Sep. 24, 2024

(54) BONE-TARGETING ANTIBODIES

(71) Applicant: Genzyme Corporation, Cambridge, MA (US)

(72) Inventors: Huawei Qiu, Westborough, MA (US); Sunghae Park, Waban, MA (US); James Stefano, Hopkinton, MA (US)

(73) Assignee: Genzyme Corporation, Cambridge, MA (US)

( * ) Notice: Subject to any disclaimer, the term of this patent is extended or adjusted under 35 U.S.C. 154(b) by 343 days.

(21) Appl. No.: 17/079,285

(22) Filed: Oct. 23, 2020

(65) Prior Publication Data
US 2021/0163584 A1  Jun. 3, 2021

Related U.S. Application Data

(62) Division of application No. 15/875,125, filed on Jan. 19, 2018, now Pat. No. 10,844,115.

(60) Provisional application No. 62/448,763, filed on Jan. 20, 2017.

(51) Int. Cl.
| | |
|---|---|
| *A61K 39/395* | (2006.01) |
| *A61K 47/68* | (2017.01) |
| *A61P 13/12* | (2006.01) |
| *A61P 19/08* | (2006.01) |
| *A61P 19/10* | (2006.01) |
| *A61P 35/04* | (2006.01) |
| *C07K 7/06* | (2006.01) |
| *C07K 16/22* | (2006.01) |
| *A61K 39/00* | (2006.01) |

(52) U.S. Cl.
CPC .......... *C07K 16/22* (2013.01); *A61K 39/3955* (2013.01); *A61K 47/68* (2017.08); *A61P 13/12* (2018.01); *A61P 19/08* (2018.01); *A61P 19/10* (2018.01); *A61P 35/04* (2018.01); *C07K 7/06* (2013.01); *A61K 2039/505* (2013.01); *C07K 2317/76* (2013.01); *C07K 2317/92* (2013.01); *C07K 2317/94* (2013.01); *C07K 2319/00* (2013.01)

(58) Field of Classification Search
CPC .. A61K 39/3955; A61K 47/68; A61K 39/395; C07K 16/22
See application file for complete search history.

(56) References Cited

U.S. PATENT DOCUMENTS

| | | |
|---|---|---|
| 4,671,958 A | 6/1987 | Rodwell et al. |
| 4,867,973 A | 9/1989 | Goers et al. |
| 5,571,714 A | 11/1996 | Dasch et al. |
| 5,824,655 A | 10/1998 | Border |
| 6,419,928 B1 | 7/2002 | Dasch et al. |
| 6,455,495 B1 | 9/2002 | Orgel et al. |
| 7,527,791 B2 | 5/2009 | Adams et al. |
| 7,723,486 B2 | 5/2010 | Ledbetter et al. |
| 7,763,712 B2 | 7/2010 | Crine et al. |
| 8,114,845 B2 | 2/2012 | Langermann et al. |
| 8,383,780 B2 | 2/2013 | Ledbetter et al. |
| 8,591,901 B2 | 11/2013 | Ledbetter et al. |
| 8,609,089 B2 | 12/2013 | Langermann et al. |
| 9,090,685 B2 | 7/2015 | Ledbetter et al. |
| 9,205,148 B2 | 12/2015 | Langermann et al. |
| 9,481,726 B2 | 11/2016 | Ledbetter et al. |
| 10,766,955 B2 | 9/2020 | Shapiro et al. |
| 10,844,115 B2 | 11/2020 | Qiu et al. |
| 11,242,384 B2 | 2/2022 | Shapiro et al. |
| 2003/0224501 A1 | 12/2003 | Young et al. |
| 2005/0276802 A1 | 12/2005 | Adams et al. |
| 2006/0263355 A1* | 11/2006 | Quan .............. A61K 39/39541 514/109 |
| 2012/0020967 A1 | 1/2012 | Barbas, III |
| 2012/0114648 A1 | 5/2012 | Langermann et al. |
| 2012/0114649 A1 | 5/2012 | Langermann et al. |
| 2013/0039911 A1 | 2/2013 | Atul et al. |
| 2013/0323244 A1 | 12/2013 | Crine et al. |
| 2014/0286933 A9 | 1/2014 | Schnieders et al. |
| 2014/0099254 A1 | 4/2014 | Chang et al. |
| 2015/0203579 A1 | 7/2015 | Papadopoulos et al. |
| 2015/0322530 A1 | 11/2015 | Orsulic et al. |
| 2016/0289315 A1 | 10/2016 | Mirza et al. |
| 2016/0304607 A1 | 10/2016 | Sadineni et al. |
| 2017/0066821 A1 | 3/2017 | Ledbetter et al. |
| 2018/0208650 A1 | 7/2018 | Qiu et al. |
| 2018/0244763 A1 | 8/2018 | Shapiro et al. |
| 2020/0399358 A1 | 12/2020 | Shapiro et al. |
| 2021/0163584 A1 | 6/2021 | Qiu et al. |

(Continued)

FOREIGN PATENT DOCUMENTS

| | | |
|---|---|---|
| EP | 1074563 A1 | 2/2001 |
| EP | 2350129 B1 | 6/2015 |
| EP | 2927240 A1 | 10/2015 |

(Continued)

OTHER PUBLICATIONS

Silva et al., J. Biol. Chem., 2015, vol. 290(9):5462-5469.*
Rabia et al., Biochem. Eng. J., 2018, vol. 137:365-374.*
Bedinger et al., MAbs, 2016, vol. 8(2):389-404.*
Hlavacek et al., "Steric Effects on Multivalent Ligand-Receptor Binding: Exclusion of Ligand Sites by Bound Cell Surface Receptors," Biophysical Journal (1999) 76:3031-43.
Pluckthun et al. "New protein engineering approaches to multivalent and bispecific antibody fragments," Immunotechnology (1997) 3:83-105.

(Continued)

*Primary Examiner* — Xiaozhen Xie
(74) *Attorney, Agent, or Firm* — Steptoe LLP; Z. Ying Li; Maurice Alvarez

(57) ABSTRACT

Provided are recombinant and chemically-conjugated antibodies and fragments thereof modified with one or more poly-aspartate (poly-D) peptides (e.g., a D10 sequence) to improve localization of the antibodies or fragments to bone. Methods of making and using of these antibodies and fragments also are disclosed.

13 Claims, 41 Drawing Sheets

Specification includes a Sequence Listing.

(56) References Cited

U.S. PATENT DOCUMENTS

2022/0195026 A1  6/2022  Shapiro et al.

FOREIGN PATENT DOCUMENTS

| WO | WO 94/13804 A1 | 6/1994 | |
|---|---|---|---|
| WO | WO 97/13844 A1 | 4/1997 | |
| WO | WO 97/29131 A1 | 8/1997 | |
| WO | WO 2004/098637 A1 | 11/2000 | |
| WO | WO 2005/097832 A2 | 10/2001 | |
| WO | WO 2004/060920 A1 | 7/2004 | |
| WO | WO 2005/010049 A2 | 2/2005 | |
| WO | WO 2006/086469 A2 | 8/2006 | |
| WO | 2008145142 A1 | 12/2008 | |
| WO | 2009/088805 A2 | 7/2009 | |
| WO | 2010/072691 A1 | 7/2010 | |
| WO | WO 2010/124276 A2 | 10/2010 | |
| WO | WO 2011/109789 A2 | 9/2011 | |
| WO | 2012130831 A1 | 10/2012 | |
| WO | WO 2012/145493 A1 | 10/2012 | |
| WO | 2012/174001 A2 | 12/2012 | |
| WO | WO 2012/167143 A1 | 12/2012 | |
| WO | 2013/059491 A1 | 4/2013 | |
| WO | 2013/178736 A1 | 12/2013 | |
| WO | WO-2014153435 A1 * | 9/2014 | ............ A61K 33/42 |
| WO | WO 2014/182676 A2 | 11/2014 | |
| WO | WO 2015/035606 A1 | 3/2015 | |
| WO | WO 2015/112800 A1 | 7/2015 | |
| WO | WO 2015/112900 A1 | 7/2015 | |
| WO | WO 2015/140150 A1 | 9/2015 | |
| WO | 2016061142 A1 | 4/2016 | |
| WO | WO2 016/057933 A1 | 4/2016 | |
| WO | WO 2016/092419 A1 | 6/2016 | |
| WO | WO 2016/123573 A1 | 8/2016 | |
| WO | 2015095418 A1 | 9/2016 | |
| WO | 2016141245 A1 | 9/2016 | |
| WO | 2016161410 A2 | 10/2016 | |
| WO | WO 2017/011773 A2 | 1/2017 | |
| WO | WO 2017/037634 A1 | 3/2017 | |
| WO | WO 2018/027329 A1 | 2/2018 | |

OTHER PUBLICATIONS

Roitt et al., "Interaction of Antibodies with Antigens Antibodies form multiple non-covalent bonds with antigen," Immunology (2000) 592:150.

Aalberse et al., "IgG4 breaking the rules," Immunology 105: 9-19 (2002).

Akhurst et al., "Targeting the TGFβ signalling pathway in disease," Nat Rev Drug Discov. 11(10):790-811 (2012).

Angal el al., "A single amino acid substitution abolishes the heterogeneity of chimeric mouse/human (IgG4) antibody," Mol Immunol 30(1):105-8 (1993).

Arteaga et al., "Anti-transforming growth factor (TGF)-β antibodies inhibit breast cancer cell tumorigenicity and increase mouse spleen natural killer cell activity. Implications for a possible role of tumor cell/host TGF-beta interactions in human breast cancer progression," J Clin Invest 92:2569-2576 (1993).

Becht et al., "Cancer immune contexture and immunotherapy," Curr Opin Immunol 39:7-13 (2016).

Becht et al., "Estimating the population abundance of tissue-infiltrating immune and stromal cell populations using gene expression," Genome Biol 17:218 (2016).

Bedinger et al., "Development and characterization of human monoclonal antibodies that neutralize multiple TGFβ isoforms," MAbs. 8(2):389-404 (2016).

Behrens et al., "Methods for site-specific drug conjugation to antibodies," mAbs 6(1):46-53 (2014).

Bloom et al., "Intrachain disulfide bond in the core hinge region of human IgG4," Protein Science 6:407-415 (1997).

Bonewald, "Regulation and regulatory activities of transforming growth factor β," Crit Rev Eukaryot Gene Expr. 9(1):33-44 (1999).

Border et al., "Fibrosis linked to TGF-β in yet another disease," J Clin Invest 96:655-656 (1995).

Border et al., "Suppression of experimental glomerulonephritis by antiserum against transforming growth factor β1," Nature 346:371-374 (1990).

Border et al., "Targetting TGF-β for treatment of disease," Nat. Med. 1(10):1000-1001 (1995).

Border et al., "TGF-β," Scientific American—Science & Medicine 68-77 (Jan./Feb. 1995).

Border et al., "Transforming growth factor β in tissue fibrosis," New Eng. J Med. 331(19):1286-1292 (1994).

Chen et al., "TGF-β and BMP signaling in osteoblast differentiation and bone formation," Int. J. Biol. Sci. 8(2): 272-88 (2012).

Chen et al., "Fusion protein linkers: property, design and functionality," Adv Drug Deliv Rev 65(10):1357-1369 (2013).

Connolly et al., "Complexities of TGF-β Targeted Cancer Therapy," Int J Biol Sci 8(7):964-78 (2012).

Cuende et al., "Monoclonal antibodies against GARP/TGF-β1 complexes inhibit the immunosuppressive activity of human regulatory T cells in vivo," Sci Transl Med. 7:284ra56 (2015).

Dalal et al., "Immunocytochemical localization of secreted transforming growth factor-β1 to the advancing edges of primary tumors and to lymph node metastases of human mammary carcinoma," American Journal of Pathology 143:381-389 (1993).

Danielpour et al., "Immunodetection and quantitation of the two forms of transforming growth factor-beta (TGF-β1 and TGF-β2) secreted by cells in culture," J Cell. Physiol. 138:79-86 (1989).

Danielpour et al., "Sandwich enzyme-linked immunosorbent assays (SELISAs) quantitate and distinguish two forms of transforming growth factor-beta (TGF-β1 and TGF-β2) in complex biological fluids," Growth Factors 2:61-71 (1989).

Dasch et al., "Monoclonal antibodies recognizing transforming growth factor-β. Bioactivity neutralization and transforming growth factor β2 affinity purification," The Journal of Immunology 142(5):1536-1541 (1989).

Davies et al., "Human IgG4: a structural perspective," Immunological Reviews 268:139-159 (2015).

Durocher et al., "High-level and high-throughput recombinant protein production by transient transfection of suspension-growing human 293-EBNA1 cells," Nucl. Acids Res. 30(2):E9 (2002).

Feyler et al., "Tumour cell generation of inducible regulatory T-cells in multiple myeloma is contact-dependent and antigen-presenting cell-independent," PLoS One 7(5):e35981, 11 pages (2012).

Flanders et al., "Antibodies to peptide determinants in transforming growth factor β and their applications," Biochemistry 27:739-746 (1988).

Flavell et al., "The polarization of immune cells in the tumour environment by TGFbeta," Nature Reviews Immunology 10:554-567 (2010).

Fridman et al., "The immune contexture in human tumours: impact on clinical outcome," Nat Rev Cancer 12(4):298-306 (2012).

Friedman et al., "High levels of transforming growth factor β1 correlate with disease progression in human colon cancer," Cancer Epidemiology, Biomarkers & Prevention 4: 549-554 (1995).

Galon et al., "The continuum of cancer immunosurveillance: prognostic, predictive, and mechanistic signatures," Immunity 39(1):11-26 (2013).

Giri et al., "Effect of antibody to transforming growth factor β on bleomycin induced accumulation of lung collagen in mice," Thorax 48:959-966 (1993).

Griffith et al., "Three-dimensional structure of recombinant human osteogenic protein 1: structural paradigm for the transforming growth factor beta superfamily," Proc. Natl. Acad. Sci. USA 93:878-883 (1996).

Hirashima et al., "Transforming growth factor-β1 produced by ovarian cancer cell line HRA stimulates attachment and invasion through an up-regulation of plasminogen activator inhibitor Type-1 in human peritoneal mesothelial cells," Journal of Biological Chemistry 278: 26793-26802 (2003).

Hocevar et al., "TGF-β induces fibronectin synthesis through a c-Jun N-terminal kinase-dependent, Smad4-independent pathway," The EMBO Journal 18(5):1345-1356 (1999).

(56) References Cited

OTHER PUBLICATIONS

Hoefer et al., "Anti-(transforming growth factor β) antibodies with predefined specificity inhibit metastasis of highly tumorigenic human xenotransplants in nu/nu mice," Cancer Immunol. Immunother 41:302-308 (1995).

Ignotz et al., "Transforming growth factor-β stimulates the expression of fibronectin and collagen and their incorporation into the extracellular matrix," J Biol. Chem. 261(9):4337-4345 (1986).

Ikeda et al., "The roles of IFN gamma in protection against tumor development and cancer immunoediting," Cytokine Growth Factor Rev 13:95-109 (2002).

Jackson, "Modulation of the activity of transforming growth factor beta," Expert Opinion on Therapeutic Patents 8(11):1479-1486 (1998).

Kadam et al., "A canonical transforming growth factor β-dependent signaling pathway is present in peripheral blood cells of cancer patients with skeletal metastasis," Journal of Molecular Biomarkers & Diagnosis 4:153 (2013).

Khanna et al., "Transforming growth factor (TGF)-β mimics and anti-TGF-β antibody abrogates the in vivo effects of cyclosporine," Transplantation 67(6):882-889 (1999).

Kim et al., "Multi-cellular natural killer (NK) cell clusters enhance NK cell activation through localizing IL-2 within the cluster," Scientific Reports 7:40623 (2017).

Kjellman et al., "Expression of TGF-β isoforms, TGF-β receptors, and SMAD molecules at different stages of human glioma," Int. J. Cancer (Pred. Oncol.) 89: 251-258 (2000).

Labrijn et al., "Therapeutic IgG4 antibodies engage in Fab-arm exchange with endogenous human IgG4 in vivo," Nature Biotechnology 27: 767-773 (2009).

Larkin et al., "Combined nivolumab and ipilimumab or monotherapy in untreated melanoma," N Engl J Med 373:23-34 (2015).

Leask et al., "TGF-β signaling and the fibrotic response," FASEB J 18:816-827 (2004).

Lee et al., "Transforming growth factor β induces vascular endothelial growth factor elaboration from pleural mesothelial cells in vivo and in vitro," Am J Respir Crit Care Med 165:88-94 (2002).

Lei et al., "Autocrine TGFβ supports growth and survival of human breast cancer MDA-MB-231 cells," Oncogene 21:7514-7523 (2002).

Lewis et al., "Tumour-derived TGF-β1 modulates myofibroblast differentiation and promotes HGF/SF-dependent invasion of squamous carcinoma cells," British Journal of Cancer 90:822-832 (2004).

Lin et al., "Regulation of fibronectin by thyroid hormone receptors," J Mol Endocrinol 33:445-458 (2004).

Ling et al., "Therapeutic role of TGF-β-neutralizing antibody in mouse cyclosporin A nephropathy: Morphologic improvement associated with functional preservation," J Am. Soc. Nephrol. 14:377-388 (2003).

Liu et al., "Neutralizing TGF-β1 antibody infusion in neonatal rat delays in vivo glomerular capillary formation," Kidney Int 56:1334-1348 (1999).

Liu et al., "Role of TGF-β in a mouse model of high turnover renal osteodystrophy," J. Bone Miner Res. 29(5):1141-57 (2014).

Lo et al., "Evaluation of fluorescence-based thermal shift assays for hit identification in drug discovery," Anal. Biochem. 332(1):153-9 (2004).

Logan et al., "Effects of transforming growth factor β1 on scar production in the injured central nervous system of the rat," Eur. J Neurosci. 6:355-363 (1994).

Lucas et al., "The autocrine production of transforming growth factor-β1 during lymphocyte activation—A study with a monoclonal antibody-based ELISA," The Journal of Immunology 145(5):1415-1422 (1990).

Lyons et al., "Transforming growth factors and the regulation of cell proliferation," Eur J Biochem 187:467-473 (1990).

Ma et al., "Progress of immunotherapy for hepatocellular carcinoma," Immuno-Gastroenterology 2(3):167-172 (2013).

Massagué, "TGFβ in cancer," Cell 134(2): 215-230 (2008).

Mittl et al., "The crystal structure of TGF-β3 and cmparison to TGF-β2: Implications for receptor binding," Protein Science 5:1261-1271 (1996).

Miyajima et al., "Antibody to transforming growth factor-β ameliorates tubular apoptosis in unilateral ureteral obstruction," Kidney Int. 58:2301-2313 (2000).

Mookerjee et al., "Immunosuppression in hamsters with progressive visceral leishmaniasis is associated with an impairment of protein kinase C activity in their lymphocytes that can be partially reversed by okadaic acid or anti-transforming growth factor beta antibody," Infection and Immunity 71:2439-2446 (2003).

Morris et al., "Phase I study of GC1008 (Fresolimumab): A human anti-transforming growth factor-beta (TGFβ) monoclonal antibody in patients with advanced malignant melanoma or renal cell carcinoma," PLoS One 9:e90353 (2014).

Newman et al., "Modification of the Fc region of a primatized IgG antibody to human CD4 retains its ability to modulate cd4 receptors but does not deplete CD4+ T cells in chimpanzees," Clinical Immunology 98:164-174 (2001).

Peters et al., "Targeting TGF-β overexpression in renal disease: maximizing the antifibrotic action of angiotensin II blockade," Kidney Int 54:1570-1580 (1998).

Pintavorn et al., "TGF-β and the endothelium during immune injury," Kidney Int 51:1401-1412 (1997).

Redman et al., "Advances in immunotherapy for melanoma," BMC Med 14:20-30 (2016).

Rispens et al., "Mechanism of Immunoglobulin G4 Fab-arm Exchange," J. Am. Chem. Soc. 133:10302-10311 (2011).

Salas-Solano et al., "Optimization and validation of a quantitative capillary electrophoresis sodium dodecyl sulfate method for quality control and stability monitoring of monoclonal antibodies," Anal Chem 78:6583-94 (2006).

Schneider et al., "Monocyte chemoattractant protein-1 mediates collagen deposition in experimental glomerulonephritis by transforming growth factor-β," Kidney Int. 56:135-144 (1999).

Schuurman et al., "The inter-heavy chain disulfide bonds of IgG4 are in equilibrium with intra-chain disulfide bonds," Mol Immunol. 38(1):1-8 (2001).

Schuurman, "IgG4 Fab-arm exchange," 28 pages, Copenhagen Oct. 27, 2010.

Shah et al., "Neutralising antibody to TGF-beta 1,2 reduces cutaneous scarring in adult rodents," J Cell. Sci. 107:1137-1157 (1994).

Shenkar et al., "Anti-transforming growth factor-β monoclonal antibodies prevent lung injury in hemorrhaged mice," Am. J Respir. Cell. Mol. Biol. 11:351-357 (1994).

Silva et al., "The S228P mutation prevents in vivo and in vitro IgG4 Fab-arm exchange as demonstrated using a combination of novel quantitative immunoassays and physiological matrix preparation," J Biol Chem. 290:5462-9 (2015).

Sinha et al., "Transforming growth factor-β1 signaling contributes to development of smooth muscle cells from embryonic stem cells," Am J Physiol Cell Physiol 287:C1560-C1568 (2004).

Tahara et al., "Synthetic peptide-generated monoclonal antibodies to transforming growth factor-β1," Hybridoma 12(4):441-453 (1993).

Tauriello et al., "TGFβ drives immune evasion in genetically reconstituted colon cancer metastasis," Nature 554(7693):538-543 (2018).

Tempest et al., "Human antibodies specific for human TGF-β derived from phage display libraries," Immunotechnology 2:306 (1996).

Thompson et al., "A fully human antibody neutralising biologically active human TGFbeta2 for use in therapy," Journal of Immunological Methods 227:17-29 (1999).

Trotta et al., "TGF-beta utilizes SMAD3 to inhibit CD16-mediated IFN-gamma production and antibody-dependent cellular cytotoxicity in human NK cells," Journal of immunology 181:3784-3792 (2008).

Vanpouille-Box et al., "TGFβ is a master regulator of radiation therapy-induced antitumor immunity," Cancer Res 75(11):2232-2242 (2015).

Wang et al., "Transforming growth factor-β1 stimulates vascular endothelial growth factor 164 via mitogen-activated protein kinase

(56) References Cited

OTHER PUBLICATIONS kinase 3-p38α and p38δ mitogen-activated protein kinase-dependent pathway in murine mesangial cells," J Biol Chem 279:33213-33219 (2004).
Weeks et al., "Inducible expression of transforming growth factor β1 in papillomas causes rapid metastasis," Cancer Research 61:7435-7443 (2001).
Yang et al., "Comprehensive analysis of the therapeutic IgG4 antibody pembrolizumab: hinge modification blocks half molecule exchange in vitro and in vivo," Journal of Pharmaceutical Sciences 104:4002-4014 (2015).
Yingling et al., "Development of TGF-beta signaling inhibitors for cancer therapy," Nature Review/Drug Discovery 3:1011-1022 (2004).
U.S. Appl. No. 62/373,597, filed Aug. 11, 2016.
Finkelstein A.V., Ptitsin O.B., "Protein Physics: Lecture course with color and stereoscopic illustrations and tasks: a training manual/ A.V. Finkelstein, O.B., Ptitsin."—4th ed. (2012) p. 23 (English Translation).
Hugo et al., "Genomic and transcriptomic features of response to anti-PD-1 therapy in metastatic melanoma," Cell (2016) 165:35-44.
Jiang et al., "Signatures of T cell dysfunction and exclusion predict cancer immunotherapy response," Nature Medicine (2018).
Labrijn et al., "Species-specific determinants in the IgG CH3 domain enable Fab-arm exchange by affecting the noncovalent CH3-CH3 interaction strength," J Immunol. (2011) 187(6):3238-46.
Lan et al., "Enhanced preclinical antitumor activity of M7824, a bifunctional fusion protein simultaneously targeting PD-L1 and TGF-β," Sci Transl Med.(2008) 10(424).
Lewis, K.B., et al., "Comparision of the ability of wild-type and stabilized human IgG4 to undergo Fab arm exchange with endogenous IgG4 in vitro and in vivo," Mol. Immunology (2009) 46:3488-3494.
MacCallum et al., "Antibody-antigen interactions: contact analysis and binding site topography," J Mol Biol. (1996) 262(5):732-45.

Malaspina et al., "Enhanced programmed death 1 (PD-1) and PD-1 ligand (PD-L1) expression in patients with actinic cheilitis and oral squamous cell carcinoma," Cancer Immunol Immunother (2011) 60:965-974.
Mariathasan et al., "TGF-B Signalling Attenuates Tumour Response to PD-L1 Checkpoint Blockade by Contributing to Retention of T Cells in the Peritumoural Stroma," Abstract 8O_PR, ESMO Immuno Oncology Congress, European Society for Medical Oncology (2017) 16-17.
Pardoll, "Cancer immunotherapy through checkpoint blockade: the future of cancer treatment," Medicographia (2014) 36:274-284.
Terabe et al., "Blockade of only TGF-β 1 and 2 is sufficient to enhance the efficacy of vaccine and PD-1 checkpoint blockade immunotherapy," Oncolmmunology vol. 6, Issue 5 e1308616 (13 pages) (2017).
Thomson Pharma literature and new report, https://media.nature.com/original/nature-assets/nbt/journal/v28/n2/extref/nbt0210 -123-S1.pdf, 4 pages (2010).
Silva et al., "Quantifying Fab arm exchange using novel methodologies," J. Biol. Chem. published online: 19 pages (Jan. 7, 2015).
Santarpia et al., "Programmed cell death protein-1/programmed cell death ligand-1 pathway inhibition and predictive biomarkers: understanding transforming growth factor-beta role," Transl Lung Cancer Res (2015) 4(6):728-742.
Vajdos et al., "Comprehensive functional maps of the antigen-binding site of an anti-ErbB2 antibody obtained with shotgun scanning mutagenesis," J Mol Biol. (2002) 320(2):415-28.
Wu et al., "Humanization of a murine monoclonal antibody by simultaneous optimization of framework and CDR residues," J Mol Biol. (1999) 294(1):151-62.
Yang et al., The role of mesenchymal stem/progenitor cells in sarcoma: update and dispute. Stem Cell Investigation, (2014) 1:18.
Guo YJ., "Progress in monoclonal antibody-based immunotherapy for cancer treatment", Chin J Biotech. (2015) 31(6):857-70 (Partial English translation).

\* cited by examiner

SEQUENCE LISTING

<160> NUMBER OF SEQ ID NOS: 40

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asp Asp Asp Asp Asp Asp Asp Asp Asp Asp
1               5                   10

<210> SEQ ID NO 2
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

His Val Gln Leu Gln Gln Ser Gly Pro Glu Leu Val Arg Pro Gly Ala
1               5                   10                  15

```
Ser Val Lys Leu Ser Cys Lys Ala Ser Gly Tyr Ile Phe Ile Thr Tyr
            20                  25                  30
Trp Met Asn Trp Val Lys Gln Arg Pro Gly Gln Gly Leu Glu Trp Ile
            35                  40                  45
Gly Gln Ile Phe Pro Ala Ser Gly Ser Thr Asn Tyr Asn Glu Met Phe
 50                  55                  60
Glu Gly Lys Ala Thr Leu Thr Val Asp Thr Ser Ser Ser Thr Ala Tyr
 65                  70                  75                  80
Met Gln Leu Ser Ser Leu Thr Ser Glu Asp Ser Ala Val Tyr Tyr Cys
            85                  90                  95
Ala Arg Gly Asp Gly Asn Tyr Ala Leu Asp Ala Met Asp Tyr Trp Gly
            100                 105                 110
Gln Gly Thr Ser Val Thr Val Ser Ser Ala Lys Thr Thr Pro Pro Ser
            115                 120                 125
Val Tyr Pro Leu Ala Pro Gly Ser Ala Ala Gln Thr Asn Ser Met Val
    130                 135                 140
Thr Leu Gly Cys Leu Val Lys Gly Tyr Phe Pro Glu Pro Val Thr Val
145                 150                 155                 160
Thr Trp Asn Ser Gly Ser Leu Ser Ser Gly Val His Thr Phe Pro Ala
            165                 170                 175
Val Leu Gln Ser Asp Leu Tyr Thr Leu Ser Ser Ser Val Thr Val Pro
            180                 185                 190
Ser Ser Thr Trp Pro Ser Gln Thr Val Thr Cys Asn Val Ala His Pro
            195                 200                 205
Ala Ser Ser Thr Lys Val Asp Lys Lys Ile Val Pro Arg Asp Cys Gly
            210                 215                 220
Cys Lys Pro Cys Ile Cys Thr Val Pro Glu Val Ser Ser Val Phe Ile
225                 230                 235                 240
Phe Pro Pro Lys Pro Lys Asp Val Leu Thr Ile Thr Leu Thr Pro Lys
            245                 250                 255
Val Thr Cys Val Val Val Asp Ile Ser Lys Asp Asp Pro Glu Val Gln
            260                 265                 270
Phe Ser Trp Phe Val Asp Asp Val Glu Val His Thr Ala Gln Thr Lys
            275                 280                 285
Pro Arg Glu Glu Gln Phe Asn Ser Thr Phe Arg Ser Val Ser Glu Leu
            290                 295                 300
Pro Ile Met His Gln Asp Trp Leu Asn Gly Lys Glu Phe Lys Cys Arg
305                 310                 315                 320
Val Asn Ser Ala Ala Phe Pro Ala Pro Ile Glu Lys Thr Ile Ser Lys
            325                 330                 335
Thr Lys Gly Arg Pro Lys Ala Pro Gln Val Tyr Thr Ile Pro Pro Pro
            340                 345                 350
Lys Glu Gln Met Ala Lys Asp Lys Val Ser Leu Thr Cys Met Ile Thr
            355                 360                 365
Asp Phe Phe Pro Glu Asp Ile Thr Val Glu Trp Gln Trp Asn Gly Gln
            370                 375                 380
Pro Ala Glu Asn Tyr Lys Asn Thr Gln Pro Ile Met Asp Thr Asp Gly
385                 390                 395                 400
Ser Tyr Phe Val Tyr Ser Lys Leu Asn Val Gln Lys Ser Asn Trp Glu
            405                 410                 415
Ala Gly Asn Thr Phe Thr Cys Ser Val Leu His Glu Gly Leu His Asn
            420                 425                 430
```

```
His His Thr Glu Lys Ser Leu Ser His Ser Pro Gly Lys
            435                 440                 445
```

<210> SEQ ID NO 3
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
His Val Gln Leu Gln Gln Ser Gly Pro Glu Leu Val Arg Pro Gly Ala
1               5                   10                  15

Ser Val Lys Leu Ser Cys Lys Ala Ser Gly Tyr Ile Phe Ile Thr Tyr
            20                  25                  30

Trp Met Asn Trp Val Lys Gln Arg Pro Gly Gln Gly Leu Glu Trp Ile
        35                  40                  45

Gly Gln Ile Phe Pro Ala Ser Gly Ser Thr Asn Tyr Asn Glu Met Phe
    50                  55                  60

Glu Gly Lys Ala Thr Leu Thr Val Asp Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Asp Gly Asn Tyr Ala Leu Asp Ala Met Asp Tyr Trp Gly
            100                 105                 110

Gln Gly Thr Ser Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Pro
            180                 185                 190

Ser Ser Thr Trp Pro Ser Gln Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Asp Ile Ser Lys Asp Asp Pro Glu Val Gln
            260                 265                 270

Phe Ser Trp Phe Val Asp Asp Val Glu Val His Thr Ala Gln Thr Lys
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350
```

-continued

```
Lys Glu Gln Met Ala Lys Asp Lys Val Ser Leu Thr Cys Met Ile Thr
            355                 360                 365
Asp Phe Phe Pro Glu Asp Ile Thr Val Glu Trp Gln Trp Asn Gly Gln
370                 375                 380
Pro Ala Glu Asn Tyr Lys Asn Thr Gln Pro Ile Met Asp Thr Asp Gly
385                 390                 395                 400
Ser Tyr Phe Val Tyr Ser Lys Leu Asn Val Gln Lys Ser Asn Trp Glu
                405                 410                 415
Ala Gly Asn Thr Phe Thr Cys Ser Val Leu His Glu Gly Leu His Asn
            420                 425                 430
His His Thr Glu Lys Ser Leu Ser His Ser Pro Gly Lys Asp Asp Asp
        435                 440                 445
Asp Asp Asp Asp Asp Asp
    450                 455

<210> SEQ ID NO 4
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Asp Asp Asp Asp Asp Asp Asp His Val Gln Leu Gln Gln
1               5                   10                  15
Ser Gly Pro Glu Leu Val Arg Pro Gly Ala Ser Val Lys Leu Ser Cys
            20                  25                  30
Lys Ala Ser Gly Tyr Ile Phe Ile Thr Tyr Trp Met Asn Trp Val Lys
        35                  40                  45
Gln Arg Pro Gly Gln Gly Leu Glu Trp Ile Gly Gln Ile Phe Pro Ala
    50                  55                  60
Ser Gly Ser Thr Asn Tyr Asn Glu Met Phe Glu Gly Lys Ala Thr Leu
65                  70                  75                  80
Thr Val Asp Thr Ser Ser Ser Thr Ala Tyr Met Gln Leu Ser Ser Leu
                85                  90                  95
Thr Ser Glu Asp Ser Ala Val Tyr Tyr Cys Ala Arg Gly Asp Gly Asn
            100                 105                 110
Tyr Ala Leu Asp Ala Met Asp Tyr Trp Gly Gln Gly Thr Ser Val Thr
        115                 120                 125
Val Ser Ser Ala Lys Thr Thr Pro Pro Ser Val Tyr Pro Leu Ala Pro
    130                 135                 140
Gly Ser Ala Ala Gln Thr Asn Ser Met Val Thr Leu Gly Cys Leu Val
145                 150                 155                 160
Lys Gly Tyr Phe Pro Glu Pro Val Thr Val Thr Trp Asn Ser Gly Ser
                165                 170                 175
Leu Ser Ser Gly Val His Thr Phe Pro Ala Val Leu Gln Ser Asp Leu
            180                 185                 190
Tyr Thr Leu Ser Ser Ser Val Thr Val Pro Ser Ser Thr Trp Pro Ser
        195                 200                 205
Gln Thr Val Thr Cys Asn Val Ala His Pro Ala Ser Ser Thr Lys Val
    210                 215                 220
Asp Lys Lys Ile Val Pro Arg Asp Cys Gly Cys Lys Pro Cys Ile Cys
225                 230                 235                 240
Thr Val Pro Glu Val Ser Ser Val Phe Ile Phe Pro Pro Lys Pro Lys
```

```
                        245                 250                 255
Asp Val Leu Thr Ile Thr Leu Thr Pro Lys Val Thr Cys Val Val Val
                260                 265                 270

Asp Ile Ser Lys Asp Asp Pro Glu Val Gln Phe Ser Trp Phe Val Asp
            275                 280                 285

Asp Val Glu Val His Thr Ala Gln Thr Lys Pro Arg Glu Glu Gln Phe
        290                 295                 300

Asn Ser Thr Phe Arg Ser Val Ser Glu Leu Pro Ile Met His Gln Asp
305                 310                 315                 320

Trp Leu Asn Gly Lys Glu Phe Lys Cys Arg Val Asn Ser Ala Ala Phe
                325                 330                 335

Pro Ala Pro Ile Glu Lys Thr Ile Ser Lys Thr Lys Gly Arg Pro Lys
            340                 345                 350

Ala Pro Gln Val Tyr Thr Ile Pro Pro Lys Glu Gln Met Ala Lys
        355                 360                 365

Asp Lys Val Ser Leu Thr Cys Met Ile Thr Asp Phe Phe Pro Glu Asp
370                 375                 380

Ile Thr Val Glu Trp Gln Trp Asn Gly Gln Pro Ala Glu Asn Tyr Lys
385                 390                 395                 400

Asn Thr Gln Pro Ile Met Asp Thr Asp Gly Ser Tyr Phe Val Tyr Ser
                405                 410                 415

Lys Leu Asn Val Gln Lys Ser Asn Trp Glu Ala Gly Asn Thr Phe Thr
            420                 425                 430

Cys Ser Val Leu His Glu Gly Leu His Asn His His Thr Glu Lys Ser
        435                 440                 445

Leu Ser His Ser Pro Gly Lys
450                 455

<210> SEQ ID NO 5
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Asp Asp Asp Asp Asp Asp Asp His Val Gln Leu Gln Gln
1               5                   10                  15

Ser Gly Pro Glu Leu Val Arg Pro Gly Ala Ser Val Lys Leu Ser Cys
                20                  25                  30

Lys Ala Ser Gly Tyr Ile Phe Ile Thr Tyr Trp Met Asn Trp Val Lys
            35                  40                  45

Gln Arg Pro Gly Gln Gly Leu Glu Trp Ile Gly Gln Ile Phe Pro Ala
        50                  55                  60

Ser Gly Ser Thr Asn Tyr Asn Glu Met Phe Glu Gly Lys Ala Thr Leu
65                  70                  75                  80

Thr Val Asp Thr Ser Ser Ser Thr Ala Tyr Met Gln Leu Ser Ser Leu
                85                  90                  95

Thr Ser Glu Asp Ser Ala Val Tyr Tyr Cys Ala Arg Gly Asp Gly Asn
            100                 105                 110

Tyr Ala Leu Asp Ala Met Asp Tyr Trp Gly Gln Gly Thr Ser Val Thr
        115                 120                 125

Val Ser Ser Ala Lys Thr Thr Pro Pro Ser Val Tyr Pro Leu Ala Pro
    130                 135                 140
```

Gly Ser Ala Ala Gln Thr Asn Ser Met Val Thr Leu Gly Cys Leu Val
145                 150                 155                 160

Lys Gly Tyr Phe Pro Glu Pro Val Thr Val Thr Trp Asn Ser Gly Ser
            165                 170                 175

Leu Ser Ser Gly Val His Thr Phe Pro Ala Val Leu Gln Ser Asp Leu
        180                 185                 190

Tyr Thr Leu Ser Ser Ser Val Thr Val Pro Ser Ser Thr Trp Pro Ser
    195                 200                 205

Gln Thr Val Thr Cys Asn Val Ala His Pro Ala Ser Ser Thr Lys Val
    210                 215                 220

Asp Lys Lys Ile Val Pro Arg Asp Cys Gly Cys Lys Pro Cys Ile Cys
225                 230                 235                 240

Thr Val Pro Glu Val Ser Ser Val Phe Ile Phe Pro Pro Lys Pro Lys
                245                 250                 255

Asp Val Leu Thr Ile Thr Leu Thr Pro Lys Val Thr Cys Val Val Val
            260                 265                 270

Asp Ile Ser Lys Asp Asp Pro Glu Val Gln Phe Ser Trp Phe Val Asp
        275                 280                 285

Asp Val Glu Val His Thr Ala Gln Thr Lys Pro Arg Glu Glu Gln Phe
290                 295                 300

Asn Ser Thr Phe Arg Ser Val Ser Glu Leu Pro Ile Met His Gln Asp
305                 310                 315                 320

Trp Leu Asn Gly Lys Glu Phe Lys Cys Arg Val Asn Ser Ala Ala Phe
                325                 330                 335

Pro Ala Pro Ile Glu Lys Thr Ile Ser Lys Thr Lys Gly Arg Pro Lys
            340                 345                 350

Ala Pro Gln Val Tyr Thr Ile Pro Pro Pro Lys Glu Gln Met Ala Lys
        355                 360                 365

Asp Lys Val Ser Leu Thr Cys Met Ile Thr Asp Phe Phe Pro Glu Asp
    370                 375                 380

Ile Thr Val Glu Trp Gln Trp Asn Gly Gln Pro Ala Glu Asn Tyr Lys
385                 390                 395                 400

Asn Thr Gln Pro Ile Met Asp Thr Asp Gly Ser Tyr Phe Val Tyr Ser
                405                 410                 415

Lys Leu Asn Val Gln Lys Ser Asn Trp Glu Ala Gly Asn Thr Phe Thr
            420                 425                 430

Cys Ser Val Leu His Glu Gly Leu His Asn His His Thr Glu Lys Ser
        435                 440                 445

Leu Ser His Ser Pro Gly Lys Asp Asp Asp Asp Asp Asp Asp Asp Asp
    450                 455                 460

Asp
465

<210> SEQ ID NO 6
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

```
Gly Asn Ser Phe Met His Trp Tyr Gln Gln Lys Ser Gly Gln Pro Pro
            35                  40                  45

Lys Leu Leu Ile Tyr Leu Ala Ser Asn Leu Glu Ser Gly Val Pro Ala
 50                  55                  60

Arg Phe Ser Gly Ser Gly Ser Arg Thr Asp Phe Thr Leu Thr Ile Asp
 65                  70                  75                  80

Pro Val Glu Ala Asp Asp Ala Ala Thr Tyr Tyr Cys Gln Gln Asn Asn
                85                  90                  95

Glu Asp Pro Leu Thr Phe Gly Ala Gly Thr Lys Leu Glu Leu Lys Arg
            100                 105                 110

Ala Asp Ala Ala Pro Thr Val Ser Ile Phe Pro Pro Ser Ser Glu Gln
            115                 120                 125

Leu Thr Ser Gly Gly Ala Ser Val Val Cys Phe Leu Asn Asn Phe Tyr
130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
            195                 200                 205

Ile Val Lys Ser Phe Asn Arg Asn Glu Cys
210                 215

<210> SEQ ID NO 7
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Asp Asp Asp Asp Asp Asp Asp Asp Asn Ile Val Leu Thr Gln
1               5                   10                  15

Ser Pro Ala Ser Leu Ala Val Ser Leu Gly Gln Arg Ala Thr Ile Ser
                20                  25                  30

Cys Arg Ala Ser Glu Ser Val Asp Ser Tyr Gly Asn Ser Phe Met His
            35                  40                  45

Trp Tyr Gln Gln Lys Ser Gly Gln Pro Pro Lys Leu Leu Ile Tyr Leu
 50                  55                  60

Ala Ser Asn Leu Glu Ser Gly Val Pro Ala Arg Phe Ser Gly Ser Gly
 65                  70                  75                  80

Ser Arg Thr Asp Phe Thr Leu Thr Ile Asp Pro Val Glu Ala Asp Asp
                85                  90                  95

Ala Ala Thr Tyr Tyr Cys Gln Gln Asn Asn Glu Asp Pro Leu Thr Phe
            100                 105                 110

Gly Ala Gly Thr Lys Leu Glu Leu Lys Arg Ala Asp Ala Ala Pro Thr
            115                 120                 125

Val Ser Ile Phe Pro Pro Ser Ser Glu Gln Leu Thr Ser Gly Gly Ala
130                 135                 140

Ser Val Val Cys Phe Leu Asn Asn Phe Tyr Pro Lys Asp Ile Asn Val
145                 150                 155                 160

Lys Trp Lys Ile Asp Gly Ser Glu Arg Gln Asn Gly Val Leu Asn Ser
```

```
                    165                 170                 175
Trp Thr Asp Gln Asp Ser Lys Asp Ser Thr Tyr Ser Met Ser Ser Thr
                180                 185                 190

Leu Thr Leu Thr Lys Asp Glu Tyr Glu Arg His Asn Ser Tyr Thr Cys
            195                 200                 205

Glu Ala Thr His Lys Thr Ser Thr Ser Pro Ile Val Lys Ser Phe Asn
        210                 215                 220

Arg Asn Glu Cys
225

<210> SEQ ID NO 8
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Ser Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Ala Ala Thr Tyr Tyr Cys Gln Gln Asn Asn
                85                  90                  95

Glu Asp Pro Leu Thr Phe Gly Ala Gly Thr Lys Leu Glu Leu Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys Asp Asp Asp Asp Asp
    210                 215                 220

Asp Asp Asp Asp
225

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 9

Gly Gly Gly Gly Ser
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Gly Gly Ser Gly Gly Gly Gly Ser
1               5                   10

<210> SEQ ID NO 11
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Ser Phe Met His Trp Tyr Gln Gln Lys Ser Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Leu Thr Phe Gly Ala Gly Thr Lys Leu Glu Leu Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys Gly Gly Gly Gly Ser Asp
    210                 215                 220

Asp Asp Asp Asp Asp Asp Asp Asp
225                 230

<210> SEQ ID NO 12
<211> LENGTH: 238
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 12

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
                20                  25                  30

Gly Asn Ser Phe Met His Trp Tyr Gln Gln Lys Ser Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Leu Thr Phe Gly Ala Gly Thr Lys Leu Glu Leu Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys Gly Gly Gly Ser Gly
    210                 215                 220

Gly Gly Gly Ser Asp Asp Asp Asp Asp Asp Asp Asp
225                 230                 235

<210> SEQ ID NO 13
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
                20                  25                  30

Val Ile Ser Trp Val Arg Gln Ala Pro Gly Gln Gly Leu Glu Trp Met
            35                  40                  45

Gly Gly Val Ile Pro Ile Val Asp Ile Ala Asn Tyr Ala Gln Arg Phe
        50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys

```
                    85                  90                  95
Ala Ser Thr Leu Gly Leu Val Leu Asp Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
            210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 14
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Ser Thr Leu Gly Leu Val Leu Asp Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
```

His Asn His Tyr Thr Gln Lys Ser Leu Ser Leu Ser Leu Gly Lys Asp
             435                 440                 445

Asp Asp Asp Asp Asp Asp Asp Asp
            450                 455

<210> SEQ ID NO 15
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Pro Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 16
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Asp Asp Asp Asp Asp Asp Asp Asp Gln Val Gln Leu Val Gln
1               5                   10                  15

Ser Gly Ala Glu Val Lys Lys Pro Gly Ser Ser Val Lys Val Ser Cys
                20                  25                  30

Lys Ala Ser Gly Tyr Thr Phe Ser Ser Asn Val Ile Ser Trp Val Arg

```
            35                  40                  45
Gln Ala Pro Gly Gln Gly Leu Glu Trp Met Gly Val Ile Pro Ile
 50                  55                  60

Val Asp Ile Ala Asn Tyr Ala Gln Arg Phe Lys Gly Arg Val Thr Ile
 65                  70                  75                  80

Thr Ala Asp Glu Ser Thr Ser Thr Tyr Met Glu Leu Ser Ser Leu
                 85                  90                  95

Arg Ser Glu Asp Thr Ala Val Tyr Tyr Cys Ala Ser Thr Leu Gly Leu
                100                 105                 110

Val Leu Asp Ala Met Asp Tyr Trp Gly Gln Gly Thr Leu Val Thr Val
            115                 120                 125

Ser Ser Ala Ser Thr Lys Gly Pro Ser Val Phe Pro Leu Ala Pro Cys
130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Lys Thr Tyr Thr Cys Asn Val Asp His Lys Pro Ser Asn Thr Lys Val
210                 215                 220

Asp Lys Arg Val Glu Ser Lys Tyr Gly Pro Pro Cys Pro Pro Cys Pro
225                 230                 235                 240

Ala Pro Glu Phe Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Glu Asp Pro Glu Val Gln Phe Asn Trp Tyr
        275                 280                 285

Val Asp Gly Val Glu Val His Asn Ala Lys Thr Lys Pro Arg Glu Glu
    290                 295                 300

Gln Phe Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Gly Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Gln Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Arg Leu Thr Val Asp Lys Ser Arg Trp Gln Glu Gly Asn Val
            420                 425                 430

Phe Ser Cys Ser Val Met His Glu Ala Leu His Asn His Tyr Thr Gln
        435                 440                 445

Lys Ser Leu Ser Leu Ser Leu Gly Lys
    450                 455
```

<210> SEQ ID NO 17
<211> LENGTH: 467
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 17

```
Asp Asp Asp Asp Asp Asp Asp Asp Asp Gln Val Gln Leu Val Gln
1               5                   10                  15

Ser Gly Ala Glu Val Lys Lys Pro Gly Ser Ser Val Lys Val Ser Cys
            20                  25                  30

Lys Ala Ser Gly Tyr Thr Phe Ser Ser Asn Val Ile Ser Trp Val Arg
        35                  40                  45

Gln Ala Pro Gly Gln Gly Leu Glu Trp Met Gly Gly Val Ile Pro Ile
    50                  55                  60

Val Asp Ile Ala Asn Tyr Ala Gln Arg Phe Lys Gly Arg Val Thr Ile
65                  70                  75                  80

Thr Ala Asp Glu Ser Thr Ser Thr Thr Tyr Met Glu Leu Ser Ser Leu
                85                  90                  95

Arg Ser Glu Asp Thr Ala Val Tyr Tyr Cys Ala Ser Thr Leu Gly Leu
            100                 105                 110

Val Leu Asp Ala Met Asp Tyr Trp Gly Gln Gly Thr Leu Val Thr Val
        115                 120                 125

Ser Ser Ala Ser Thr Lys Gly Pro Ser Val Phe Pro Leu Ala Pro Cys
130                 135                 140

Ser Arg Ser Thr Ser Glu Ser Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205

Lys Thr Tyr Thr Cys Asn Val Asp His Lys Pro Ser Asn Thr Lys Val
    210                 215                 220

Asp Lys Arg Val Glu Ser Lys Tyr Gly Pro Pro Cys Pro Pro Cys Pro
225                 230                 235                 240

Ala Pro Glu Phe Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser Gln Glu Asp Pro Glu Val Gln Phe Asn Trp Tyr
        275                 280                 285

Val Asp Gly Val Glu Val His Asn Ala Lys Thr Lys Pro Arg Glu Glu
    290                 295                 300

Gln Phe Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Gly Leu Pro Ser Ser Ile Glu Lys Thr Ile Ser Lys Ala Lys Gly Gln
            340                 345                 350

Pro Arg Glu Pro Gln Val Tyr Thr Leu Pro Pro Ser Gln Glu Glu Met
```

```
                355                 360                 365
Thr Lys Asn Gln Val Ser Leu Thr Cys Leu Val Lys Gly Phe Tyr Pro
            370                 375                 380
Ser Asp Ile Ala Val Glu Trp Glu Ser Asn Gly Gln Pro Glu Asn Asn
385                 390                 395                 400
Tyr Lys Thr Thr Pro Pro Val Leu Asp Ser Asp Gly Ser Phe Phe Leu
                405                 410                 415
Tyr Ser Arg Leu Thr Val Asp Lys Ser Arg Trp Gln Glu Gly Asn Val
            420                 425                 430
Phe Ser Cys Ser Val Met His Glu Ala Leu His Asn His Tyr Thr Gln
        435                 440                 445
Lys Ser Leu Ser Leu Ser Leu Gly Lys Asp Asp Asp Asp Asp Asp Asp
    450                 455                 460
Asp Asp Asp
465

<210> SEQ ID NO 18
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Asp Asp Asp Asp Asp Asp Asp Asp Glu Thr Val Leu Thr Gln
1               5                   10                  15
Ser Pro Gly Thr Leu Ser Leu Ser Pro Gly Glu Arg Ala Thr Leu Ser
            20                  25                  30
Cys Arg Ala Ser Gln Ser Leu Gly Ser Ser Tyr Leu Ala Trp Tyr Gln
        35                  40                  45
Gln Lys Pro Gly Gln Ala Pro Arg Leu Leu Ile Tyr Gly Ala Ser Ser
    50                  55                  60
Arg Ala Pro Gly Ile Pro Asp Arg Phe Ser Gly Ser Gly Ser Gly Thr
65                  70                  75                  80
Asp Phe Thr Leu Thr Ile Ser Arg Leu Glu Pro Glu Asp Phe Ala Val
                85                  90                  95
Tyr Tyr Cys Gln Gln Tyr Ala Asp Ser Pro Ile Thr Phe Gly Gln Gly
            100                 105                 110
Thr Arg Leu Glu Ile Lys Arg Thr Val Ala Ala Pro Ser Val Phe Ile
        115                 120                 125
Phe Pro Pro Ser Asp Glu Gln Leu Lys Ser Gly Thr Ala Ser Val Val
    130                 135                 140
Cys Leu Leu Asn Asn Phe Tyr Pro Arg Glu Ala Lys Val Gln Trp Lys
145                 150                 155                 160
Val Asp Asn Ala Leu Gln Ser Gly Asn Ser Gln Glu Ser Val Thr Glu
                165                 170                 175
Gln Asp Ser Lys Asp Ser Thr Tyr Ser Leu Ser Ser Thr Leu Thr Leu
            180                 185                 190
Ser Lys Ala Asp Tyr Glu Lys His Lys Val Tyr Ala Cys Glu Val Thr
        195                 200                 205
His Gln Gly Leu Ser Ser Pro Val Thr Lys Ser Phe Asn Arg Gly Glu
    210                 215                 220
Cys
225
```

```
<210> SEQ ID NO 19
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Asp Asp Asp Asp Asp Asp Asp Asp Asp
    210                 215                 220

Asp
225

<210> SEQ ID NO 20
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Asp Asp Asp Asp Asp Asp Asp Asp Glu Thr Val Leu Thr Gln
1               5                   10                  15

Ser Pro Gly Thr Leu Ser Leu Ser Pro Gly Glu Arg Ala Thr Leu Ser
            20                  25                  30

Cys Arg Ala Ser Gln Ser Leu Gly Ser Ser Tyr Leu Ala Trp Tyr Gln
        35                  40                  45

Gln Lys Pro Gly Gln Ala Pro Arg Leu Leu Ile Tyr Gly Ala Ser Ser
    50                  55                  60
```

```
Arg Ala Pro Gly Ile Pro Asp Arg Phe Ser Gly Ser Gly Thr
65              70                  75                  80

Asp Phe Thr Leu Thr Ile Ser Arg Leu Glu Pro Glu Asp Phe Ala Val
                85                  90                  95

Tyr Tyr Cys Gln Gln Tyr Ala Asp Ser Pro Ile Thr Phe Gly Gln Gly
            100                 105                 110

Thr Arg Leu Glu Ile Lys Arg Thr Val Ala Ala Pro Ser Val Phe Ile
        115                 120                 125

Phe Pro Pro Ser Asp Glu Gln Leu Lys Ser Gly Thr Ala Ser Val Val
130                 135                 140

Cys Leu Leu Asn Asn Phe Tyr Pro Arg Glu Ala Lys Val Gln Trp Lys
145                 150                 155                 160

Val Asp Asn Ala Leu Gln Ser Gly Asn Ser Gln Glu Ser Val Thr Glu
                165                 170                 175

Gln Asp Ser Lys Asp Ser Thr Tyr Ser Leu Ser Ser Thr Leu Thr Leu
            180                 185                 190

Ser Lys Ala Asp Tyr Glu Lys His Lys Val Tyr Ala Cys Glu Val Thr
        195                 200                 205

His Gln Gly Leu Ser Ser Pro Val Thr Lys Ser Phe Asn Arg Gly Glu
210                 215                 220

Cys Asp Asp Asp Asp Asp Asp Asp Asp
225                 230                 235

<210> SEQ ID NO 21
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65              70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190
```

```
Tyr Ala Cys Glu Val Thr His Gln Gly Leu Ser Ser Pro Val Thr Lys
            195                 200                 205

Ser Phe Asn Arg Gly Glu Cys Gly Gly Gly Ser Asp Asp Asp
    210                 215                 220

Asp Asp Asp Asp Asp Asp
225                 230

<210> SEQ ID NO 22
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Gly Ser Gly Gly Gly Gly
    210                 215                 220

Ser Asp Asp Asp Asp Asp Asp Asp Asp
225                 230                 235

<210> SEQ ID NO 23
<211> LENGTH: 1344
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
caggtgcagc tggtgcagtc tggggctgag gtgaagaagc ctgggtcctc ggtgaaggtc      60
```

-continued

| | |
|---|---|
| tcctgcaagg cttctggata caccttcagt agcaatgtta tcagctgggt gcgccaggcc | 120 |
| cctggacaag ggctcgagtg gatgggggg gtcatcccta ttgttgatat tgcgaactac | 180 |
| gcacagagat tcaagggcag agtcacgatt accgcggacg aatccactag tacaacttac | 240 |
| atggagttga gcagcctgag gtctgaggac acggccgtgt attactgtgc gagcacactt | 300 |
| ggtctcgtcc tggatgctat ggactactgg ggtcagggta cgttagtgac ggtctcgagt | 360 |
| gcttccacca agggcccatc cgtcttcccc ctggcgccct gctccaggag cacctccgag | 420 |
| agcacagccg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgacc gtgcctcca gcagcttggg cacgaagacc | 600 |
| tacacctgca acgtagatca caagcccagc aacaccaagg tcgacaagag agttgagtcc | 660 |
| aaatatggtc ccccatgccc accatgccca gcacctgagt tcctgggggg accatcagtc | 720 |
| ttcctgttcc cccaaaaacc caaggacact ctcatgatct cccggacccc tgaggtcacg | 780 |
| tgcgtggtgg tggacgtgag ccaggaagac cccgaggtcc agttcaactg gtacgtggat | 840 |
| ggcgtggagg tgcataatgc caagacaaaa ccgcgggagg agcagttcaa cagcacgtac | 900 |
| cgtgtggtca gcgtcctcac cgtcctgcac caggactggc tgaacggcaa ggagtacaag | 960 |
| tgcaaggtct ccaacaaagg cctcccgtcc tccatcgaga aaccatctc caaagccaaa | 1020 |
| gggcagcccc gagagccaca ggtgtacacc ctgcccccat cccaggagga gatgaccaag | 1080 |
| aaccaggtca gcctgacctg cctggtcaaa ggcttctacc ccagcgacat cgccgtggag | 1140 |
| tgggagagca atgggcagcc ggagaacaac tacaagacca cgcctcccgt gctggactcc | 1200 |
| gacggctcct tcttcctcta cagcaggcta accgtggaca gagcaggtg gcaggagggg | 1260 |
| aatgtcttct catgctccgt gatgcatgag gctctgcaca accactacac acagaagagc | 1320 |
| ctctccctgt ctctggggaa atga | 1344 |

<210> SEQ ID NO 24
<211> LENGTH: 1374
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

| | |
|---|---|
| gacgacgatg atgacgatga cgacgacgat caggtgcagc tggtgcagtc tggggctgag | 60 |
| gtgaagaagc ctgggtcctc ggtgaaggtc tcctgcaagg cttctggata caccttcagt | 120 |
| agcaatgtta tcagctgggt gcgccaggcc cctggacaag ggctcgagtg gatgggggg | 180 |
| gtcatcccta ttgttgatat tgcgaactac gcacagagat tcaagggcag agtcacgatt | 240 |
| accgcggacg aatccactag tacaacttac atggagttga gcagcctgag gtctgaggac | 300 |
| acggccgtgt attactgtgc gagcacactt ggtctcgtcc tggatgctat ggactactgg | 360 |
| ggtcagggta cgttagtgac ggtctcgagt gcttccacca agggcccatc cgtcttcccc | 420 |
| ctggcgccct gctccaggag cacctccgag agcacagccg ccctgggctg cctggtcaag | 480 |
| gactacttcc ccgaaccggt gacggtgtcg tggaactcag gcgccctgac cagcggcgtg | 540 |
| cacaccttcc cggctgtcct acagtcctca ggactctact ccctcagcag cgtggtgacc | 600 |
| gtgcctcca gcagcttggg cacgaagacc tacacctgca acgtagatca caagcccagc | 660 |
| aacaccaagg tcgacaagag agttgagtcc aaatatggtc ccccatgccc accatgccca | 720 |

| | |
|---|---|
| gcacctgagt tcctgggggg accatcagtc ttcctgttcc ccccaaaacc caaggacact | 780 |
| ctcatgatct cccggacccc tgaggtcacg tgcgtggtgg tggacgtgag ccaggaagac | 840 |
| cccgaggtcc agttcaactg gtacgtggat ggcgtggagg tgcataatgc caagacaaag | 900 |
| ccgcgggagg agcagttcaa cagcacgtac cgtgtggtca gcgtcctcac cgtcctgcac | 960 |
| caggactggc tgaacggcaa ggagtacaag tgcaaggtct ccaacaaagg cctcccgtcc | 1020 |
| tccatcgaga aaaccatctc caaagccaaa gggcagcccc gagagccaca ggtgtacacc | 1080 |
| ctgcccccat cccaggagga gatgaccaag aaccaggtca gcctgacctg cctggtcaaa | 1140 |
| ggcttctacc ccagcgacat cgccgtggag tgggagagca atgggcagcc ggagaacaac | 1200 |
| tacaagacca cgcctcccgt gctggactcc gacggctcct tcttcctcta cagcaggcta | 1260 |
| accgtggaca agagcaggtg gcaggagggg aatgtcttct catgctccgt gatgcatgag | 1320 |
| gctctgcaca accactacac acagaagagc ctctccctgt ctctggggaa atga | 1374 |

<210> SEQ ID NO 25
<211> LENGTH: 1374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

| | |
|---|---|
| caggtgcagc tggtgcagtc tggggctgag gtgaagaagc ctgggtcctc ggtgaaggtc | 60 |
| tcctgcaagg cttctggata caccttcagt agcaatgtta tcagctgggt gcgccaggcc | 120 |
| cctggacaag ggctcgagtg gatgggggggg gtcatcccta ttgttgatat tgcgaactac | 180 |
| gcacagagat tcaagggcag agtcacgatt accgcggacg aatccactag tacaacttac | 240 |
| atggagttga gcagcctgag gtctgaggac acggccgtgt attactgtgc gagcacactt | 300 |
| ggtctcgtcc tggatgctat ggactactgg ggtcaggta cgttagtgac ggtctcgagt | 360 |
| gcttccacca agggcccatc cgtcttcccc ctggcgccct gctccaggag cacctccgag | 420 |
| agcacagccg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgacc gtgccctcca gcagcttggg cacgaagacc | 600 |
| tacacctgca acgtagatca caagcccagc aacaccaagg tcgacaagag agttgagtcc | 660 |
| aaatatggtc ccccatgccc accatgccca gcacctgagt tcctgggggg accatcagtc | 720 |
| ttcctgttcc ccccaaaacc caaggacact ctcatgatct cccggacccc tgaggtcacg | 780 |
| tgcgtggtgg tggacgtgag ccaggaagac cccgaggtcc agttcaactg gtacgtggat | 840 |
| ggcgtggagg tgcataatgc caagacaaag ccgcgggagg agcagttcaa cagcacgtac | 900 |
| cgtgtggtca gcgtcctcac cgtcctgcac caggactggc tgaacggcaa ggagtacaag | 960 |
| tgcaaggtct ccaacaaagg cctcccgtcc tccatcgaga aaaccatctc caaagccaaa | 1020 |
| gggcagcccc gagagccaca ggtgtacacc ctgcccccat cccaggagga gatgaccaag | 1080 |
| aaccaggtca gcctgacctg cctggtcaaa ggcttctacc ccagcgacat cgccgtggag | 1140 |
| tgggagagca atgggcagcc ggagaacaac tacaagacca cgcctcccgt gctggactcc | 1200 |
| gacggctcct tcttcctcta cagcaggcta accgtggaca agagcaggtg gcaggagggg | 1260 |
| aatgtcttct catgctccgt gatgcatgag gctctgcaca accactacac acagaagagc | 1320 |
| ctctccctgt ctctggggaa agacgacgat gatgacgatg acgacgacga ttga | 1374 |

<210> SEQ ID NO 26
<211> LENGTH: 1404
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26

```
gacgacgatg atgacgatga cgacgacgat caggtgcagc tggtgcagtc tggggctgag      60
gtgaagaagc ctgggtcctc ggtgaaggtc tcctgcaagg cttctggata caccttcagt     120
agcaatgtta tcagctgggt gcgccaggcc cctggacaag gctcgagtg atgggggg       180
gtcatcccta ttgttgatat tgcgaactac gcacagagat tcaagggcag agtcacgatt     240
accgcggacg aatccactag tacaacttac atggagttga gcagcctgag gtctgaggac     300
acggccgtgt attactgtgc gagcacactt ggtctcgtcc tggatgctat ggactactgg     360
ggtcagggta cgttagtgac ggtctcgagt gcttccacca agggcccatc cgtcttcccc     420
ctggcgccct gctccaggag cacctccgag agcacagccg ccctgggctg cctggtcaag     480
gactacttcc ccgaaccggt gacggtgtcg tggaactcag cgccctgac cagcggcgtg      540
cacaccttcc cggctgtcct acagtcctca ggactctact ccctcagcag cgtggtgacc     600
gtgccctcca gcagcttggg cacgaagacc tacacctgca acgtagatca caagcccagc     660
aacaccaagg tcgacaagag agttgagtcc aaatatggtc ccccatgccc accatgccca     720
gcacctgagt tcctggggg accatcagtc ttcctgttcc ccccaaaacc caaggacact     780
ctcatgatct cccggacccc tgaggtcacg tgcgtggtgg tggacgtgag ccaggaagac     840
cccgaggtcc agttcaactg gtacgtggat ggcgtggagg tgcataatgc caagacaaag     900
ccgcgggagg agcagttcaa cagcacgtac cgtgtggtca gcgtcctcac cgtcctgcac     960
caggactggc tgaacggcaa ggagtacaag tgcaaggtct ccaacaaagg cctcccgtcc    1020
tccatcgaga aaaccatctc caaagccaaa gggcagcccc gagagccaca ggtgtacacc    1080
ctgcccccat cccaggagga gatgaccaag aaccaggtca gcctgacctg cctggtcaaa    1140
ggcttctacc ccagcgacat cgccgtggag tgggagagca atgggcagcc ggagaacaac    1200
tacaagacca cgcctcccgt gctggactcc gacggctcct tcttcctcta cagcaggcta    1260
accgtggaca gagcaggtg gcaggagggg aatgtcttct catgctccgt gatgcatgag    1320
gctctgcaca accactacac acagaagagc ctctccctgt ctctgggaa agacgacgat    1380
gatgacgatg acgacgacga ttga                                          1404
```

<210> SEQ ID NO 27
<211> LENGTH: 648
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27

```
gaaacggtac tcacgcagtc tccaggtacc ctgtctttgt ctccagggga aagagccacc      60
ctctcctgca gggccagtca gagtcttggc agcagctact agcctggta tcagcagaaa     120
cctggtcagg ctcccaggct cctcatctat ggtgcatcca gcagggcacc tggcatccca     180
gacaggttca gtggcagtgg gtctggtacc gacttcactc tcaccatcag ccgactggag     240
cctgaagatt ttgcagttta ttactgtcag cagtatgctg actcaccgat caccttcggc     300
```

```
caagggacac gactggagat taaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagacta cgagaaacac aaagtctacg cctgcgaagt cacccatcag    600
ggcctgagct cgcccgtcac aaagagcttc aacaggggag agtgttag                648
```

<210> SEQ ID NO 28
<211> LENGTH: 678
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 28

```
gacgacgatg atgacgatga cgacgacgat gaaacggtac tcacgcagtc tccaggtacc     60
ctgtctttgt ctccagggga agagccacc ctctcctgca gggccagtca gagtcttggc    120
agcagctact tagcctggta tcagcagaaa cctggtcagg ctcccaggct cctcatctat    180
ggtgcatcca gcagggcacc tggcatccca gacaggttca gtggcagtgg gtctggtacc    240
gacttcactc tcaccatcag ccgactggag cctgaagatt ttgcagttta ttactgtcag    300
cagtatgctg actcaccgat caccttcggc caagggacac gactggagat taaacgtacg    360
gtggctgcac catctgtctt catcttcccg ccatctgatg agcagttgaa atctggaact    420
gcctctgttg tgtgcctgct gaataacttc tatcccagag aggccaaagt acagtggaag    480
gtggataacg ccctccaatc gggtaactcc caggagagtg tcacagagca ggacagcaag    540
gacagcacct acagcctcag cagcaccctg acgctgagca agcagacta cgagaaacac    600 aaagtctacg cctgcgaagt cacccatcag ggcctgagct cgcccgtcac aaagagcttc    660
aacaggggag agtgttag                                                  678
```

<210> SEQ ID NO 29
<211> LENGTH: 678
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 29

```
gaaacggtac tcacgcagtc tccaggtacc ctgtctttgt ctccagggga agagccacc     60 ctctcctgca gggccagtca gagtcttggc agcagctact tagcctggta tcagcagaaa    120
cctggtcagg ctcccaggct cctcatctat ggtgcatcca gcagggcacc tggcatccca    180
gacaggttca gtggcagtgg gtctggtacc gacttcactc tcaccatcag ccgactggag    240
cctgaagatt ttgcagttta ttactgtcag cagtatgctg actcaccgat caccttcggc    300
caagggacac gactggagat taaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagacta cgagaaacac aaagtctacg cctgcgaagt cacccatcag    600
```

```
ggcctgagct cgcccgtcac aaagagcttc aacaggggag agtgtgacga cgatgatgac    660
gatgacgacg acgattag                                                  678

<210> SEQ ID NO 30
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
gacgacgatg atgacgatga cgacgacgat gaaacggtac tcacgcagtc tccaggtacc    60
ctgtctttgt ctccagggga aagagccacc ctctcctgca gggccagtca gagtcttggc   120
agcagctact tagcctggta tcagcagaaa cctggtcagg ctcccaggct cctcatctat   180
ggtgcatcca gcagggcacc tggcatccca gacaggttca gtggcagtgg gtctggtacc   240
gacttcactc tcaccatcag ccgactggag cctgaagatt ttgcagttta ttactgtcag   300
cagtatgctg actcaccgat caccttcggc caagggacac gactggagat taaacgtacg   360
gtggctgcac catctgtctt catcttcccg ccatctgatg agcagttgaa atctggaact   420
gcctctgttg tgtgcctgct gaataacttc tatcccagag aggccaaagt acagtggaag   480
gtggataacg ccctccaatc gggtaactcc caggagagtg tcacagagca ggacagcaag   540
gacagcacct acagcctcag cagcaccctg acgctgagca aagcagacta cgagaaacac   600
aaagtctacg cctgcgaagt cacccatcag ggcctgagct cgcccgtcac aaagagcttc   660
aacaggggag agtgtgacga cgatgatgac gatgacgacg acgattag               708

<210> SEQ ID NO 31
<211> LENGTH: 693
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gaaacggtac tcacgcagtc tccaggtacc ctgtctttgt ctccagggga aagagccacc    60
ctctcctgca gggccagtca gagtcttggc agcagctact tagcctggta tcagcagaaa   120
cctggtcagg ctcccaggct cctcatctat ggtgcatcca gcagggcacc tggcatccca   180
gacaggttca gtggcagtgg gtctggtacc gacttcactc tcaccatcag ccgactggag   240
cctgaagatt ttgcagttta ttactgtcag cagtatgctg actcaccgat caccttcggc   300
caagggacac gactggagat taaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca aagcagacta cgagaaacac aaagtctacg cctgcgaagt cacccatcag   600
ggcctgagct cgcccgtcac aaagagcttc aacaggggag agtgtggcgg aggcggcagc   660
gacgacgatg atgacgatga cgacgacgat tag                                693

<210> SEQ ID NO 32
<211> LENGTH: 708
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 32

```
gaaacggtac tcacgcagtc tccaggtacc ctgtctttgt ctccagggga aagagccacc    60
ctctcctgca gggccagtca gagtcttggc agcagctact tagcctggta tcagcagaaa   120
cctggtcagg ctcccaggct cctcatctat ggtgcatcca gcagggcacc tggcatccca   180
gacaggttca gtggcagtgg gtctggtacc gacttcactc tcaccatcag ccgactggag   240
cctgaagatt ttgcagttta ttactgtcag cagtatgctg actcaccgat caccttcggc   300
caagggacac gactggagat taaacgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagactac gagaaacaca aaagtctacg cctgcgaagt cacccatcag   600
ggcctgagct cgcccgtcac aaagagcttc aacaggggag agtgtggcgg aggcggcagc   660
ggcggaggcg gcagcgacga cgatgatgac gatgacgacg acgattag               708
```

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ser Asn Val Ile Ser
1               5

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Val Ile Pro Ile Val Asp Ile Ala Asn Tyr Ala Gln Arg Phe Lys
1               5                   10                  15
Gly

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Thr Leu Gly Leu Val Leu Asp Ala Met Asp Tyr
1               5                   10

<210> SEQ ID NO 36
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 36

Arg Ala Ser Gln Ser Leu Gly Ser Ser Tyr Leu Ala
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Ala Ser Ser Arg Ala Pro
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Gln Tyr Ala Asp Ser Pro Ile Thr
1               5

<210> SEQ ID NO 39
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Ser Thr Leu Gly Leu Val Leu Asp Ala Met Asp Tyr Trp Gly Gln
            100                 105                 110

Gly Thr Leu Val Thr Val Ser Ser
        115                 120

<210> SEQ ID NO 40
<211> LENGTH: 108
<212> TYPE: PRT
<213> ORGANISM: Artificial Sequence
<220> FEATURE:
<223> OTHER INFORMATION: Description of Artificial Sequence: Synthetic
```

-continued

```
        polypeptide

<400> SEQUENCE: 40

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys
                100                 105
```

BONE-TARGETING ANTIBODIES

CROSS REFERENCE TO RELATED APPLICATION

This application is a division of U.S. application Ser. No. 15/875,125, filed on Jan. 19, 2018, now U.S. Pat. No. 10,844,115, which claims priority from U.S. Provisional Application No. 62/448,763, filed on Jan. 20, 2017. The contents of the aforementioned priority applications are incorporated by reference herein in their entirety.

SEQUENCE LISTING

The instant application contains a Sequence Listing which has been filed electronically in ASCII format and is hereby incorporated by reference in its entirety. Said ASCII copy, created on Oct. 23, 2020, is named 022548_D1012_SL.txt and is 74,271 bytes in size.

FIELD OF THE INVENTION

The invention relates to antibodies modified with bone-targeting peptides and methods of their use for treating pathophysiological bone degeneration.

BACKGROUND OF THE INVENTION

Proper bone development and maintenance are important factors for normal health. In the average human, bone development occurs until the age of about 20 years old, where bone density is typically at its maximum. Thereafter, bone density can diminish without proper diet and physical exertion. Normal bone maintenance, however, requires homeostatic bone turnover, where old bone is removed and replaced with new bone.

Yet, there are numerous diseases and conditions that can affect bone development and maintenance. For example, bone development is affected in diseases such as osteogenesis imperfecta, where bone strength is compromised, which leads to children with fragile bones that can easily break. Moreover, lack of homeostatic bone turnover can occur in otherwise healthy individuals as they age, leading to osteoporosis, where bone density is compromised over time, and ultimately to fragile bones and bone fractures.

Still further, there are certain diseases wherein bone health is affected collaterally to the primary disease and involved in other comorbid sequelae, such as in chronic kidney disease (CKD). CKD is a progressive disease in which kidney function declines over time, often leading to cardiovascular diseases linked to poor bone health and altered bone turnover rates. It has been shown that treatments that improve bone health concomitantly alleviate the associated cardiovascular diseases. Such reports suggest that normal bone turnover rates could be influential on, if not causative of, other diseases. Therefore, improved methodologies for regulating bone development and/or maintenance could have a widespread direct or indirect effect on improving the health of individuals suffering from numerous disparate diseases and conditions.

TGFβ is a member of the transforming growth factor-beta (TGFβ) superfamily and is important in bone formation during mammalian development (see Chen et al., Int. J. Biol. Sci. 8(2): 272-88 (2012)). TGFβ appears to be equally important for homeostatic bone maintenance. Interestingly, TGFβ has been shown to be expressed at higher levels in individuals with CKD, suggesting that it is a viable target for therapeutic intervention. Systemic treatment of a jck mouse model of CKD with anti-TGFβ antibodies demonstrated a reduction in high bone turnover rates (Liu et al., J. Bone Miner Res. 29(5): 1141-57 (2014)). However, this study did not investigate the degree to which localization of the anti-TGFβ antibodies in bone may improve treatment efficacy. Given that TGFβ is involved in a multitude of cellular processes including DNA damage response, allergic immune responses, and wound epithelialization, just to name a few, a more targeted approach for controlling TGFβ activity is desirable to minimize potential undesired side-effects. Therefore, a more precise approach for regulating TGFβ activity is needed to provide improved treatments for regulating bone development and/or maintenance.

SUMMARY OF THE INVENTION

Provided herein are antibodies, such as anti-TGFβ antibodies, that are effectively targeted to bone. In a first aspect, the present disclosure provides an antibody, or an antigen-binding fragment thereof, comprising a heavy chain, a light chain, and one or more poly-aspartate (poly-D) peptides. In one particular embodiment, the antibody or antigen-binding fragment comprises a heavy chain, a light chain, and one or more poly-aspartate (poly-D) peptides connected to the heavy chain and/or the C-terminus of the light chain.

In one embodiment, the antibody or antigen-binding fragment thereof exhibits at least a 2-fold increase in localization to bone compared to an antibody with the same heavy chain and light chain but lacking the one or more poly-D peptides.

In one embodiment, the one or more poly-D peptides are connected to the antibody or antigen-binding fragment thereof by chemical conjugation. In another embodiment, the one or more poly-D peptides are connected at the hinge region of the heavy chain. In a further embodiment, the one or more poly-D peptides are connected to the N-terminus or C-terminus of the light chain. In a still further embodiment, the one or more poly-D peptides are connected to the antibody or antigen-binding fragment thereof by one or more spacers/linkers (e.g., polyethylene glycol (PEG) spacers and peptide linkers).

In one embodiment, one or more poly-D peptides are integral with an amino acid sequence of the heavy chain and/or one or more poly-D peptides are integral with an amino acid sequence of the light chain. A poly-D peptide that is "integral" with an amino acid sequence is included in the same polypeptide chain. For example the integral poly-D peptide can be translated from the same RNA chain as the heavy or light chain sequence, which may be encoded from a recombinant DNA plasmid. In one embodiment, one or more poly-D peptides are integral with the N-terminus and/or one or more poly-D peptides are integral with the C-terminus of the heavy chain. Two or more poly-D peptides can be linked in tandem, separated by zero, one or more other amino acid residues (i.e., non-aspartate amino acids) or a peptide linker to the N-terminus or the C-terminus of the heavy chain. In a further embodiment, one or more poly-D peptides are integral with the N-terminus and/or one or more poly-D peptides are integral with the C-terminus of the light chain. For example, two or more poly-D peptides can be linked in tandem being separated by zero, one or more other amino acid residues (i.e., non-aspartate amino acids) or a peptide linker to the N-terminus or the C-terminus of the light chain. In one embodiment, a poly-D peptide is integral with the C-terminus of the heavy chain. In another embodiment, a poly-D peptide is integral with the C-terminus of the heavy chain and a poly-D peptide is integral with the N-terminus of the heavy chain.

In one embodiment, the light chain does not comprise a poly-D peptide. In another embodiment, the heavy chain does not comprise a poly-D peptide.

In one embodiment, the one or more poly-D peptides each independently comprise 2-30 aspartic acid residues. For example, a poly-D peptide can include 2, or 3, or 4, or 5, or 6, or 7, or 8, or 9, or 10, or 11, or 12, or 13, or 14, or 15, or 16, or 17, or 18, or 19, or 20, or 21, or 22, or 23, or 24, or 25, or 26, or 27, or 28, or 29, or 30 aspartic acid residues. In another embodiment, the one or more poly-D peptides each independently comprise 6, 7, 8, 9, 10 or 11 aspartic acid residues. In another embodiment, the one or more poly-D peptides each comprise 10 aspartic acid residues, such peptides are called "D10" (SEQ ID NO: 1) herein. In some embodiments, the antibody or fragment may include 1, 2, 3, 4, 5, 6, 7, 8, 9, 10, 11, 12, or more than 12 poly-D peptides.

In another embodiment, the antibody is any of isotypes $IgG_1$, $IgG_2$, $IgG_3$, $IgG_4$, $IgA_1$, $IgA_2$, IgM, IgE, or IgD. In another embodiment, the antibody is an $IgG_1$ or $IgG_4$ isotype. In another embodiment, the antibody or antigen-binding fragment thereof specifically binds one or more of TGFβ1, TGFβ2, and TGFβ3, such as one or more of human TGFβ1, TGFβ2, and TGFβ3.

In one embodiment, an antibody fragment is contemplated having one or more poly-aspartate (poly-D) peptides. It is envisioned that the antibody fragment would exhibit at least a 2-fold increase in localization to bone compared to the same antibody fragment but lacking the one or more poly-D peptides. The antibody fragment can, for example, be any or a combination of the following: Fab, F(ab')$_2$, monospecific Fab$_2$, bispecific Fab$_2$, trispecific Fab, monovalent IgG, scFv, bispecific diabody, trispecific triabody, scFv-sc, a minibody, IgNAR, V-NAR, hcIgG, or VhH. In one embodiment, the antibody fragment binds one or more of TGFβ1, TGFβ2, and TGFβ3, such as one or more of human TGFβ1, TGFβ2, and TGFβ3. The antibody or antibody fragment herein may be fully human, humanized, or chimeric.

In a second aspect, the present disclosure provides a method of producing an antibody or an antigen-binding fragment thereof targeted to bone that includes the steps of providing an antibody heavy chain, providing an antibody light chain, providing one or more poly-D peptides attached to the heavy chain and/or one or more poly-D peptides attached to the light chain, and combining the heavy chain and the light chain to produce an antibody or antigen-binding fragment thereof targeted to bone.

In one embodiment, the one or more poly-D peptides attached to the heavy chain and/or the one or more poly-D peptides attached to the light chain are attached by chemical conjugation. In another embodiment, the one or more poly-D peptides attached to the heavy chain and/or the one or more poly-D peptides attached to the light chain are attached by recombination.

In a third aspect, the present disclosure provides an anti-TGFβ antibody targeted to bone that includes a heavy chain comprising an amino acid sequence set forth in any of SEQ ID NOS: 2, 3 4, and 5 (with or without the heavy chain C-terminal lysine), and a light chain comprising an amino acid sequence set forth in any of SEQ ID NOS: 6, 7, 8, 11, and 12, with the proviso that the heavy chain amino acid sequence is not SEQ ID NO: 2 (with or without the heavy chain C-terminal lysine) when the light chain amino acid sequence is SEQ ID NO: 6.

In a fourth aspect, the present disclosure provides an anti-TGFβ antibody targeted to bone that includes a heavy chain comprising an amino acid sequence set forth in any of SEQ ID NOS: 13, 14, 16, and 17 (with or without the heavy chain C-terminal lysine), and a light chain comprising an amino acid sequence set forth in any of SEQ ID NOS: 15, 18, 19, 20, 21, and 22, with the proviso that the heavy chain amino acid sequence is not SEQ ID NO: 13 (with or without the heavy chain C-terminal lysine) when the light chain amino acid sequence is SEQ ID NO: 15.

In a fifth aspect, the present disclosure provides a human $IgG_4$ antibody that includes a heavy chain comprising the amino acid sequence of SEQ ID NO: 14 (with or without the heavy chain C-terminal lysine) and a light chain comprising the amino acid sequence of SEQ ID NO: 15 (e.g., mAb2 F6). The antibody specifically binds one or more of TGFβ1, TGFβ2, and TGFβ3. In one embodiment, the antibody specifically binds TGFβ1.

In a sixth aspect, the present disclosure provides a human $IgG_4$ antibody that includes a heavy chain comprising the amino acid sequence of SEQ ID NO: 17 (with or without the heavy chain C-terminal lysine), and a light chain comprising the amino acid sequence of SEQ ID NO: 15 (e.g., mAb2 F16). The antibody specifically binds one or more of TGFβ1, TGFβ2, and TGFβ3. In one embodiment, the antibody specifically binds TGFβ1.

In a seventh aspect, the present disclosure provides a human $IgG_4$ antibody that includes a heavy chain comprising the amino acid sequence of SEQ ID NO: 16 (with or without the heavy chain C-terminal lysine), and a light chain comprising the amino acid sequence of SEQ ID NO: 15 (e.g., mAb2 F11). The antibody specifically binds one or more of TGFβ1, TGFβ2, and TGFβ3. In one embodiment, the antibody specifically binds TGFβ1.

In an eighth aspect, the present disclosure provides a human $IgG_4$ antibody that includes a heavy chain comprising the amino acid sequence of SEQ ID NO: 17 (with or without the heavy chain C-terminal lysine), and a light chain comprising the amino acid sequence of SEQ ID NO: 18 (e.g., mAb2 F17). The antibody specifically binds one or more of TGFβ1, TGFβ2, and TGFβ3. In one embodiment, the antibody specifically binds TGFβ1.

In a ninth aspect, the present disclosure provides a human $IgG_4$ antibody that includes a heavy chain comprising the amino acid sequence of SEQ ID NO: 16 (with or without the heavy chain C-terminal lysine), and a light chain comprising the amino acid sequence of SEQ ID NO: 18 (e.g., mAb2 F12). The antibody specifically binds one or more of TGFβ1, TGFβ2, and TGFβ3. In one embodiment, the antibody specifically binds TGFβ1.

In a tenth aspect, the present disclosure provides a human $IgG_4$ antibody that includes a heavy chain comprising the amino acid sequence of SEQ ID NO: 14 (with or without the heavy chain C-terminal lysine), and a light chain comprising the amino acid sequence of SEQ ID NO: 18 (e.g., mAb2 F7). The antibody specifically binds one or more of TGFβ1, TGFβ2, and TGFβ3. In one embodiment, the antibody specifically binds TGFβ1.

In an eleventh aspect, the present disclosure provides a human $IgG_4$ antibody that includes a heavy chain comprising the amino acid sequence of SEQ ID NO: 13 (with or without the heavy chain C-terminal lysine), and a light chain comprising the amino acid sequence of SEQ ID NO: 18 (e.g., mAb2 F2). The antibody specifically binds one or more of TGFβ1, TGFβ2, and TGFβ3. In one embodiment, the antibody specifically binds TGFβ1.

In a twelfth aspect, the present disclosure provides an anti-TGFβ antibody targeted to bone including a heavy chain comprising an amino acid sequence encoded by a nucleic acid sequence in set forth in any of SEQ ID NOS: 23, 24, 25, and 26 (with or without the codon for the heavy chain C-terminal lysine) and a light chain comprising an amino acid sequence encoded by a nucleic acid sequence in set forth in any of SEQ ID NOS: 27, 28, 29, 30, 31, and 32, with the proviso that the heavy chain amino acid sequence is not encoded by the nucleic acid sequence set forth in SEQ ID NO: 23 (with or without the codon for the heavy chain C-terminal lysine) when the light chain amino acid sequence is encoded by the nucleic acid sequence in set forth in SEQ ID NO: 27.

In a thirteenth aspect, the present disclosure provides a human IgG₄ antibody including a heavy chain comprising an amino acid sequence encoded by the nucleic acid sequence set forth in SEQ ID NO: 25 (with or without the codon for the heavy chain C-terminal lysine) and a light chain comprising an amino acid sequence encoded by the nucleic acid sequence set forth in SEQ ID NO: 27. The antibody specifically binds one or more of TGFβ1, TGFβ2, and TGFβ3.

In a fourteenth aspect, the present disclosure provides a human IgG₄ antibody including a heavy chain comprising an amino acid sequence encoded by the nucleic acid sequence set forth in SEQ ID NO: 26 (with or without the codon for the heavy chain C-terminal lysine) and a light chain comprising an amino acid sequence encoded by the nucleic acid sequence set forth in SEQ ID NO: 27. The antibody specifically binds one or more of TGFβ1, TGFβ2, and TGFβ3.

In a fifteenth aspect, the present disclosure provides a method for treating an individual for bone loss including administering to the individual an effective amount of an anti-TGFβ antibody or an antigen-binding fragment thereof targeted to bone and detecting at least one of a reduction in TGFβ levels, a reduction in TGFβ activity, a reduction in bone loss, a reduction in rate of bone loss, an increase in bone density, an increase in bone strength, and a reduction in IL-11 levels.

In one embodiment, the individual is a human. In another embodiment, the anti-TGFβ antibody or antibody fragment specifically binds one or more of TGFβ1, TGFβ2, and TGFβ3. In a further embodiment, the anti-TGFβ antibody includes a heavy chain, a light chain, and one or more poly-aspartate (poly-D) peptides. The antibody exhibits at least a 2-fold increase in localization to bone compared to an antibody with the same heavy chain and light chain but lacking the one or more poly-D peptides. In one embodiment, the antibody is any of isotypes IgG₁, IgG₂, IgG₃, IgG₄, IgA₁, IgA₂, IgM, IgE, and IgD. In another embodiment, the antibody is an IgG₁ or IgG₄ isotype. In one embodiment, the individual has chronic kidney disease and/or a bone disease, including metastasis of cancer to bone. The bone disease can be osteogenesis imperfecta or osteoporosis. In one embodiment, the effective amount of the anti-TGFβ antibody or antibody fragment targeted to bone is administered subcutaneously, intravenously, or intramuscularly.

In a sixteenth aspect, the present disclosure provides a pharmaceutical composition comprising an antibody or antigen-binding fragment of the present invention and a pharmaceutically acceptable carrier. For example, the antibody may include a heavy chain comprising an amino acid sequence set forth in any of SEQ ID NOS: 2, 3, 4, and 5 (with or without the heavy chain C-terminal lysine) and a light chain comprising an amino acid sequence set forth in any of SEQ ID NOS: 6, 7, 8, 11, and 12, with the proviso that the heavy chain amino acid sequence is not SEQ ID NO: 2 (with or without the heavy chain C-terminal lysine) when the light chain amino acid sequence is SEQ ID NO: 6. In another embodiment, the antibody may include a heavy chain comprising an amino acid sequence set forth in any of SEQ ID NOS: 13, 14, 16, and 17 (with or without the heavy chain C-terminal lysine); and a light chain comprising an amino acid sequence set forth in any of SEQ ID NOS: 15, 18, 19, 29, 21, and 22, with the proviso that the heavy chain amino acid sequence is not SEQ ID NO: 13 (with or without the heavy chain C-terminal lysine) when the light chain amino acid sequence is SEQ ID NO: 15.

In an seventeenth aspect, the present disclosure provides an isolated nucleic acid molecule including a nucleic acid sequence encoding the heavy chain, the light chain, or both, of an anti-TGFβ antibody targeted to bone, wherein the heavy chain of the anti-TGFβ antibody comprises an amino acid sequence set forth in any of SEQ ID NOS: 13, 14, 16, and 17 (with or without the heavy chain C-terminal lysine) and the light chain of the anti-TGFβ antibody comprises an amino acid sequence set forth in any of SEQ ID NOS: 15, 18, 19, 20, 21, and 22, with the proviso that the heavy chain amino acid sequence is not SEQ ID NO: 13 (with or without the heavy chain C-terminal lysine) when the light chain amino acid sequence is SEQ ID NO: 15.

In an eighteenth aspect, the present disclosure provides an expression vector including a nucleic acid sequence encoding the heavy chain, the light chain, or both, of an anti-TGFβ antibody targeted to bone, wherein the heavy chain of the anti-TGFβ antibody comprises an amino acid sequence set forth in any of SEQ ID NOS: 13, 14, 16, and 17 (with or without the heavy chain C-terminal lysine); and the light chain of the anti-TGFβ antibody comprises an amino acid sequence set forth in any of SEQ ID NOS: 15, 18, 19, 20, 21, and 22, with the proviso that the heavy chain amino acid sequence is not SEQ ID NO: 13 (with or without the heavy chain C-terminal lysine) when the light chain amino acid sequence is SEQ ID NO: 15.

In a nineteenth aspect, the present disclosure provides a host cell comprising one or more expression vectors including nucleic acid sequences encoding an anti-TGFβ antibody targeted to bone, wherein the heavy chain of the anti-TGFβ antibody comprises a heavy chain comprising an amino acid sequence set forth in any of SEQ ID NOS: 13, 14, 16, and 17 (with or without the heavy chain C-terminal lysine); and a light chain comprising an amino acid sequence set forth in any of SEQ ID NOS: 15, 18, 19, 29, 21, and 22, with the proviso that the heavy chain amino acid sequence is not SEQ ID NO: 13 (with or without the heavy chain C-terminal lysine) when the light chain amino acid sequence is SEQ ID NO: 15. In one embodiment, the host cell is a mammalian cell or a prokaryotic cell. In another embodiment, the host cell is a Chinese Hamster Ovary (CHO) cell or an *Escherichia coli* (*E. coli*) cell.

In a twentieth aspect, the present disclosure provides a method of producing an anti-TGFβ antibody or an antigen-binding fragment thereof targeting bone. The method includes growing a host cell under conditions permitting production of the antibody or antigen-binding fragment thereof. The host cell comprises (i) a nucleic acid sequence encoding a heavy chain comprising an amino acid sequence set forth in any of SEQ ID NOS: 13, 14, 16, and 17 (with or without the heavy chain C-terminal lysine); and (ii) a nucleic acid sequence encoding a light chain comprising an amino acid sequence set forth in any of SEQ ID NOS: 15, 18, 19, 29, 21, and 22, with the proviso that the heavy chain amino acid sequence is not SEQ ID NO: 13 (with or without the heavy chain C-terminal lysine) when the light chain amino acid sequence is SEQ ID NO: 15. In one embodiment, the method further includes formulating the antibody or antigen-binding fragment thereof as a pharmaceutical composition comprising an acceptable carrier.

In a twenty-first aspect, the present disclosure provides a pharmaceutical composition comprising an anti-TGFβ antibody targeted to bone. The anti-TGFβ antibody targeted to bone includes a heavy chain comprising an amino acid sequence set forth in any of SEQ ID NOS: 2, 3, 4, and 5 (with or without the heavy chain C-terminal lysine) and a light chain comprising an amino acid sequence set forth in any of SEQ ID NOS: 6, 7, 8, 11, and 12, with the proviso that the heavy chain amino acid sequence is not SEQ ID NO: 2 (with or without the heavy chain C-terminal lysine) when the light chain amino acid sequence is SEQ ID NO: 6, or the anti-TGFβ antibody targeted to bone includes a heavy chain comprising an amino acid sequence set forth in any of SEQ ID NOS: 13, 14, 16, and 17 (with or without the heavy chain C-terminal lysine); and a light chain comprising an amino acid sequence set forth in any of SEQ ID NOS: 15, 18, 19, 29, 21, and 22, with the proviso that the heavy chain amino acid sequence is not SEQ ID NO: 13 (with or without the heavy chain C-terminal lysine) when the light chain amino acid sequence is SEQ ID NO: 15. In one embodiment, the pharmaceutical composition is formulated as a liquid drug product. In another embodiment, the pharmaceutical composition is formulated as a lyophilized drug product.

In a twenty-second aspect, the present disclosure provides an anti-TGFβ antibody targeted to bone. The heavy chain of the antibody comprises: a heavy chain complementarity-determining region 1 (HCDR1) comprising the amino acid sequence of SEQ ID NO: 33, an HCDR2 comprising the amino acid sequence of SEQ ID NO:34, and an HCDR3 comprising the amino acid sequence of SEQ ID NO: 35. The light chain of the antibody comprises: a light chain complementarity-determining region 1 (LCDR1) comprising the amino acid sequence of SEQ ID NO: 36, an LCDR2 comprising the amino acid sequence of SEQ ID NO: 37, and an LCDR3 comprising the amino acid sequence of SEQ ID NO: 38. And, the antibody further comprises a D10 polypeptide at one of more of the N terminus of the heavy chain, the C terminus of the heavy chain, the N terminus of the light chain, and the C terminus of the light chain.

In a twenty-third aspect, the present disclosure provides an anti-TGFβ antibody targeted to bone, wherein the heavy chain of the antibody comprises the heavy chain complementarity-determining regions (CDR) 1-3 in SEQ ID NO: 39 and the light chain CDR1-3 in SEQ ID NO: 40, wherein the antibody further comprises a D10 polypeptide at one of more of the N terminus of the heavy chain, the C terminus of the heavy chain, the N terminus of the light chain, and the C terminus of the light chain. In some embodiments, the antibody comprises a heavy chain variable domain ($V_H$ or HCVD) comprising the amino acid sequence of SEQ ID NO: 39 and a light chain variable domain ($V_L$ or LCVD) comprising the amino acid sequence of SEQ ID NO: 40.

In a twenty-fourth aspect, the present disclosure provides a polynucleotide sequence encoding: an anti-TGFβ antibody targeted to bone, wherein the heavy chain of the antibody comprises an HCDR1 comprising the amino acid sequence of SEQ ID NO: 33, an HCDR2 comprising the amino acid sequence of SEQ ID NO: 34, and an HCDR3 comprising the amino acid sequence of SEQ ID NO: 35, the light chain of the antibody comprises an LCDR1 comprising the amino acid sequence of SEQ ID NO: 36, an LCDR2 comprising the amino acid sequence of SEQ ID NO: 37, and an LCDR3 comprising the amino acid sequence of SEQ ID NO: 38, and the antibody further comprises a D10 polypeptide at one of more of the N terminus of the heavy chain, the C terminus of the heavy chain, the N terminus of the light chain, and the C terminus of the light chain; or an anti-TGFβ antibody targeted to bone, wherein the heavy chain of the antibody comprises the heavy chain complementarity-determining regions (CDR) 1-3 in SEQ ID NO: 39 and the light chain CDR1-3 in SEQ ID NO: 40, wherein the antibody further comprises a D10 polypeptide at one of more of the N terminus of the heavy chain, the C terminus of the heavy chain, the N terminus of the light chain, and the C terminus of the light chain.

In a twenty-fifth aspect, the present disclosure provides a bone-targeting antibody, such as a bone-targeting anti-TGFβ antibody or antigen-binding fragment, of the present invention for use in a treatment method described herein.

In a twenty-sixth aspect, the disclosure provides the use of a bone-targeting antibody, such as a bone targeting anti-TGFβ antibody or antigen-binding fragment, of the present invention, for the manufacture of a medicament for a treatment method described herein.

Particular embodiments contemplated herein are further described below. The above-described and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF DRAWINGS

FIG. 4A depicts the SEC profile of the chemical conjugate of D10 peptide with mAb1. FIG. 4B depicts the SEC profile of a 1:1 molar mixture of the mAb1-D10 chemical conjugate with TGFβ1. FIG. 4C depicts the SEC profile of unmodified mAb1. FIG. 4D depicts the SEC profile of a 1:1 molar mixture of mAb1 with TGFβ1. FIG. 4E depicts the SEC profile of Herceptin®. FIG. 4F depicts the SEC profile of a chemical conjugate of D10 peptide with Herceptin®. FIG. 4G depicts the SEC profile of the chemical conjugate of D10 with Herceptin® mixed in a 1:1 ratio with TGFβ1.

DETAILED DESCRIPTION OF THE INVENTION

Figure 1:
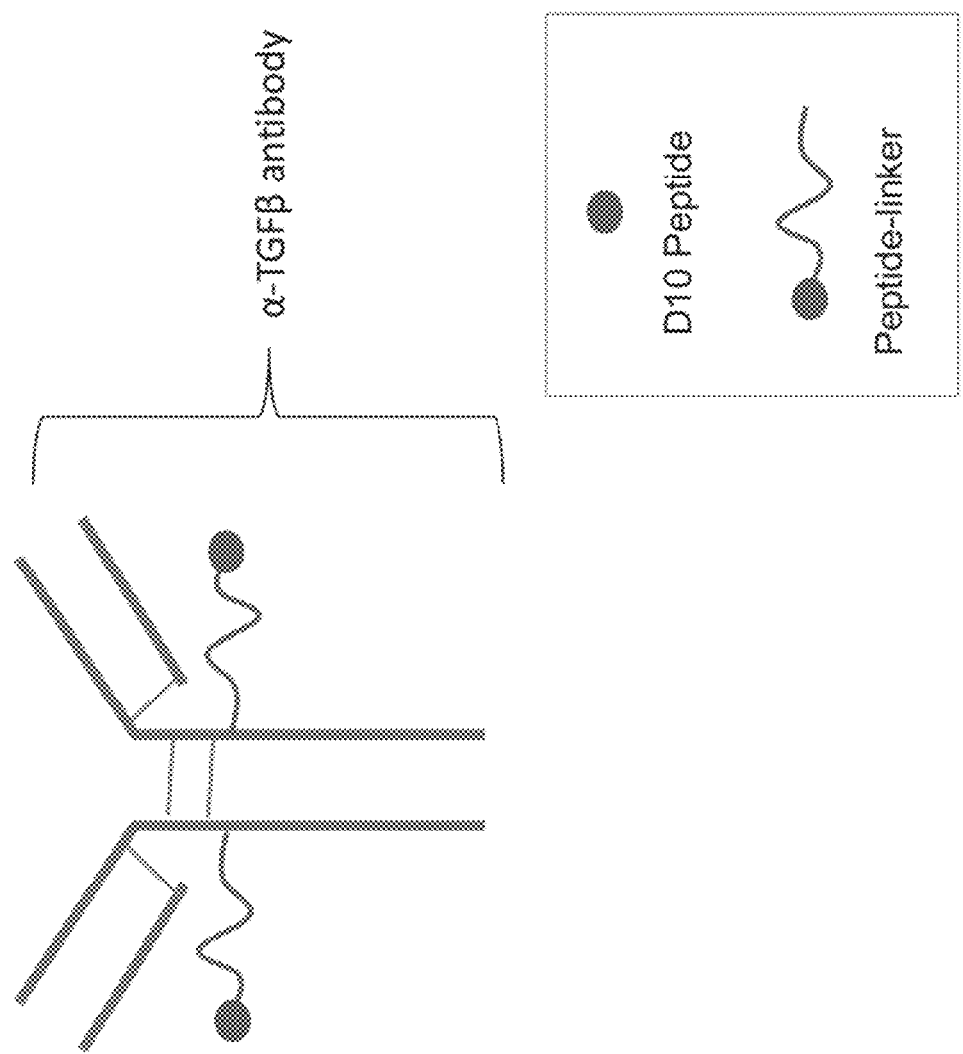
FIG. 1 depicts a D10 peptide chemically conjugated to an anti-TGFβ (α-TGFβ) antibody.

The present invention provides antibodies and antigen-binding fragments thereof that are connected to one or more bone-targeting poly-D peptides such that the antibodies and fragments preferentially home to the bones in a patient in need thereof. The bone-targeting feature of such an antibody or fragment allows the antibody and fragment to target bone tissues specifically and reduces the patient's systemic exposure to the antibody or fragment, thereby enhancing the efficacy of the drug while minimizing undesired adverse side effects.

As used herein, the term "poly-D peptide" refers to a peptide sequence having a plurality of aspartic acid or aspartate or "D" amino acids, such as about 2, 3, 4, 5, 6, 7, 8, 9, 10, 20, 30, or more aspartic acid amino acids (residues). In one embodiment, a poly-D peptide can include about 2 to about 30, or about 3 to about 15, or about 4 to about 12, or about 5 to about 10, or about 6 to about 8, or about 7 to about 9, or about 8 to about 10, or about 9 to about 11, or about 12 to about 14 aspartic acid residues. In one embodiment, poly-D peptides include only aspartate residues. In another embodiment, poly-D peptides may include one or more other amino acids or similar compounds. As used herein, the term "D10" refers to a contiguous sequence of ten aspartic acid amino acids, as seen in SEQ ID NO: 1. In some embodiments, an antibody or antibody fragment of the invention may include 1, 2, 3, 4, 5, 6, 7, 8, 9, 10, 11, 12, or more than 12 poly-D peptides.

The poly-D peptide can be connected to an antibody or antigen-binding fragment of interest via recombinant technology or chemical conjugation. As used herein, the term "fusion variant" or "variant" refers to an assembled antibody construct (see FIG. 9B) that includes at least one of a heavy chain or a light chain or antibody fragment or subpart that incorporates or is otherwise associated with a poly-D peptide, such as a D10 sequence. For example, a poly-D peptide can be connected to an antibody chain in a fusion variant by recombinant technology (e.g., where a poly-D peptide sequence is integral with the amino acid sequence of the heavy chain, light chain, or antibody fragment or subpart), chemical conjugation, or both.

As used herein, the term "chemical conjugate" refers to an assembled antibody that includes at least one of a heavy chain or a light chain or antibody fragment or subpart to which one or more poly-D peptides are connected by chemical reaction with, for example, the cysteine residues present in the amino acid sequence of the heavy chain, light chain, antibody fragment, or subpart. Exemplary cysteine residues that can be used for conjugation are those in the heavy chain hinge region. Cysteine residues or other residues appropriate for conjugation can also be introduced to the antibody chain by mutagenesis. A spacer/linker such as a peptide linker or a chemical moiety (e.g., a maleimide function group and a polyethylene glycol (PEG)) may be used between the poly-D peptide and the antibody component in the conjugation. Methods for chemical conjugation of desired moieties to antibodies are well known in the art. See, e.g., Behrens and Liu, mAbs 6:1, 46-53 (2014).

As used herein, the term "integral" refers to the integration of a poly-D peptide with an antibody chain via recombinant technology such that the poly-D peptide is transcribed from the same RNA transcript as the antibody chain and resides in the same polypeptide sequence as the antibody chain. In such cases, the poly-D peptide can be connected to the antibody chain, with or without any peptide linker or amino acid spacer, at the antibody chain's either or both termini, or integrated internally to the antibody chain, without affecting the antibody chain's proper folding, the antibody molecule's assembly, or the antibody's binding to its antigen.

Figure 9A:
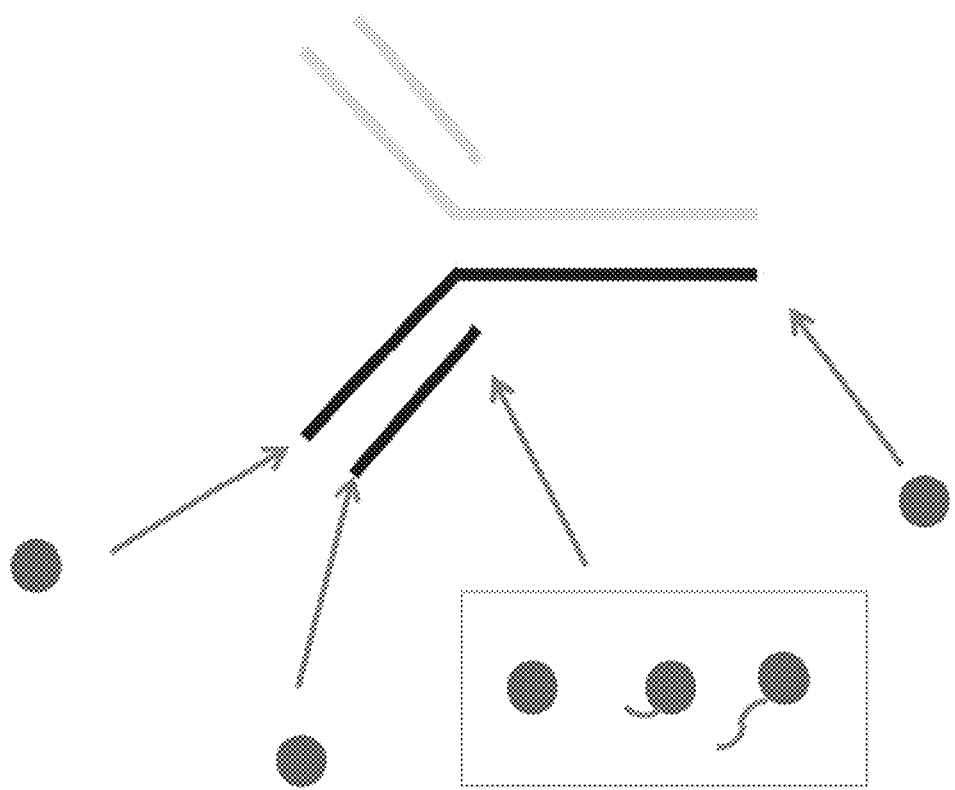
FIG. 9A diagrammatically depicts possible locations of D10 peptides on an IgG subtype antibody for creating a series of mAb1 fusion variant antibodies to be obtained by attachment of D10 peptides to the heavy and/or light chain termini using recombinant methods. The sites of addition of D10 peptides are indicated by the circles and the use of peptide linker sequences is indicated by wavy lines (the longer wavy line represents a longer linker than the shorter wavy line).
Figure 9A:
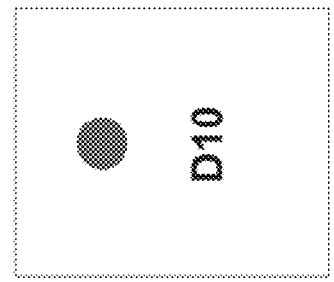
Figure 9B:
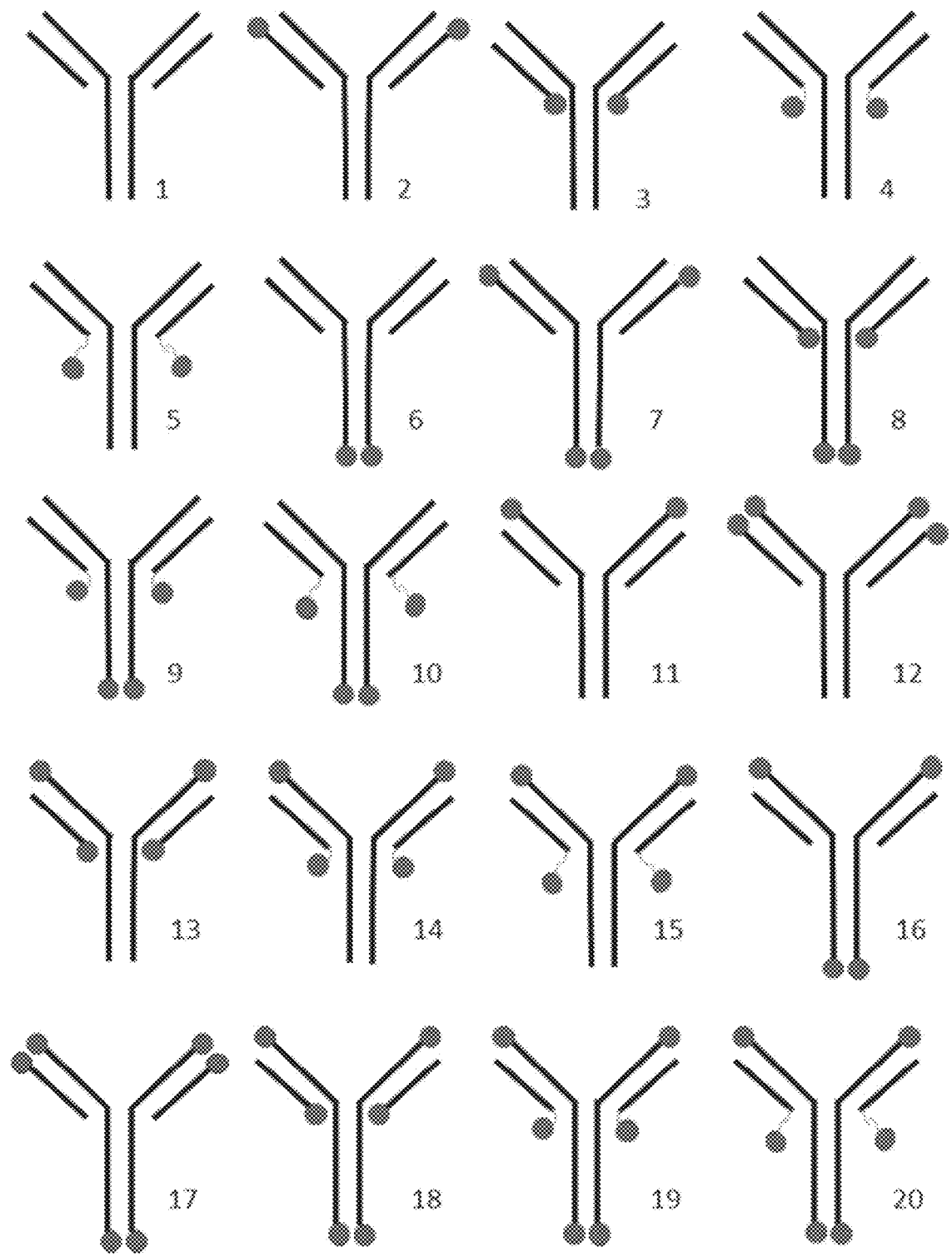
FIG. 9B depicts a series of fusion variant antibodies (fusion variants) derived by placement of the peptides, as shown in FIG. 9A. Recombinant fusion variants with various combinations of the position of attachment and peptide numbers were generated. The smaller numbers below each diagram depict the identity of each recombinant fusion variant as referred to herein for the sake of clarity. As referred to herein, fusion variants are designated either with "fusion" or "F" followed by the intended variant number. For example, "Fusion 1" and "F1" both refer to an antibody having the configuration of the antibody "1" without a D10 peptide. The longer wavy line represents a longer linker than the shorter wavy line.

Exemplary formats of the bone-targeting antibodies of the present invention are shown in FIG. 9B (formats F2-F20). The bone-targeting peptide (represented by circles) can be attached or fused to (e.g., integral with) either or both termini of the heavy chain and/or light chain of the antibody. In some embodiments, the bone-targeting peptide is not attached to the light chain through the light chain's N-terminus. The attachment or fusion can be a direct connection (i.e., without a spacer or linker), or through a spacer or linker (represented by the wavy lines; e.g., a peptide linker). Specific examples of these formats are shown in Tables 1 and 7 below.

Any suitable spacer or linker can be used herein to attach the bone-targeting peptide by, e.g., recombinant technology or chemical conjugation, to an antibody of interest. For example, a peptide linker having one, two, three, or more repeats of the G4S peptide (SEQ ID NO: 9) may be used. Other suitable peptide linkers can also be used. See, e.g., Chen et al., Adv Drug Deliv Rev 65(10):1357-1369 (2013).

Exemplary Bone-Targeting Antibodies and Antigen-Binding Fragments Thereof

The present invention discloses antibodies and antigen-binding fragments having one or more poly-D (poly-aspartate or poly-Asp) peptides (e.g., a D10 sequence) attached thereto. These modified antibodies and fragments have improved localization to bone. In one particular embodiment, these antibodies are anti-TGFβ antibodies, as described herein. While not wishing to be bound by theory, it is believed that effectively targeting anti-TGFβ antibodies to bone with one or more poly-D peptides may provide a new therapy for individuals with diseases characterized by pathophysiological bone degeneration associated with TGFβ.

However, while numerous embodiments and examples herein are expressed in the context of using α-TGFβ antibodies and D10 sequences, it is contemplated that other antibodies or proteins suitable for treating an abnormal bone condition or a bone disease can be modified with bone-targeting moieties as described herein. For example, therapeutic antibodies for treating bone loss, stimulating bone growth, or targeting abnormal cells (e.g., cancer cells) in bone can be linked to one or more bone-targeting peptides as described herein. The therapeutic antibodies may bind to proteins or peptides involved in bone formation or maintenance. Further, other bone localization or targeting peptides may be used.

As used herein, the terms "α-TGFβ antibody" and "anti-TGFβ antibody" can be used interchangeably and refer to an antibody, or an antigen-binding fragment thereof, that is specific for TGFβ1, TGFβ2, and/or TGFβ3. For example, at least one antigen-binding site (or paratope) of an α-TGFβ antibody, or an antigen-binding fragment thereof, binds to an epitope found on human TGFβ1, TGFβ2, and/or TGFβ3.

Figure 2:
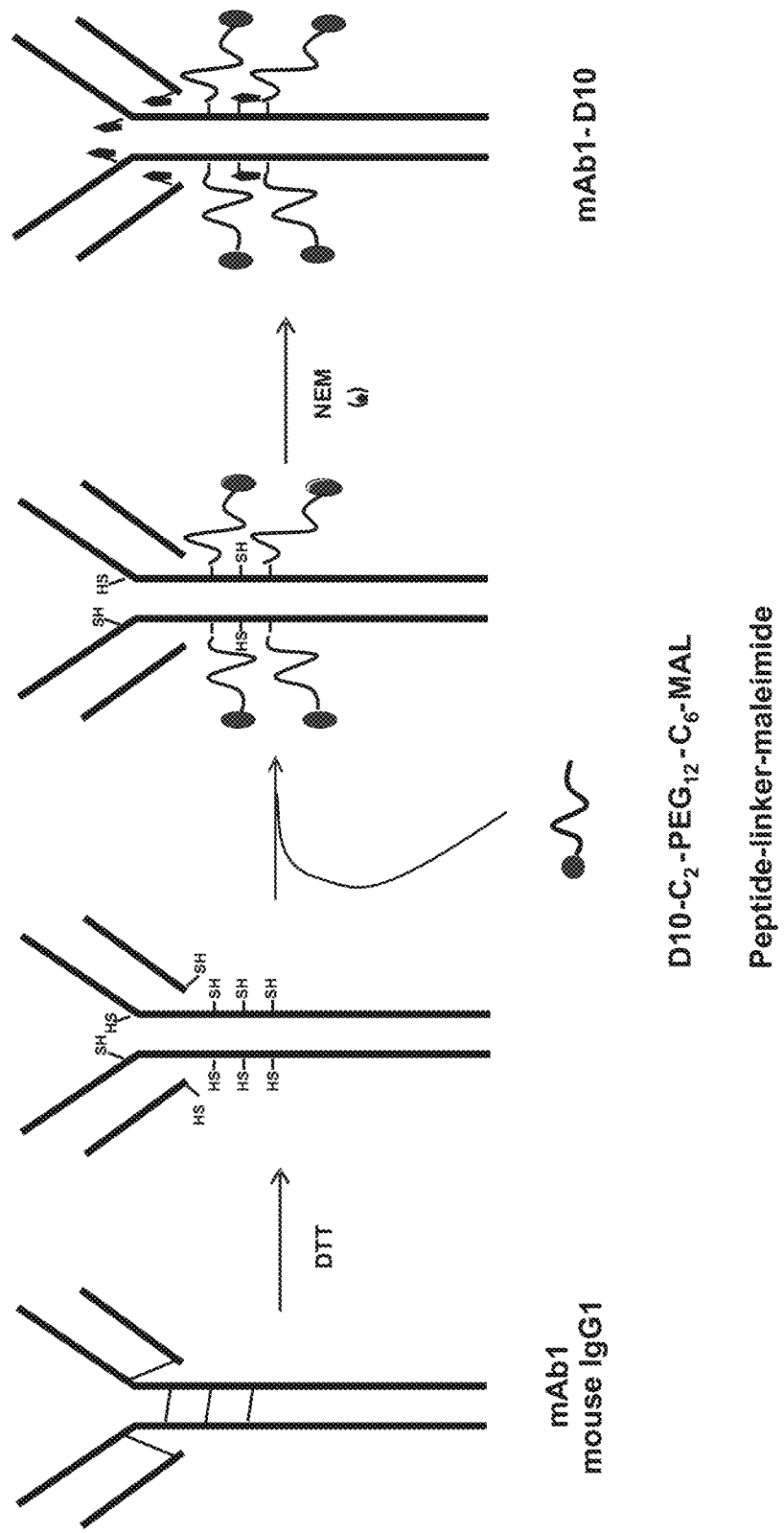
FIG. 2 depicts the process of chemically conjugating a peptide bearing a linker (peptide linker) and a maleimide functional group to reduced hinge region disulfides on a murine IgG$_1$ antibody.

In one embodiment, a contemplated α-TGFβ antibody-D10 construct may be created by chemical conjugation. For example, chemical conjugation may be performed by methods known in the art such as those disclosed in U.S. Pat. Nos. 7,763,712, 4,671,958, and 4,867,973, each of which is incorporated by reference. In another example, a peptide or other linker can be used to attach a D10 peptide to an antibody (see FIGS. 1 and 2). In a further embodiment, reduction of thiol groups at the hinge region (e.g., hinge region cysteine residues) of the antibody allows chemical conjugation of poly-D peptides using a PEG spacer. Similarly, other cysteine residues of contemplated antibodies and antibody fragments, either native to the antibodies and fragments or introduced by mutagenesis, can be chemically conjugated with poly-D peptides. One such contemplated assembly scheme of an α-TGFβ antibody chemically conjugated with a D10 peptide is illustrated in FIG. 2.

In another embodiment, a contemplated α-TGFβ antibody-D10 construct may be created by recombinant expression, where the D10 sequence is added to the amino acid sequence of the heavy chain and/or light chain of the α-TGFβ antibody. For example, the nucleic acid sequences encoding the amino acid sequences of the heavy and/or light chains can be modified to encode a D10 sequence that would be expressed either at the N-terminus, the C-terminus, or both N-terminus and C-terminus of the heavy and/or light chains of the α-TGFβ antibody. Similarly, one or more D10 sequences could be added to an amino acid sequence of an antibody heavy chain at or near the hinge region and/or within the amino acid sequence of an antibody light chain. Each nucleic acid sequence for the D10 harboring-heavy and/or light chain may be incorporated into an expression vector and subsequently transfected into a host cell capable of expressing and translating the nucleic acid sequence into the corresponding amino acid sequence. Moreover, the host cell is capable of assembling the expressed amino acid sequences into the functional protein by combining each of the heavy chain and light chain with its complementary sequence to form an α-TGFβ antibody-D10 construct. Examples of contemplated recombinant α-TGFβ antibody-D10 fusion variants are illustrated in FIGS. 9A and 9B.

While a poly-D peptide is discussed herein, other similar peptides may also be used to enable targeting of an antibody, another protein, or a peptide to bone. For example, aspartic acid repeat sequences may have more or fewer residues than a D10 sequence, such as about 2, or about 4, or about 6, or about 8, or about 12, or about 14, or about 16, or, about 18, or about 20, or about 30, or 6, 7, 8, 9, 10 or 11 residues, and the like. Further, other natural amino acids with similar chemical properties, such as glutamate, or non-natural amino acids and/or other chemically equivalent compounds may be substituted for or used in combination with aspartic acid, as well.

In one embodiment, it is contemplated that an antibody with one or more poly-D peptides attached thereto will exhibit at least about a 2-fold, or about a 3-fold, or about at 5-fold, or about a 10-fold, or about a 20-fold increase in localization to bone compared to the same antibody without the one or more poly-D peptides.

Moreover, while an α-TGFβ antibody is described herein, any antibody that binds other proteins involved in bone formation or bone maintenance may be similarly modified to target the antibody to bone, as desired. Antibodies or antigen-binding fragments thereof contemplated herein may be from any species or represent hybrid antibodies combining heavy chains and light chains from different species, and may be specific for any desired epitope. In addition, antibodies that may be used herein are not limited by isotype, and may be any of $IgG_1$, $IgG_2$, $IgG_3$, $IgG_4$, $IgA_1$, $IgA_2$, IgM, IgE, or IgD. Antibody fragments may also be used. For example, D10 sequences or other bone-targeting compounds may be attached to Fab and/or Fc fragments or any other antibody fragment to achieve a desired result as described herein. Further, D10 sequences can be attached to scFv fragments and other similar fusion proteins. In another embodiment, D10 sequences can be attached to antibodies having a S228P core-hinge mutation (numbered according to the EU numbering system; or alternatively S241P according to the Kabat system; see Kabat et al., Sequences of Proteins of Immunological Interest, $4^{th}$ ed., United States Government Printing Office, 165-492 (1987); and Silva et al. Jour. Biol. Chem. 290:5462-5469 (2015)).

In a further embodiment, antibodies and/or other proteins contemplated herein may be conjugated with additional molecules. For example, antibodies or other proteins contemplated herein may be conjugated with chemical labels that allow tracking of the antibodies/proteins when injected or otherwise introduced into a subject. For example, radiolabels, fluorescent compounds, and the like may be attached to the antibodies/proteins to aid their tracking in vivo. Further, antibodies and/or other proteins contemplated herein may also be conjugated with additional compounds having a therapeutic effect, such as small molecules, pharmaceuticals, antineoplastic agents, growth hormones, vitamins, etc., such that the antibodies and/or other proteins may serve as a vehicle for one or more of such compounds.

In some embodiments, the bone-targeting anti-TGFβ antibody comprises a heavy chain comprising an amino acid sequence set forth in any of SEQ ID NOS: 2, 3, 4, and 5, and a light chain comprising an amino acid sequence set forth in any of SEQ ID NOS: 6, 7, 8, 11, and 12, with the proviso that the heavy chain amino acid sequence is not SEQ ID NO: 2 when the light chain amino acid sequence is SEQ ID NO: 6. Exemplary antibodies are mAb1 F3, mAb1 F4, mAb1 F5, mAb1 F6, mAb1 F8, mAb1 F9, mAb1 F10, mAb1 F11, mAb1 F13, mAb1 F14, mAb1 F15, mAb1 F16, mAb1 F18, mAb1 F19, and mAb1 F20 (Table 1).

In other embodiments, the bone-targeting anti-TGFβ antibody comprises a heavy chain comprising an amino acid sequence set forth in any of SEQ ID NOS: 13, 14, 16, and 17, and a light chain comprising an amino acid sequence set forth in any of SEQ ID NOS: 15, 18, 19, 20, 21, and 22, with the proviso that the heavy chain amino acid sequence is not SEQ ID NO: 13 when the light chain amino acid sequence is SEQ ID NO: 15. Exemplary antibodies are mAb2 F3, mAb2 F4, mAb2 F5, mAb2 F6, mAb2 F8, mAb2 F9, mAb2 F10, mAb2 F11, mAb2 F13, mAb2 F14, mAb2 F15, mAb2 F16, mAb2 F18, mAb2 F19, and mAb2 F20 (Table 7).

In some embodiments, the antibodies of the present invention, such as the anti-TGFβ antibodies, do not have the C-terminal lysine in the heavy chain. The C-terminal lysine may be removed during manufacture or by recombinant technology (i.e., the coding sequence of the heavy chain does not include a codon for the C-terminal terminal lysine). Thus, contemplated within the invention also are antibodies comprising the heavy chain amino acid sequence of SEQ ID NO: 2 or 13 without the C-terminal lysine. A poly-D peptide may be attached to the C-terminus of a heavy chain with or without the C-terminal lysine.

Treatment Methods

In one particular embodiment, a method of treating an individual such as a human patient for bone loss associated with TGFβ includes administering an effective amount of an anti-TGFβ antibody targeted to bone to the individual. The method can further include a step of measuring or detecting a reduction in TGFβ levels or activity, a reduction in bone loss or the rate of bone loss, an increase in bone density, and/or an increase in bone strength.

An "effective amount," as used herein, refers to an amount of a therapeutic agent, such as an α-TGFβ antibody or antibody fragment, that when administered to an individual in need thereof improves an individual's health, such as, for example, by reducing TGFβ levels or activity associated with bone, reducing bone loss or the rate of bone loss, increasing bone density, and/or increasing bone strength.

As used herein, the term "individual" refers to an animal. Examples of individuals include humans, domesticated animals, household pets, and other animals without limitation. Further examples of individuals include animals having a bone disease associated with TGFβ.

In another embodiment, pharmaceutical antibody formulations or compositions including aqueous liquid drug product formulations and lyophilized drug product formulations containing one or more bone-targeting anti-TGFβ antibodies such as chemical conjugates or recombinant fusion variants are contemplated. Pharmaceutical compositions including bone-targeting anti-TGFβ antibody and/or antibody fragments can be formulated as described in U.S. Patent Application Publication No. US 2014/0286933 A9, which is incorporated herein by reference, or otherwise as is known in the art.

In one particular embodiment, a method for treating bone disease includes administering an effective amount of an anti-TGFβ antibody targeted to bone to an individual with a bone disease, such as bone diseases associated with chronic kidney disease, cancer metastasis to bone, or abnormal metabolic conditions. In another particular embodiment, a method for treating osteogenesis imperfecta includes administering an effective amount of an anti-TGFβ antibody targeted to bone to an individual with osteogenesis imperfecta. In a further particular embodiment, a method for treating osteoporosis includes administering an effective amount of an anti-TGFβ antibody targeted to bone to an individual with osteoporosis.

In some embodiments, the patients are treated with a combination of a bone-targeting antibody or antibody fragment of the present invention and another therapeutic agent, such as a therapeutic agent for a bone loss condition (e.g., bisphosphonates). The antibody or antibody fragment and the other therapeutic agent can be administered to the patient simultaneously or sequentially.

Methods of Making Antibodies

The antibodies or fragments of the present invention can be made by methods well established in the art. DNA sequences encoding the heavy and light chains of the antibodies can be inserted into expression vectors such that the genes are operatively linked to necessary expression control sequences such as transcriptional and translational control sequences. Expression vectors include plasmids, retroviruses, adenoviruses, adeno-associated viruses (AAV), plant viruses such as cauliflower mosaic virus, tobacco mosaic virus, cosmids, YACs, EBV derived episomes, and the like. The antibody light chain coding sequence and the antibody heavy chain coding sequence can be inserted into separate vectors, and may be operatively linked to the same or different expression control sequences (e.g., promoters). In one embodiment, both coding sequences are inserted into the same expression vector and may be operatively linked to the same expression control sequences (e.g., a common promoter), to separate identical expression control sequences (e.g., promoters), or to different expression control sequences (e.g., promoters). The antibody coding sequences may be inserted into the expression vector by standard methods (e.g., ligation of complementary restriction sites on the antibody gene fragment and vector, or blunt end ligation if no restriction sites are present).

In addition to the antibody chain genes, the recombinant expression vectors may carry regulatory sequences that control the expression of the antibody chain genes in a host cell. Examples of regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters.

In addition to the antibody chain genes and regulatory sequences, the recombinant expression vectors of the invention may carry additional sequences, such as sequences that regulate replication of the vector in host cells (e.g., origins of replication) and selectable marker genes. For example, the selectable marker gene confers resistance to drugs, such as G418, hygromycin or methotrexate, on a host cell into which the vector has been introduced. Selectable marker genes may include the dihydrofolate reductase (DHFR) gene (for use in dhfr-host cells with methotrexate selection/amplification), the neo gene (for G418 selection), and the glutamate synthetase gene.

The expression vectors encoding the antibodies of the present invention are introduced to host cells for expression. The host cells are cultured under conditions suitable for expression of the antibody, which is then harvested and isolated. Host cells include mammalian, plant, bacterial or yeast host cell. Mammalian cell lines available as hosts for expression are well known in the art and include many immortalized cell lines available from the American Type Culture Collection (ATCC). These include, inter alia, Chinese hamster ovary (CHO) cells, NS0 cells, SP2 cells, HEK-293T cells, 293 Freestyle cells (Invitrogen), NIH-3T3 cells, HeLa cells, baby hamster kidney (BHK) cells, African green monkey kidney cells (COS), human hepatocellular carcinoma cells (e.g., Hep G2), A549 cells, and a number of other cell lines. Cell lines may be selected based on their expression levels. Other cell lines that may be used are insect cell lines, such as Sf9 or Sf21 cells.

Further, expression of antibodies can be enhanced using a number of known techniques. For example, the glutamine synthetase gene expression system (the GS system) is a common approach for enhancing expression under certain conditions.

Tissue culture media for the host cells may include, or be free of, animal-derived components (ADC), such as bovine serum albumin. In some embodiments, ADC-free culture media is preferred for human safety. Tissue culture can be performed using the fed-batch method, a continuous perfusion method, or any other method appropriate for the host cells and the desired yield.

Pharmaceutical Compositions

The antibody of the invention can be formulated for suitable storage stability. For example, the antibody can be lyophilized or stored or reconstituted for use using pharmaceutically acceptable excipients. For a combination therapy, the two or more therapeutic agents such as antibodies can be co-formulated, e.g., mixed and provided in a single composition.

The term "excipient" or "carrier" is used herein to describe any ingredient other than the compound(s) of the invention. The choice of excipient(s) will to a large extent depend on factors such as the particular mode of administration, the effect of the excipient on solubility and stability, and the nature of the dosage form. "Pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In some cases, isotonic agents, for example, sugars, polyalcohols such as mannitol, sorbitol, or sodium chloride will be included in the composition. Additional examples of pharmaceutically acceptable substances are wetting agents or minor amounts of auxiliary substances such as wetting or emulsifying agents, preservatives or buffers, which enhance the shelf life or effectiveness of the antibody.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intratumoral, and intrasynovial injection or infusions; and kidney dialytic infusion techniques. Regional perfusion is also contemplated. Preferred embodiments may include the intravenous and subcutaneous routes.

Formulations of a pharmaceutical composition suitable for parenteral administration typically comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen free water) prior to parenteral administration of the reconstituted composition. Parenteral formulations also include aqueous solutions which may contain excipients such as salts, carbohydrates and buffering agents (e.g., a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

In some embodiments, the antibody or antigen-binding fragment of the present invention may be administered at 40, 20, or 15 mg/kg or less (such as 14, 13, 12, 11, 10, 9, 8, 7, 6, 5, 4, 3, 2, or 1 mg/kg). In some further embodiments, the doses may be 0.01, 0.02, 0.03, 0.04, 0.05, 0.1, 0.2, 0.3, 0.4, or 0.5 mg/kg. The dosing frequency may be, for example, daily, every two, three, four, or five days, weekly, biweekly, or triweekly, monthly, bimonthly, every three months, every six months, or every twelve months, or as needed. The antibody may be administered by intravenous (e.g., intravenous infusion over 0.5-8 hours), subcutaneously, intramuscularly, or any other route of administration that is appropriate for the condition and the drug formulation.

Exemplary Embodiments

Further particular embodiments of the present invention are described as follows.

1. An antibody, or an antigen-binding fragment thereof, comprising a heavy chain, a light chain, and one or more poly-aspartate (poly-D) peptides connected to (i) the heavy chain, (ii) the C-terminus of the light chain, or (iii) both (i) and (ii).

2. The antibody or antigen-binding fragment of embodiment 1, wherein the one or more poly-D peptides are connected to the antibody or antigen-binding fragment by chemical conjugation.

3. The antibody or antigen-binding fragment of embodiment 2, wherein the one or more poly-D peptides are conjugated to the heavy chain at the hinge region.

4. The antibody or antigen-binding fragment of embodiment 2 or 3, wherein the one or more poly-D peptides are conjugated to the antibody or antigen-binding fragment by a polyethylene glycol (PEG) spacer.

5. The antibody or antigen-binding fragment of embodiment 1, comprising a poly-D peptide integral with an amino acid sequence of the heavy chain or the light chain.

6. The antibody or antigen-binding fragment of embodiment 5, comprising a poly-D peptide integral with the N-terminus of the heavy chain.

7. The antibody or antigen-binding fragment of embodiment 5, comprising a poly-D peptide integral with the C-terminus of the heavy chain.

8. The antibody or antigen-binding fragment of embodiment 5, comprising a first poly-D peptide integral with the N-terminus of the heavy chain and a second poly-D peptide integral with the C-terminus of the heavy chain.

9. The antibody or antigen-binding fragment of any one of embodiments 5-8, comprising a poly-D peptide integral with the C-terminus of the light chain.

10. The antibody or antigen-binding fragment of any one of embodiments 5-9, wherein the poly-D peptide(s) are fused to the heavy or light chain via a peptide linker.

11. The antibody or antigen-binding fragment of embodiment 10, wherein the peptide linker comprises 1-3 repeats of the amino acid sequence GGGGS (SEQ ID NO: 9).

12. The antibody or antigen-binding fragment of any one of the preceding embodiments, wherein the one or more poly-D peptides each independently comprise 2-30 aspartic acid residues.

13. The antibody or antigen-binding fragment of embodiment 12, wherein the one or more poly-D peptides each comprise 10 aspartic acid residues (SEQ ID NO: 1).

14. The antibody or antigen-binding fragment of any one of the preceding embodiments, wherein the antibody is an IgG.

15. The antibody or antigen-binding fragment of embodiment 15, wherein the antibody is an $IgG_1$ or $IgG_4$.

16. The antibody or antigen-binding fragment of any one of the preceding embodiments, wherein the antibody or antigen-binding fragment specifically binds to one or more of TGFβ1, TGFβ2, and TGFβ3.

17. The antibody or antigen-binding fragment of embodiment 16, wherein the antibody comprises the heavy chain complementarity-determining regions (CDR) 1-3 in SEQ ID NO: 13 and the light chain CDR1-3 in SEQ ID NO: 15.

18. The antibody or antigen-binding fragment of embodiment 17, wherein the antibody comprises a heavy chain variable domain ($V_H$) amino acid sequence corresponding to residues 1-120 of SED ID NO: 13 and a light chain variable domain ($V_L$) amino acid sequence corresponding to residues 1-108 of SEQ ID NO:15.

19. The antibody or antigen-binding fragment of embodiment 17 or 18, wherein the antibody comprises a human $IgG_4$ constant region having a proline at position 228 (EU numbering).

20. The antibody or antigen-binding fragment of embodiment 19, wherein the heavy chain of the antibody comprises the amino acid sequence of SEQ ID NO: 13 with or without the heavy chain C-terminal lysine, and the light chain of the antibody comprises the amino acid sequence of SEQ ID NO: 15.

21. The antibody of embodiment 17, wherein the heavy chain comprises the amino acid sequence of SEQ ID NO: 13 with or without the heavy chain C-terminal lysine, SEQ ID NO: 14 with or without the lysine immediately preceding the C-terminal D10 sequence, SEQ ID NO: 16 with or without the heavy chain C-terminal lysine, or SEQ ID NO: 17 with or without the lysine immediately preceding the C-terminal D10 sequence, and the light chain comprises the amino acid sequence of SEQ ID NO: 15, 19, 21, or 22.

22. The antibody or antigen-binding fragment of embodiment 16, wherein the antibody is mouse antibody 1D11 having the heavy and light chain amino acid sequences of SEQ ID NO: 2 with or without the C-terminal lysine and SEQ ID NO: 6, respectively.

23. An IgG$_4$ antibody that binds human TGFβ1, TGFβ2, and TGFβ3, wherein the heavy chain of the antibody comprises the amino acid sequence of SEQ ID NO: 14 (with or without the lysine immediately preceding the C-terminal D10 sequence), and the light chain comprises the amino acid sequence of SEQ ID NO: 15.

24. An IgG$_4$ antibody that binds human TGFβ1, TGFβ2, and TGFβ3, wherein the heavy chain of the antibody comprises the amino acid sequence of SEQ ID NO: 17 (with or without the lysine immediately preceding the C-terminal D10 sequence), and the light chain comprises the amino acid sequence of SEQ ID NO: 15.

25. The antibody or antigen-binding fragment of any one of the preceding embodiments, wherein the antibody or antigen-binding fragment exhibits at least a 2-fold increase in localization to bone compared to an antibody with the same heavy chain and light chain but lacking the poly-D peptide(s).

26. A pharmaceutical composition comprising an antibody or antigen-binding fragment of any one of the preceding embodiments and a pharmaceutically acceptable excipient.

27. A method for treating an individual with a bone condition that benefits from inhibition of TGFβ, comprising administering to the individual an effective amount of an anti-TGFβ antibody or antigen-binding fragment of any one of embodiments 16-25.

28. The method of embodiment 27, further comprising detecting at least one of (1) a reduction in TGFβ levels, (2) a reduction in TGFβ activity, (3) a reduction in bone loss, (4) a reduction in rate of bone loss, (5) an increase in bone density, (6) an increase in bone strength, and (7) a reduction in IL-11 levels.

29. An antibody or antigen-binding fragment of any one of embodiments 16-25 for use in treating an individual with a bone condition that benefits from inhibition of TGFβ.

30. Use of an antibody or antigen-binding fragment of any one of embodiment 16-25 for the manufacture of a medicament for treating an individual with a bone condition that benefits from inhibition of TGFβ.

31. The method of embodiment 27, the antibody or antigen-binding fragment for use of embodiment 29, or the use of embodiment 30, wherein the individual is a human.

32. The method, antibody or antigen-binding fragment for use, or use of embodiment 31, wherein the human has osteogenesis imperfecta.

33. The method, antibody or antigen-binding fragment for use, or use of embodiment 31, wherein the human has bone loss or osteoporosis.

34. The method, antibody or antigen-binding fragment for use, or use of embodiment 31, wherein the human has chronic kidney disease.

35. The method, antibody or antigen-binding fragment for use, or use of embodiment 31, wherein the human is a cancer patient with bone metastasis.

36. An isolated nucleic acid molecule, comprising a nucleotide sequence encoding the heavy chain, the light chain, or both, of the antibody or antigen-binding fragment of any one of embodiments 1-25.

37. An expression vector comprising the isolated nucleic acid molecule of embodiment 36.

38. A host cell comprising the expression vector of embodiment 37.

39. The host cell of embodiment 38, wherein the host cell is a mammalian cell.

40. A method of producing an antibody or antigen-binding fragment of any one of embodiments 1-25, the method comprising:
providing a host cell comprising first and second nucleotide sequences encoding the heavy chain and light chain, respectively, of the antibody or antigen-binding fragment,
growing the host cell under conditions permitting production of the antibody or antigen-binding fragment, and
recovering the antibody or antigen-binding fragment.

41. The method of embodiment 40, wherein the first nucleotide sequence comprises SEQ ID NO: 23, 24, 25, or 26 (with or without the codon for the heavy chain C-terminal lysine), and the second nucleotide sequence comprises SEQ ID NO: 27, 29, 31, or 32.

42. A method of producing a bone-targeting antibody or antigen-binding fragment, comprising:
providing an antibody or an antigen-binding fragment thereof and one or more poly-D peptides, and
attaching the poly-D peptides to the antibody through a covalent bond by chemical conjugation.

43. The method of any one of embodiments 40-42, further comprising formulating the antibody or antigen-binding fragment as a pharmaceutical composition comprising a pharmaceutically acceptable carrier.

44. A method of producing a bone-targeting pharmaceutical composition, comprising:
providing an antibody or antigen-binding fragment of any one of embodiments 1-25, and
admixing the antibody or antigen-binding fragment with a pharmaceutically acceptable carrier.

The invention will be further described in the following examples, which do not limit the scope of the invention described in the claims.

EXAMPLES

The Examples that follow are illustrative of specific embodiments of the invention, and various uses thereof. They are set forth for explanatory purposes only and are not to be taken as limiting of the invention.

TGFβ Antibody

A first anti-TGFβ antibody, referred to herein as mAb1, is a mouse IgG$_1$ monoclonal antibody specific for human TGF-β1, TGF-β2, and TGF-β3 ("pan-specific") and is available from R&D Systems (Clone #1D11, Minneapolis, MN). The mAb1 antibody served as a template in the examples.

A second anti-TGFβ antibody, referred to herein as mAb2, used in the examples is a human anti-TGFβ IgG$_4$ antibody with a hinge mutation S228P (EU numbering). The mAb2 antibody is similar to antibodies disclosed in U.S. Pat. No. 9,090,685, which is incorporated by reference. Antibody mAb2 has an estimated molecular weight of 144 KD when un-glycosylated. Its heavy and light chain amino acid sequences are SEQ ID NOS: 13 and 15, respectively. These two sequences are shown below. Variable domains are italicized, and are designated herein as heavy chain variable domain (HCVD, SEQ ID NO: 39) and light chain variable domain (LCVD, SEQ ID NO: 40). CDRs are shown in boxes and are designated heavy chain complementarity-determining region 1 (HCDR1, SEQ ID NO: 33); HCDR2 (SEQ ID NO: 34); and HCDR3 (SEQ ID NO: 35), and light chain complementarity-determining region 1 (LCDR1, SEQ ID NO: 36); LCDR2 (SEQ ID NO: 37); and LCDR3 (SEQ ID NO: 38). The glycosylation site in the constant domain of the heavy chain is in boldface (N297).

(SEQ ID NO: 13)
QVQLVQSGAE VKKPGSSVKV SCKASGYTFS SNVIS WVRQA PGQGLEWMG VIPIVDIANY
AQRFKG RVTI TADESTSTTY MELSSLRSED TAVYYCAST L BLVLDAMDY W GQGTLVTVSS
ASTKGPSVFP LAPCSRSTSE STAALGCLVK DYFPEPVTVS WNSGALTSGV HTFPAVLQSS
GLYSLSSVVT VPSSSLGTKT TYCNVDHKPS NTKVDKRVES KYGPPCPPCP APEFLGGPSV
FLFPPKPKDT LMISRTPEVT CVVVDVSQED PEVQFNWYVD GVEVHNAKTK PREEQFNSTY
RVVSVLTCLVK QDWLNGKEYK CKVSNKGLPS SIEKTISKAK GQPREPQVYT LPPSQEEMTK
NQVSLTCLVK GFYPSDIAVE WESNGQPENN YKTTPPVLDS DGSFFLYSRL TVDKSRWQEG
NVFSCSVMHE ALHNHYTQKS LSLSLGK (SEQ ID NO: 15)
ETVLTQSPGT LSLSPGERAT LSC RASQSLG SSYLA WYQQK PGQAPRLLIY GASSRAP GIP
DRFSGSGSGT DFTLTISRLE PEDFAVYYCQ QYADSPIT FG QGTRLEIKRT VAAPSVFIFP
PSDEQLKSGT ASVVCLLNNF YPREAKVQWK VDNALQSGNS QESVTEQDSK DSTYSLSSTL
TLSDADYEKH KVYADEVTGQ GLSSPVTKSF NRGEC

As described herein, other antibodies, antibody fragments, proteins, or peptides that bind proteins involved in bone formation or bone maintenance may be used.

Figure 3A:
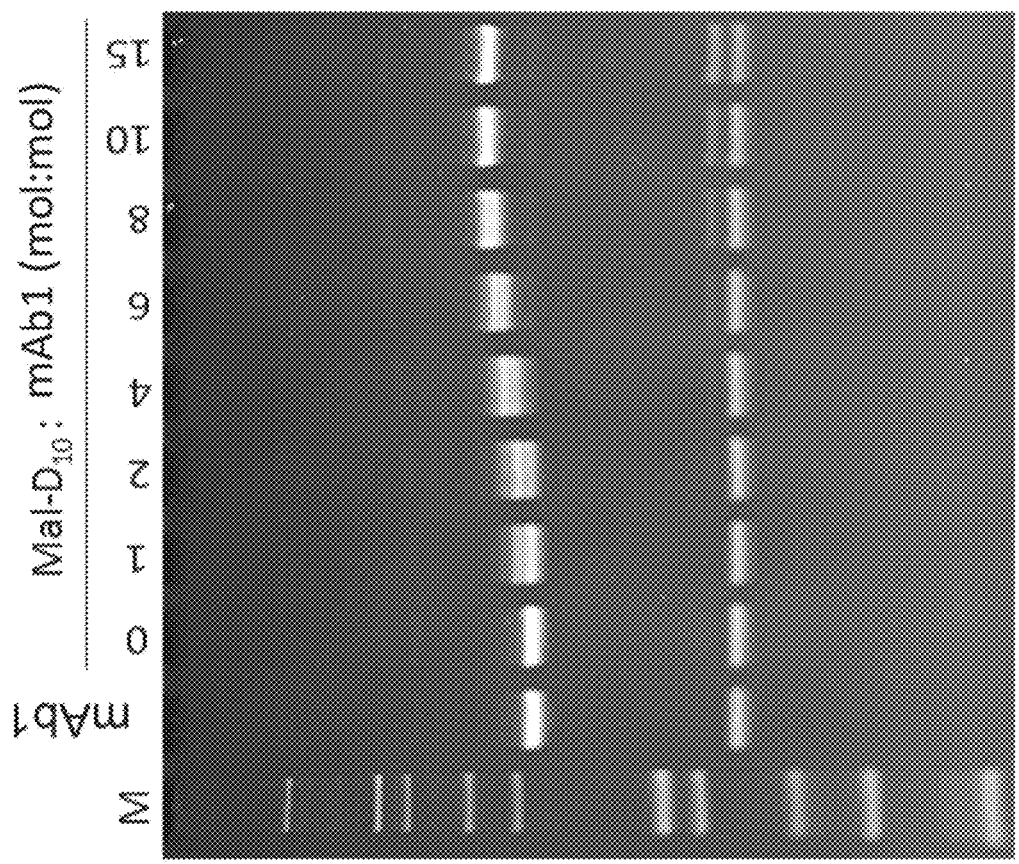
FIG. 3A depicts a reducing SDS-PAGE gel of chemical conjugates of a D10 peptide-linker with an anti-TGFβ murine IgG$_1$, mAb1. The upper band(s) represents the heavy chain and the lower band the light chain.
Figure 3B:
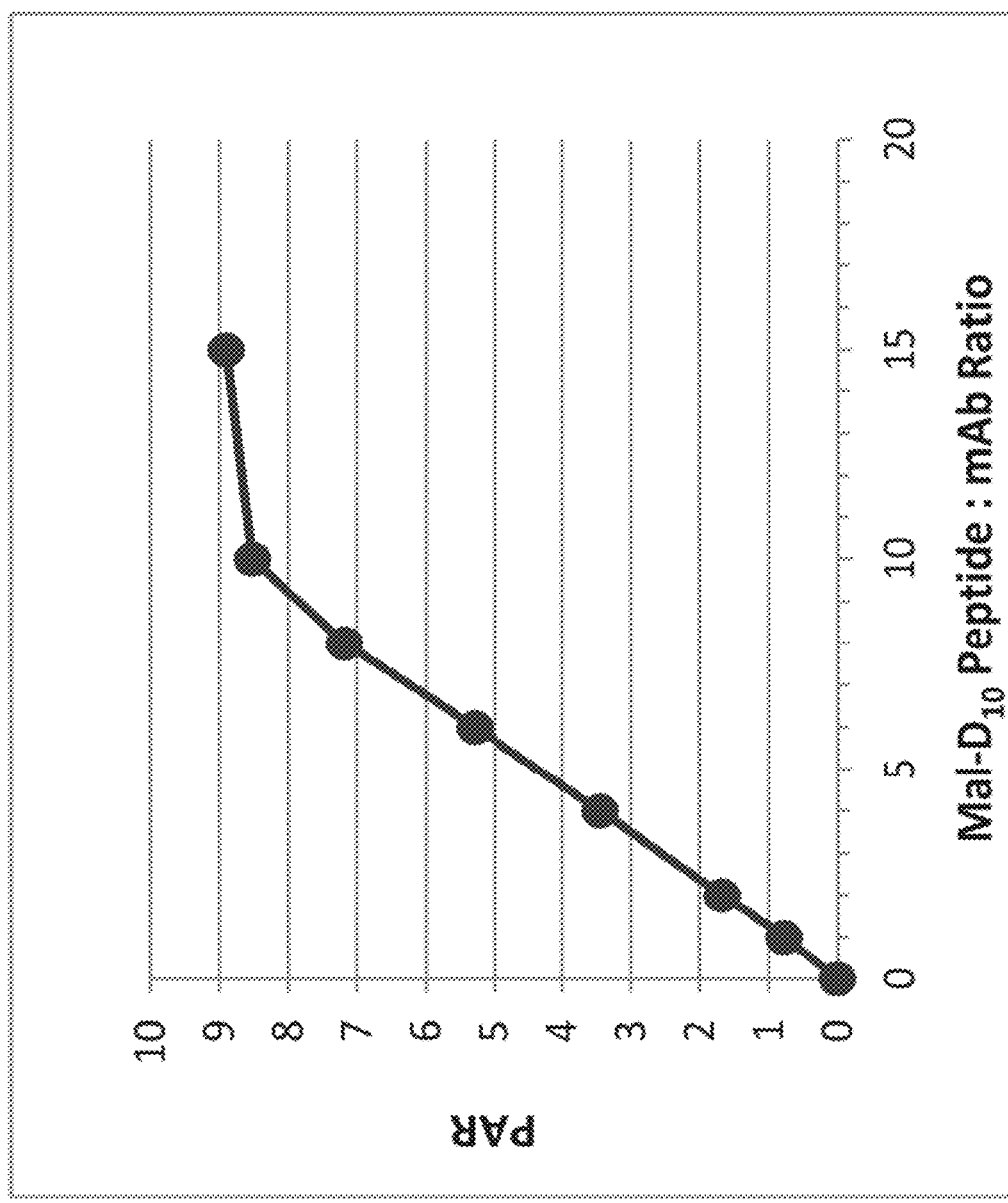
FIG. 3B depicts peptide to antibody ratio (PAR) values vs. the peptide-maleimide:mAb ratio in the chemical conjugation reaction of Example 1, which shows a linear increase in the PAR with increasing number of peptides up to 8 mol:mol PAR.

Example 1: Preparation of Chemical Conjugates of D10 Peptide with mAb1 α-TGFβ Antibody D10 peptide chemical conjugates of the α-TGFβ antibody mAb1 were prepared in the manner depicted in FIG. 2. mAb1 (2.0 mg) was exchanged into degassed borate buffer (25 mM sodium chloride, 1 mM DTPA, 20 mM sodium borate pH 8.0) by three rounds of ultrafiltration over Amicon® Ultra 50 kDa MWCO centrifugal filters (EMD Millipore). The hinge region disulfides were then reduced with 12 mol:mol dithiothreitol (DTT) per mAb for 2 hr at 37° C. The product was desalted over a 4 mL Amicon® Ultra filter with degassed borate buffer. Aliquots (1 nmol, 150 µg) were reacted at 25° C. with increasing amounts (1-15 mol:mol) of a D10-maleimide peptide (Ac-D10-C2-PEG12-C6-maleimide, where PEG12 consists of a defined length PEG containing 12 ethylene oxide groups). After 1.5 hr, remaining unreacted thiol groups were blocked by the addition of 12 equivalents of N-ethylmaleimide followed by incubation for 1.5 hr. The products were desalted by ultrafiltration. FIG. 3A depicts SDS-PAGE of 0.5 µg of each product on a 4-12% NuPAGE gel stained with SimplyBlue™ (Thermo Scientific) and imaged by an Odyssey® near IR scanner (LiCor). The lane fluorescence profiles were integrated using AlphaView software (ProteinSimple Corp.) and the peptide to antibody ratio (PAR) determined. The small shift in mobility in each of the heavy or light chain was assumed to represent the addition of a single D10 peptide which is consistent with the maximum of 5 identifiable bands for the heavy chain and 1 for the light chain and matches the number of hinge region cysteines for each. The average number of peptides on the heavy and light chain was separately calculated from the sum of the product of the relative abundance of each minor band times its assigned peptide number. PAR was calculated from the sum of those numbers from the heavy and light chains times two since each chain is represented twice in the whole IgG. The PAR value vs. the peptide-maleimide:mAb ratio in the chemical conjugation reaction is depicted in FIG. 3B which shows a linear increase in the PAR with increasing number of conjugated peptides up to 8 mol:mol.

Example 2: Binding of mAb1-D10 Chemical Conjugates to TGF-β1

In this example, a set of chemical conjugates of varying PAR was prepared in the same fashion as described in Example 1 except that the ratio of DTT was varied from 8-10 mol:mol and the maleimide-peptide:mAb was either 3 or 15 mol:mol. As a control, a human IgG1 (Herceptin®) chemical conjugate was prepared by reduction of its hinge disulfides by 3 mol:mol tris(2-carboxyethylphosphine) (TCEP) for 2 hr 37° C. under argon followed by reaction with 15 mol:mol maleimide-peptide overnight at 25° C. and purified by desalting using ultrafiltration.

Figure 4A:
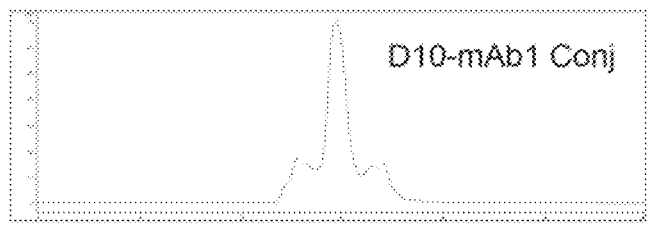
FIGS. 4A-4G depict size-exclusion chromatography of 1:1 molar mixtures of TGFβ1 and chemical conjugates of a D10 peptide with either trastuzumab (Herceptin®) or the anti-TGFβ antibody mAb1.
Figure 4B:
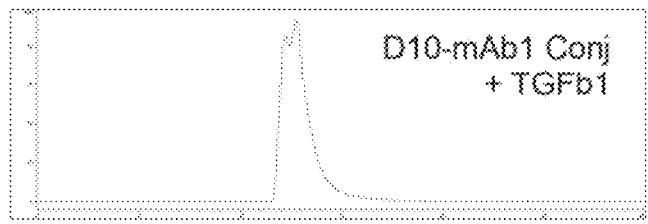
Figure 4C:
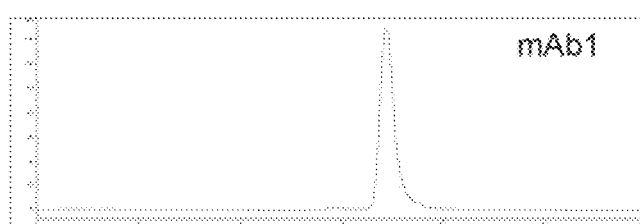
Figure 4D:
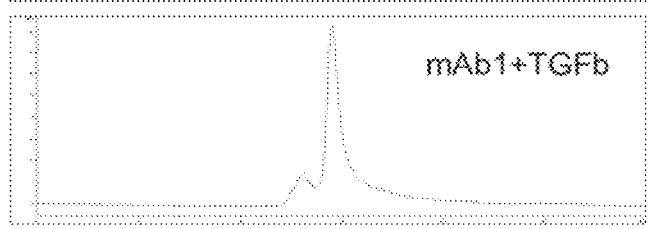
Figure 4E:
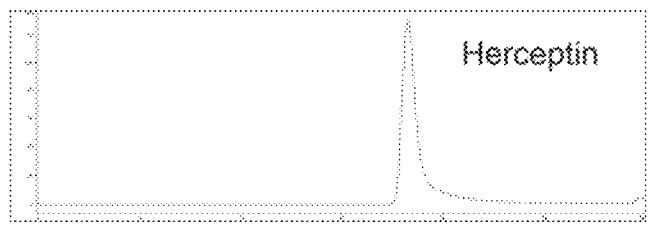
Figure 4F:
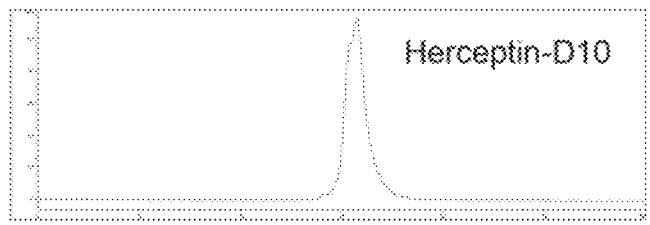
Figure 4G:
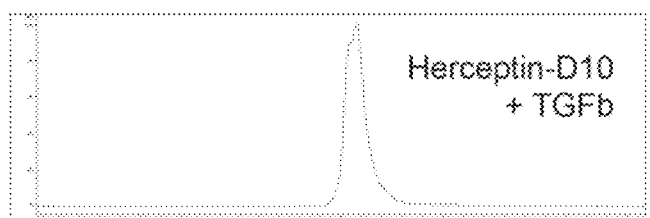

To assess their ability to bind TGF-β1, the chemical conjugates were mixed with TGF-β1 in a 1:1 molar ratio followed by size exclusion chromatography on Superdex 200 (G.E. Healthcare) in phosphate buffered saline (PBS) pH 7.2. The mAb1-D10 chemical conjugate alone yielded a somewhat heterogeneous peak eluting earlier than unmodified mAb1 as shown in FIG. 4A, which is likely due to charge effects produced by the conjugated peptides. Addition of TGF-β1 to the conjugate produced an earlier-eluting peak than either mAb1 or the mAb1-D10 chemical conjugate, indicating formation of a higher molecular weight complex (FIG. 4B). Similarly, addition of TGF-β1 to unmodified mAb1 antibody produced a shift to an earlier retention time (FIGS. 4C, 4D). In contrast, although chemical conjugation of D10 to Herceptin® caused a shift in the retention time of the antibody alone as with the mAb1 conjugate (FIGS. 4E, 4F), adding TGF-β1 (1 mol:mol) to the Herceptin®-D10 conjugate failed to produce any change in its elution time or apparent MW (FIGS. 4F, 4G) indicating binding to the conjugate did not occur as a consequence of the conjugation.

Figure 5A:
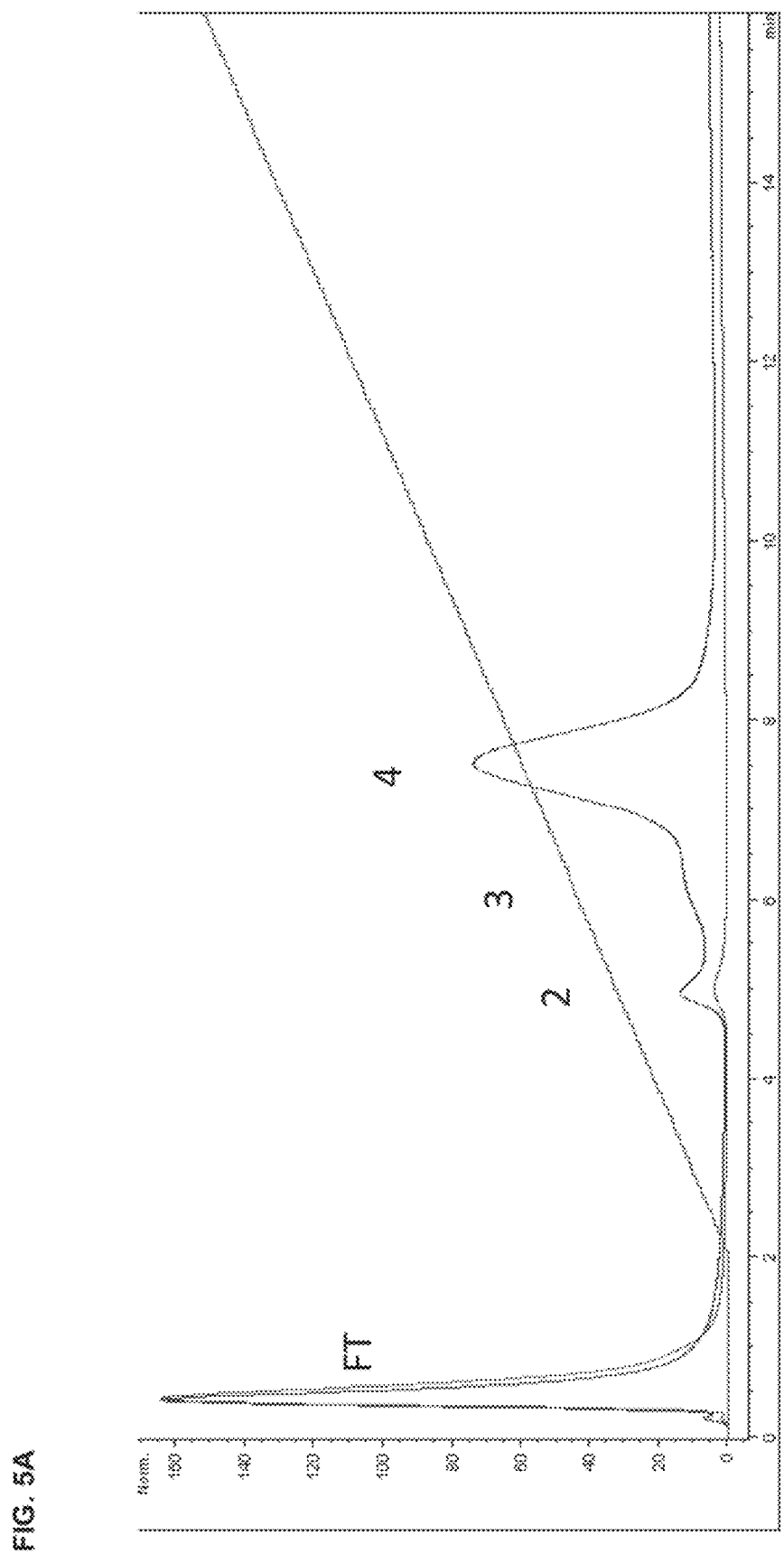
FIG. 5A depicts the $A_{280}$ trace from hydroxyapatite chromatography of mAb1 and a D10-mAb1 conjugate (x-axis=minutes, y-axis=absorbance (normalized)).
Figure 5B:
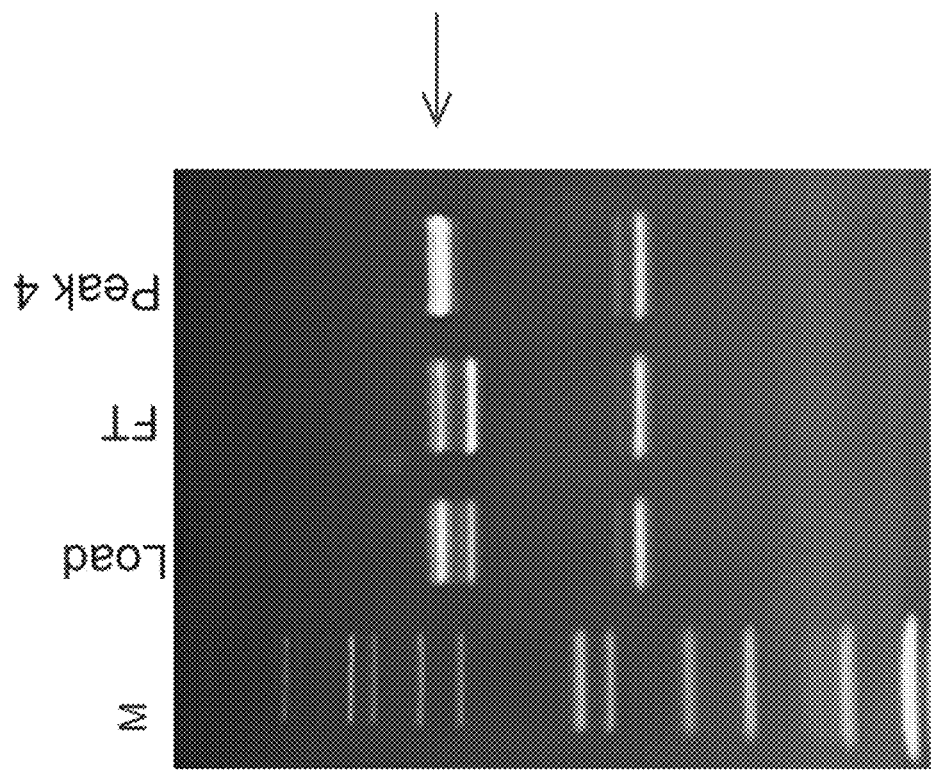
FIG. 5B depicts SDS-PAGE gel of fractions from the flowthrough (FT) and peak 4.
Figure 5B:
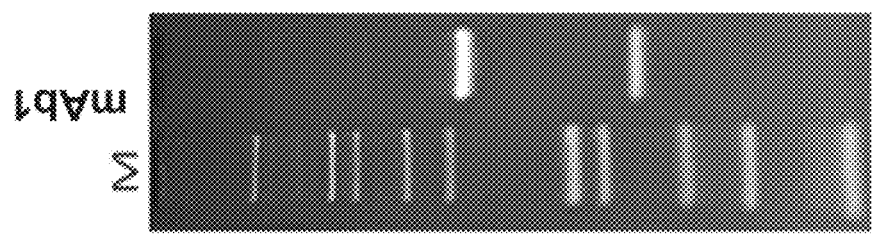

Example 3: Peptide-Dependent Binding of a mAb1-D10 Chemical Conjugate to Hydroxyapatite In this example, a chemical conjugate of D10 with mAb1, such as shown in FIG. 2, was produced by reduction of the hinge region disulfides with 12 eq DTT in 25 mM NaCl, 1 mM DTPA, 20 mM sodium borate pH 8 for 2 hr at 37° C. followed by reaction with 2 mol:mol 2,2'-dipyridyl disulfide (Sigma) to convert a portion of the free thiols back to disulfides. This was followed by reaction with D10-maleimide peptide described in Example 1. The final product was purified by ultrafiltration. A portion (25 µg) was exchanged into 5 mM sodium phosphate pH 7.4 over a spin column and chromatographed over a 100 µL column of ceramic hydroxyapatite (CHT) Type II (BioRad) and eluted with a gradient of 5-500 mM sodium phosphate pH 7.4 at a flow rate of 0.5 mL/min. Unmodified mAb1 was used as a control. The $A_{280}$ column profile is depicted in FIG. 5A. mAb1 showed only trace binding to the column whereas about half of the conjugate bound and eluted around 0.2 M phosphate. Fractions were concentrated and analyzed by SDS-PAGE (FIG. 5B). The unbound (flowthrough or "FT") fraction showed mostly unmodified mAb whereas the major peak 4 contained conjugate with an estimated PAR of 6 by SDS-PAGE.

Figure 6A:
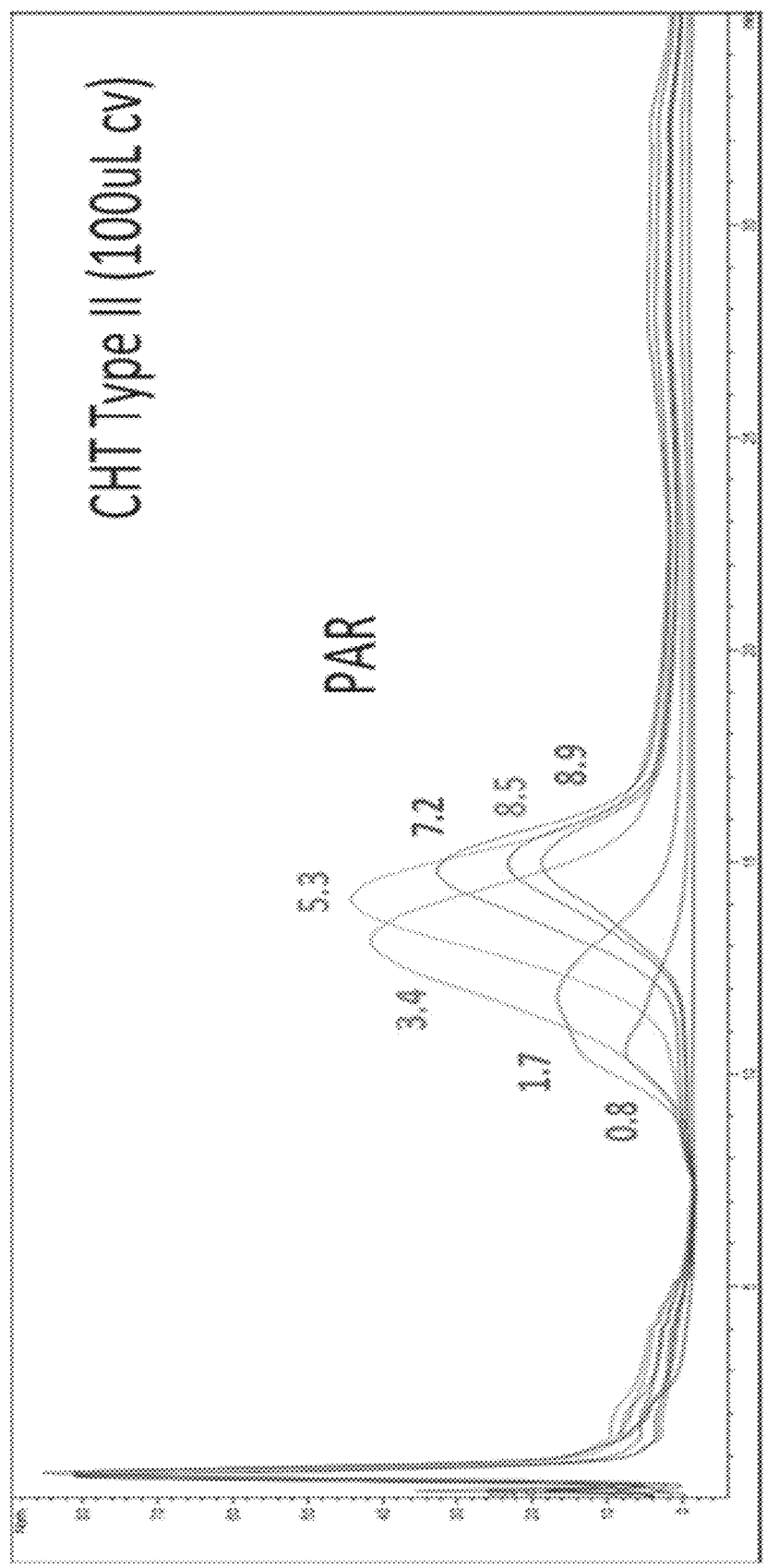
FIG. 6A depicts hydroxyapatite chromatography of chemical conjugates with increasing numbers of peptides. The absorbance at 280 nm of the eluate for each conjugate is shown (x-axis=minutes, y-axis=absorbance (normalized)).
Figure 6B:
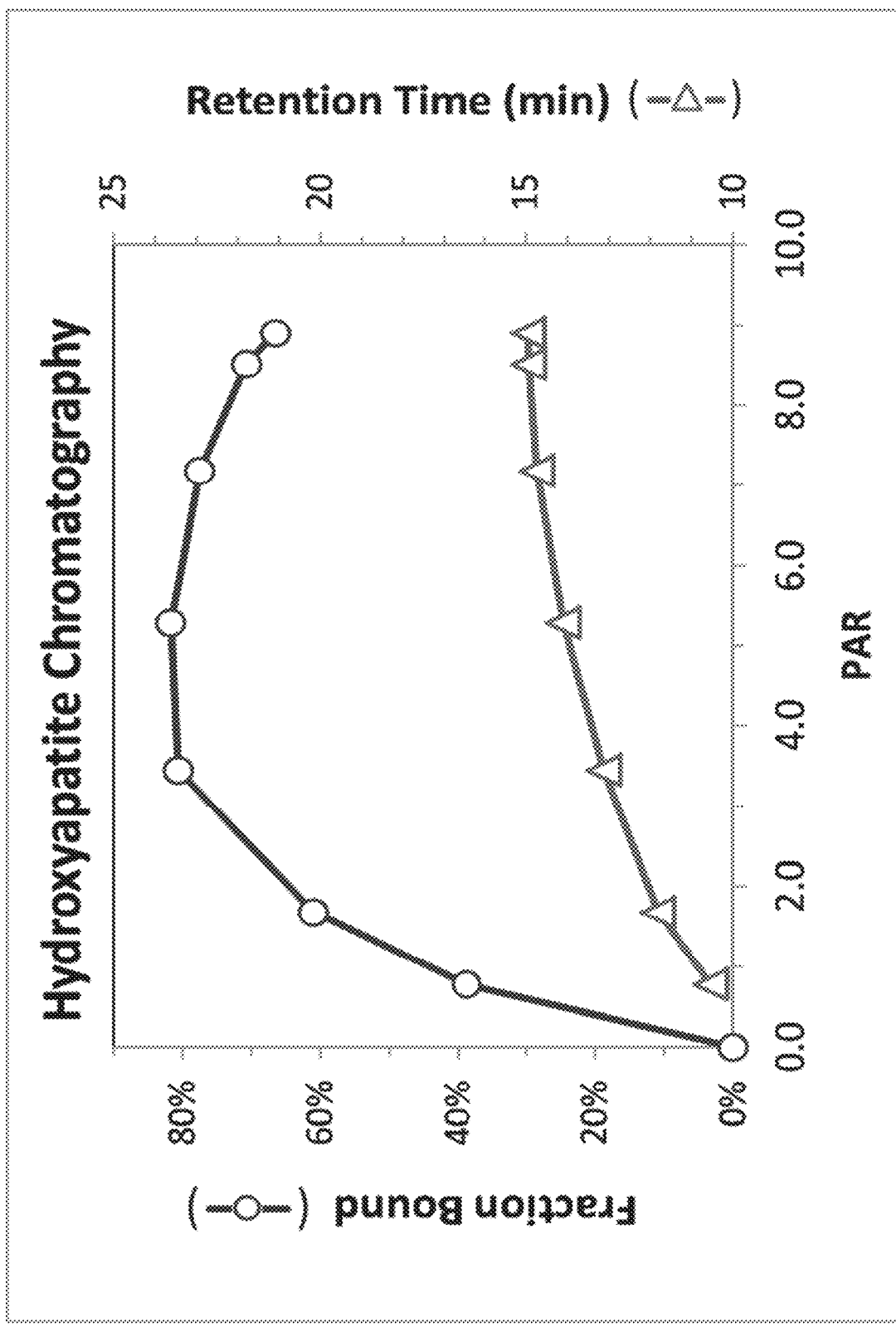
FIG. 6B depicts the fraction of analyte bound (upper curve, circles, scale left) and the retention time (lower curve, triangles, scale right) as a function of the number of peptides conjugated as determined by SDS-PAGE.

Example 4: Effect of a Range of Peptide Loading on Binding to Hydroxyapatite In this example, a series of D10 peptide chemical conjugates with varying numbers of peptides described in Example 1 was chromatographed on a CHT type II column as described in Example 3. The $A_{280}$ profiles and a plot of the fraction of conjugate bound and the peak retention times are shown in FIG. 6A. As seen in FIG. 6B, the amount of conjugate bound to the column increased up to PAR 3.8, leveled off, and began to decrease with a greater number of peptides. In contrast, the retention time of the conjugate (indicating the strength of the interaction) with the resin increased with increasing number of peptides up to 9.

Figure 7:
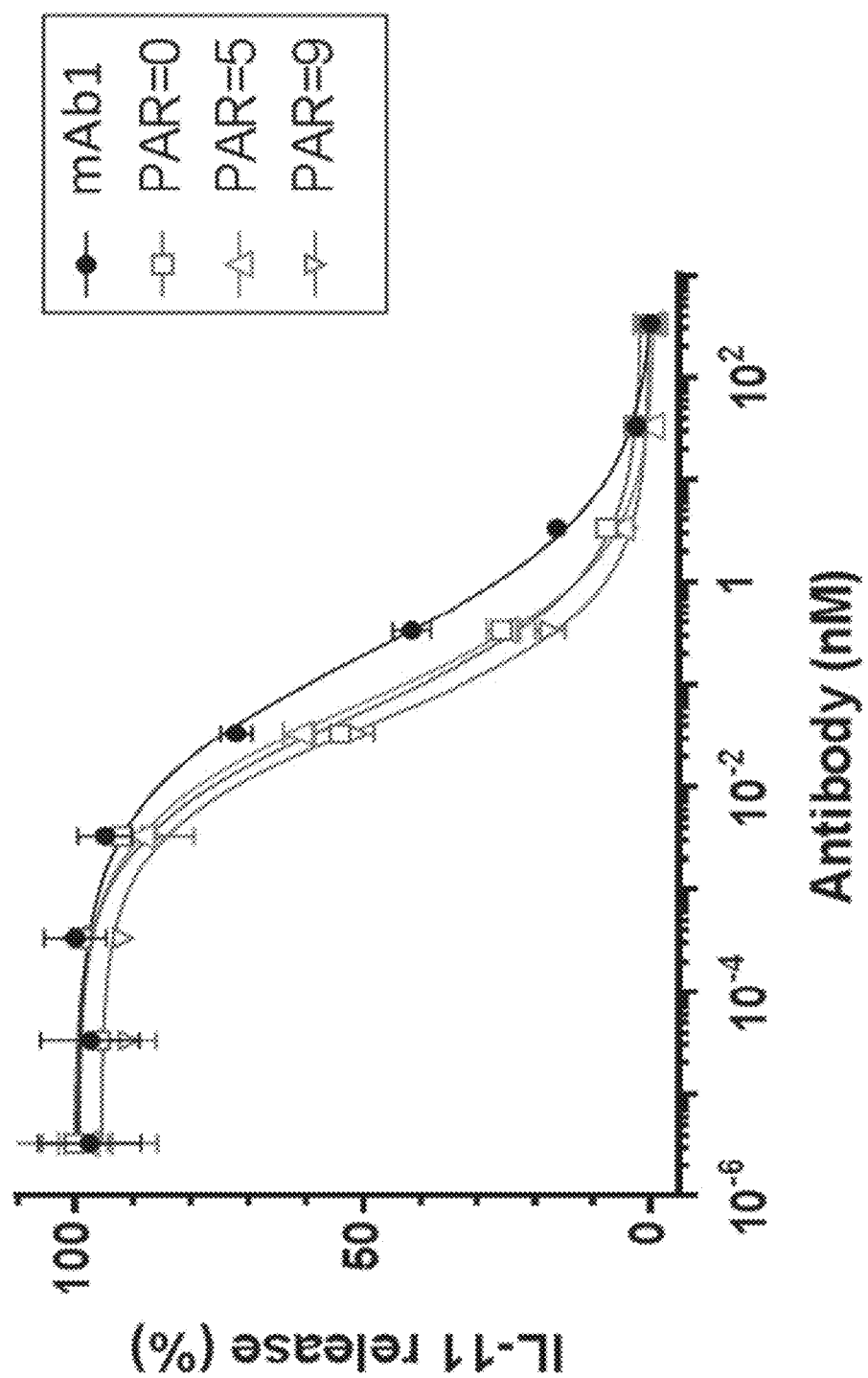
FIG. 7 depicts an in vitro TGFβ neutralization assay performed with A549 cells with a control conjugate (PAR=0) and conjugates with an average of 4 or 9 peptides compared to unmodified mAb1.
Figure 8A:
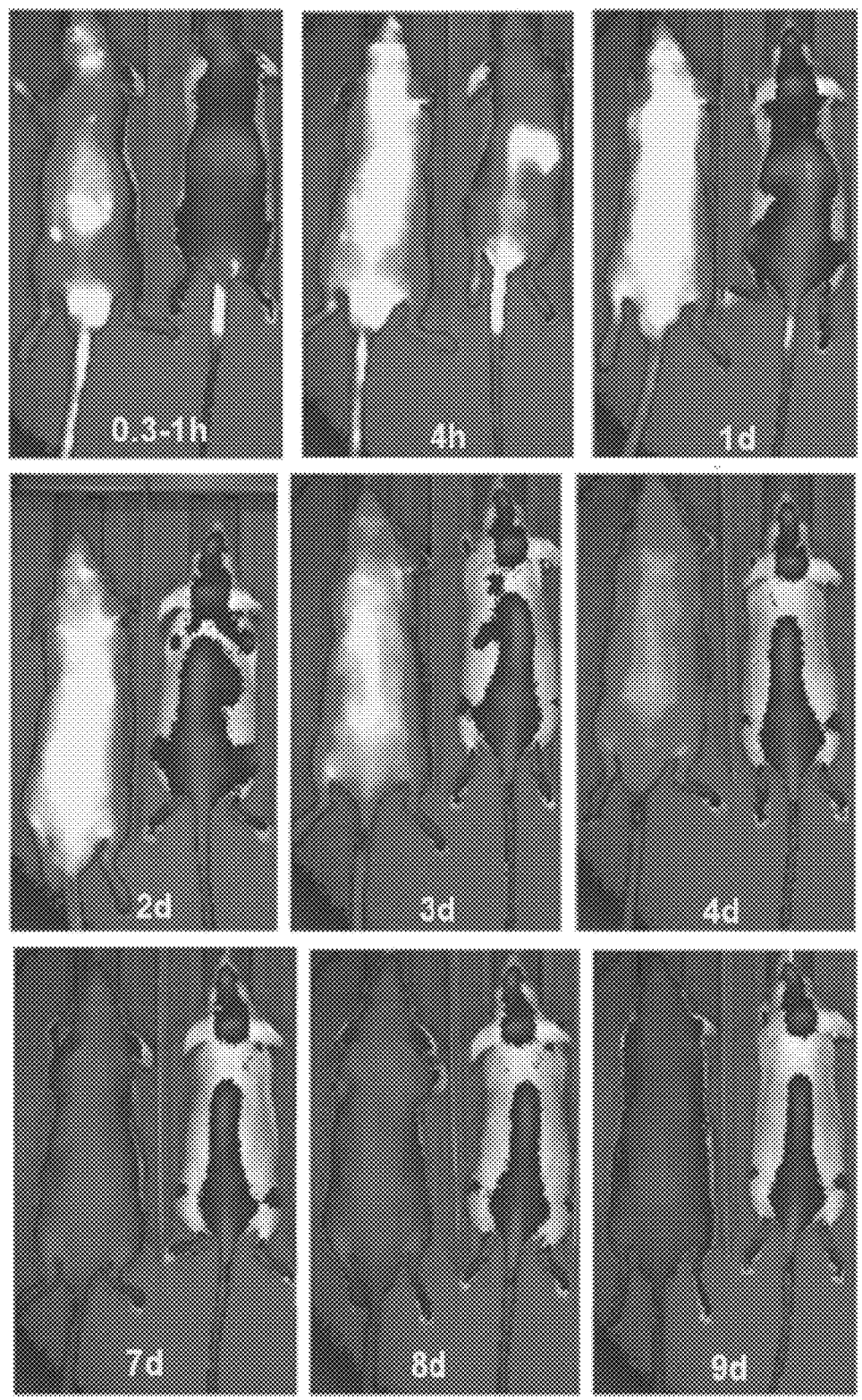
FIG. 8A depicts the time-dependent biodistribution of fluorophore-labeled mAb1 and a chemical conjugate at 1 mg/kg (1 mpk) containing approximately 4.5 peptides. The times at which the animals were imaged are indicated in each panel. Per photograph, the left mouse received mAb1, and right mouse received the chemical conjugate. Image intensities have been adjusted to reveal differences in distribution.
Figure 8B:
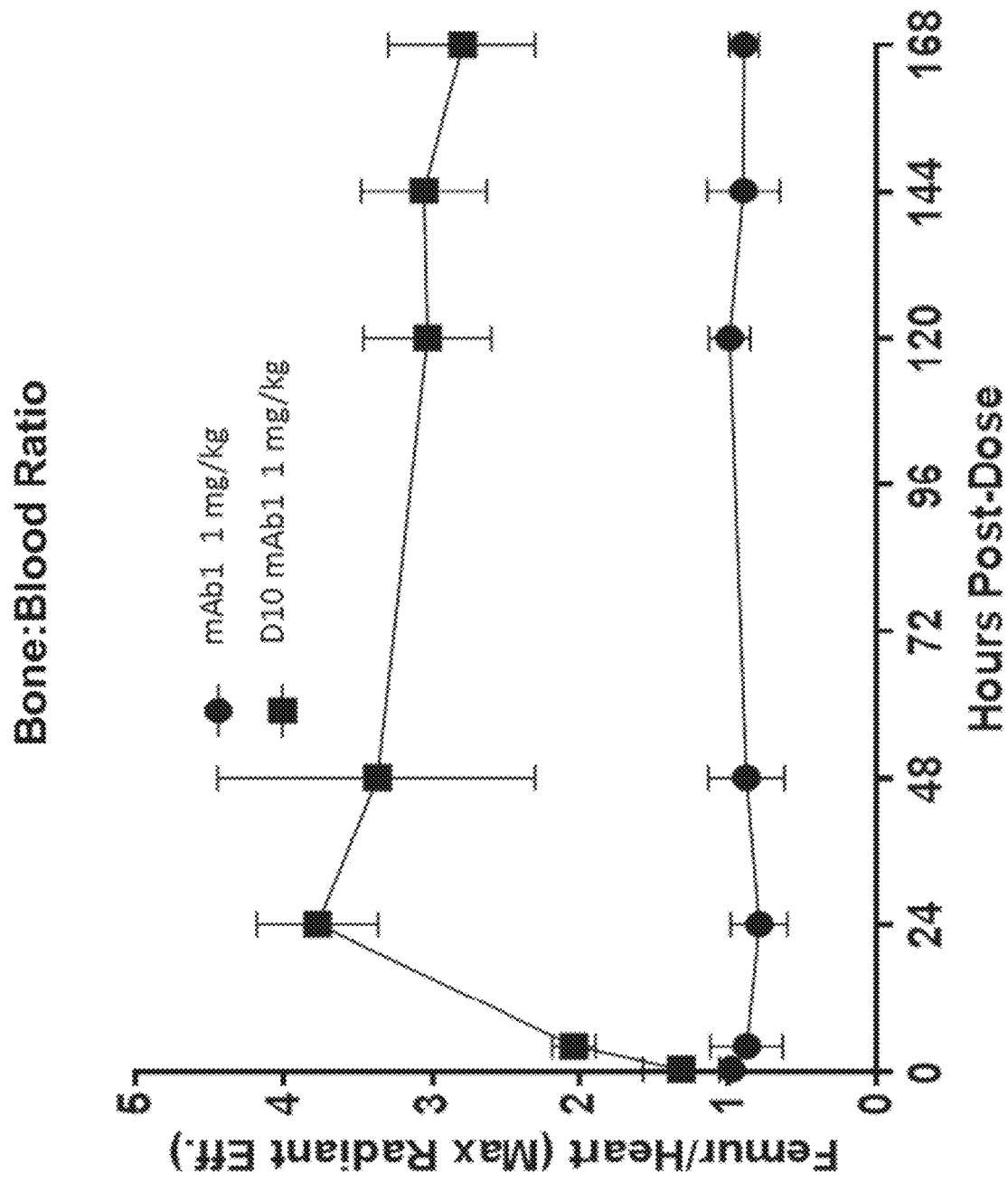
FIG. 8B depicts the ratio of fluorescence found in the region of interest corresponding to the distal femur and the region of interest corresponding to the heart in the images shown in FIG. 8A. Circles correspond to mAb1 antibody and squares correspond to the D10 peptide conjugated with mAb1 (D10 mAb1).

Example 5: Effect of D10 Peptide Chemical Conjugation to mAb1 on its Potency in Neutralizing TGF-β1 In Vitro In this example, a set of three mAb1-D10 conjugates, such as shown in FIG. 2, was prepared as described in Example 1. A control conjugate was prepared by omitting the D10-maleimide peptide during conjugation. By SDS-PAGE analysis, such as depicted in FIG. 3, the peptide loading (PAR) was determined to be 0, 5 or 9 for these three conjugates. The ability of these conjugates to inactivate TGF-β1 was then determined by coincubation with TGF-β1 for 1 hr. Serial dilutions in growth medium were then applied to human A549 cells expressing the human TGF-β1 receptor followed by overnight incubation. The cellular response to active TGF-β1 was then determined by release of IL-11 into the growth medium, which was detected by an ELISA assay specific for IL-11. The IL-11 response for the three conjugates and a mAb1 control is depicted in FIG. 7. In all cases, the half-maximal inhibition of IL-11 release ($EC_{50}$) occurred around 0.1 nM antibody. Both conjugates (PAR=5 and PAR=9) and the mock conjugate lacking peptide (PAR=0) showed slightly better inhibition than mAb1. The number of conjugated peptides had no effect on the $EC_{50}$.

Example 6: Effect of Conjugated D10 Peptide on Biodistribution of mAb1 Administered to Mice A D10-mAb1 chemical conjugate was prepared in a similar fashion as described in Example 1, such as shown in FIG. 2. mAb1 (19.6 mg) was exchanged into degassed borate buffer, reacted with 10.6 eq (1.06 μmol) DTT for 1.5 h at 37° C. followed by reaction without buffer exchange with 6 eq D10 peptide (Ac-D10-C2-PEG12-C6-maleimide) under argon for 1.5 hr at 25° C. Unconjugated free thiols were blocked by addition of 12 eq N-ethylmaleimide followed by incubation for 30 min at 25° C. The final product was purified by ultrafiltration. The peptide-to-antibody ratio was determined using SDS-PAGE (PAR-4.8). The light chain showed trace amounts of a band corresponding to the addition of a single peptide to a light chain cysteine residue.

The conjugate and mAb1 antibody control were separately labeled with AlexaFluor®750 (Thermo Fisher) using conditions as described by the manufacturer. The fluorescent test articles were administered to SKH-1 hairless mice which were imaged with an IVIS instrument (Perkin Elmer) immediately following administration (0.3-1 hr), and after 4 hr, and 1, 2, 3, 4, 7, 8, and 9 days. The images of mice injected with 1 mg/kg labeled mAb1 and conjugate are depicted in FIG. 8A. The fluorescence of labeled mAb1 was uniformly distributed throughout the body, and this pattern was maintained but decreased in intensity over 9 days. In contrast, after 1 day the mAb1-D10 conjugate was concentrated at or near the dorsal midline, limbs and tail, consistent with localization to bone but was at nearly undetectable levels elsewhere in the body. Consistent with the images of FIG. 8A, ratios of distal femur fluorescence compared to heart fluorescence measured in the images of FIG. 8A were significantly elevated ($P<0.05$) for the mAb1-D10 conjugate compared to control by 24 hr and remained significantly elevated through 168 hr (see FIG. 8B). This distribution was maintained over 9 days with only a minor change in intensity.

Example 7: Preparation of Recombinant Murine Anti-TGFβ-D10 Antibody Fusion Variants A set of recombinant anti-TGFβ-D10 peptide fusion variants as depicted in FIGS. 9A and 9B was prepared as described below.

Heavy and Light Chain Expression Vector Constructs

A panel of plasmids for expressing mAb1 heavy and light chains with D10 peptides at various positions was generated. In addition, two plasmids were also generated for wild type mAb1 heavy and light chain without D10 peptides. All codon-optimized sequences were generated synthetically (GeneArt), flanked with appropriate restriction enzyme sites designed in-frame for the cloning purpose. Three gene fragments, encoding mouse IgG1 constant regions with or without C-terminal D10 peptides and mAb1 wild type complete light chain, were cloned into an empty episomal mammalian expression vector pFF, an analog of the pTT vector described by Durocher et al., (2002, *Nucl. Acids Res.* 30(2): E9) to create "mIgG1_CH123_pFF", "mIgG1_CH123D10_pFF," and "mAb1_VLCL_pFF" using ApaL/HindIII restriction enzymes and subsequent ligation. Gene fragments encoding variable regions with or without N-terminal D10 peptide were cloned into the vectors using ApaLI/EagI for heavy chains and ApaLI/MfeI for the light chain. Gene fragments encoding the constant region of the mouse Ig kappa light chain with C-terminal D10 and different lengths of G4S (SEQ ID NO: 9) spacer were cloned into "mAb1_VLCL_pFF," using MfeI/HindIII to replace the wild type constant region. Expected correct DNA sequence of each construct was confirmed by DNA sequencing (ACGT, Inc.).

Fusion Variant Assembly and Expression

The fusion variants were produced by selecting one of each of the heavy and light chain vectors for co-transfection in order to yield the fusion variants and a no-peptide control as described in Table 1. "PAR" (peptide-to-antibody ratio) reflects the total number of peptides expected to be appended to the final expressed antibody on both its heavy and light chains. Fusion variant ID "mAb1 F1" represents a "wildtype" ("wt") construct that is substantially identical to the mAb sequence without modification. "HC" indicates the heavy chain of mAb1, "LC" indicates the light chain of mAb1, "D10" indicates the D10 peptide (SEQ ID NO: 1), and "G4S" indicates a spacer sequence consisting of gly-gly-gly-gly-ser (SEQ ID NO: 9) incorporated in some constructs.

TABLE 1

Recombinant fusion variants of mAb1 with D10

| Variant ID | Heavy Chain Construct | SEQ ID NO: | Light Chain Construct | SEQ ID NO: | PAR |
|---|---|---|---|---|---|
| mAb1 F1 | HC | 2 | LC | 6 | 0 |
| mAb1 F2 | HC | 2 | D10-LC | 7 | 2 |
| mAb1 F3 | HC | 2 | LC-D10 | 8 | 2 |
| mAb1 F4 | HC | 2 | LC-(G4S)-D10 | 11 | 2 |
| mAb1 F5 | HC | 2 | LC-(G4S)$_2$-D10 | 12 | 2 |
| mAb1 F6 | HC-D10 | 3 | LC | 6 | 2 |
| mAb1 F7 | HC-D10 | 3 | D10-LC | 7 | 4 |
| mAb1 F8 | HC-D10 | 3 | LC-D10 | 8 | 4 |
| mAb1 F9 | HC-D10 | 3 | LC-(G4S)-D10 | 11 | 4 |
| mAb1 F10 | HC-D10 | 3 | LC-(G4S)$_2$-D10 | 12 | 4 |
| mAb1 F11 | D10-HC | 4 | LC | 6 | 2 |
| mAb1 F12 | D10-HC | 4 | D10-LC | 7 | 4 |
| mAb1 F13 | D10-HC | 4 | LC-D10 | 8 | 4 |
| mAb1 F14 | D10-HC | 4 | LC-(G4S)-D10 | 11 | 4 |
| mAb1 F15 | D10-HC | 4 | LC-(G4S)$_2$-D10 | 12 | 4 |
| mAb1 F16 | D10-HC-D10 | 5 | LC | 6 | 4 |
| mAb1 F17 | D10-HC-D10 | 5 | D10-LC | 7 | 6 |
| mAb1 F18 | D10-HC-D10 | 5 | LC-D10 | 8 | 6 |
| mAb1 F19 | D10-HC-D10 | 5 | LC-(G4S)-D10 | 11 | 6 |
| mAb1 F20 | D10-HC-D10 | 5 | LC-(G4S)$_2$-D10 | 12 | 6 |

To assess the ability of the desired recombinant fusion variants to be expressed, sixteen variants from Table 1 were evaluated by cotransfection into Expi293F™ cells (Life Technologies) using conditions as described by the manufacturer. After 4 days, expression was determined by SDS-PAGE of conditioned medium. All of the variants were expressed at levels estimated to be between 10-30 μg/mL. Slightly higher levels were observed after 5 and 7 days but expression levels were dependent on the variant. WT (mAb1 F1), HC-D10:LC-D10 (mAb1 F8), and HC-D10: LC-G4S-D10 (mAb1 F9) showed particularly high expression, while D10-HC:D10-LC (mAb1 F12) expressed poorly.

Larger-Scale Expression

All twenty recombinant mAb1-D10 fusion variants were expressed in Expi293-F cells at 30 mL scale. Conditioned media (CM) were harvested on day 6 and expression levels assessed by non-reducing SDS-PAGE. Somewhat higher levels of expression (30-150 μg/ml) were observed compared to the initial assessment, but the relative expression levels were consistent with the smaller scale transfections.

Example 8: Recombinant mAb1-D10 Fusion Variant Characterization

Expression Level and TGF-β1 Binding

Quantitation of the expression level and the capability of recombinant mAb1-D10 fusion variants to bind TGF-β1 were assessed using an Octet® QK384. Octet® biosensors for murine IgG were dipped into conditioned medium diluted 1:10 in sample diluent (PBS, pH 7.4 containing 0.01% BSA and 0.02% Tween 20) or 2-fold serial dilutions of a purified mAb1 standard over the range of 1.25 to 100 μg/mL. Binding data were collected for 2 min while shaking the samples at 500 rpm. Titers were calculated using a 4-parameter fit of the initial binding rates and comparison to those obtained from the standards. The biosensors were then washed with diluent for 1 min to remove any medium and reestablish a baseline and then dipped into wells containing 40 nM TGF-β1 for 3 min at 1000 rpm to follow binding. This was followed by a dissociation step by transfer of the sensors to diluent for 3 min at 1000 rpm. As seen in Table 2, the concentrations for the fusion variants in the media ranged from 11 to 178 μg/mL ("Octet Conc.") and generally matched trends observed by SDS-PAGE ("Expression Level"). In addition, all of the fusion variants were capable of binding TGF-β1, suggesting the presence of D10 peptide at any of the positions indicated did not seriously affect antigen binding.

Mouse FcRn Binding

Mouse FcRn binding by the recombinant mAb1-D10 fusion variants was assessed using an Octet QK384. All steps were performed at 1000 rpm. Conditioned medium diluted to achieve an antibody concentration of 10 μg/mL was contacted by anti-murine IgG Fv biosensors for 5 minutes. The biosensors were then dipped into PBSP pH 6.0 (50 mM sodium phosphate pH 6.0, 150 mM sodium chloride, 0.005% surfactant P20) to establish a baseline. The sensors were then transferred to wells containing soluble mouse FcRn diluted to 1 μM in PBSP pH 6.0 for 3 min followed by 3 min dissociation in wells containing PBSP pH 6.0. As indicated in Table 2, all variants bound mouse FcRn.

Protein G Binding

Binding by the recombinant mAb1-D10 fusion variants to protein G was assessed using an Octet QK384. Protein G biosensors were dipped into wells containing conditioned medium diluted to 10 μg/mL antibody in sample diluent and signal followed for 3 min at 1000 rpm. As indicated in Table 2, all of the variants bound protein G.

TABLE 2

| Characterization of mAb1-D10 fusion variants | | | | | | | | |
|---|---|---|---|---|---|---|---|---|
| Variant ID | Heavy Chain | Light Chain | PAR | Octet ® Conc. (μg/mL) | Expression Level | TGF-β1 Binding | Mouse FcRn Binding | Protein G Binding |
| mAb1 F1 | wt-HC | wt-LC | 0 | 85 | ++ | + | + | +++ |
| mAb1 F2 | wt-HC | D10-LC | 2 | 53 | ++ | + | + | ++ |
| mAb1 F3 | wt-HC | LC-D10 | 2 | 50 | ++ | + | + | + |

TABLE 2-continued

Characterization of mAb1-D10 fusion variants

| Variant ID | Heavy Chain | Light Chain | PAR | Octet® Conc. (μg/mL) | Expression Level | TGF-β1 Binding | Mouse FcRn Binding | Protein G Binding |
|---|---|---|---|---|---|---|---|---|
| mAb1 F4 | wt-HC | LC-(G4S)-D10 | 2 | 52 | ++ | + | + | + |
| mAb1 F5 | wt-HC | LC-(G4S)$_2$-D10 | 2 | 34 | + | + | + | + |
| mAb1 F6 | HC-D10 | wt-LC | 2 | 178 | ++++ | + | + | ++ |
| mAb1 F7 | HC-D10 | D10-LC | 4 | 46 | + | + | + | ++ |
| mAb1 F8 | HC-D10 | LC-D10 | 4 | 117 | +++ | + | + | + |
| mAb1 F9 | HC-D10 | LC-(G4S)-D10 | 4 | 156 | ++++ | + | + | + |
| mAb1 F10 | HC-D10 | LC-(G4S)$_2$-D10 | 4 | 100 | +++ | + | + | + |
| mAb1 F11 | D10-HC | wt-LC | 2 | 36 | + | + | + | ++ |
| mAb1 F12 | D10-HC | D10-LC | 4 | 11 | + | + | + | ++ |
| mAb1 F13 | D10-HC | LC-D10 | 4 | 36 | + | + | + | + |
| mAb1 F14 | D10-HC | LC-(G4S)-D10 | 4 | 34 | + | + | + | + |
| mAb1 F15 | D10-HC | LC-(G4S)$_2$-D10 | 4 | 27 | + | + | + | + |
| mAb1 F16 | D10-HC-D10 | wt-LC | 4 | 36 | + | + | + | ++ |
| mAb1 F17 | D10-HC-D10 | D10-LC | 6 | 23 | + | + | + | ++ |
| mAb1 F18 | D10-HC-D10 | LC-D10 | 6 | 31 | + | + | + | + |
| mAb1 F19 | D10-HC-D10 | LC-(G4S)-D10 | 6 | 40 | + | + | + | + |
| mAb1 F20 | D10-HC-D10 | LC-(G4S)$_2$-D10 | 6 | 28 | + | + | + | + |

SDS-Page

Figure 10:
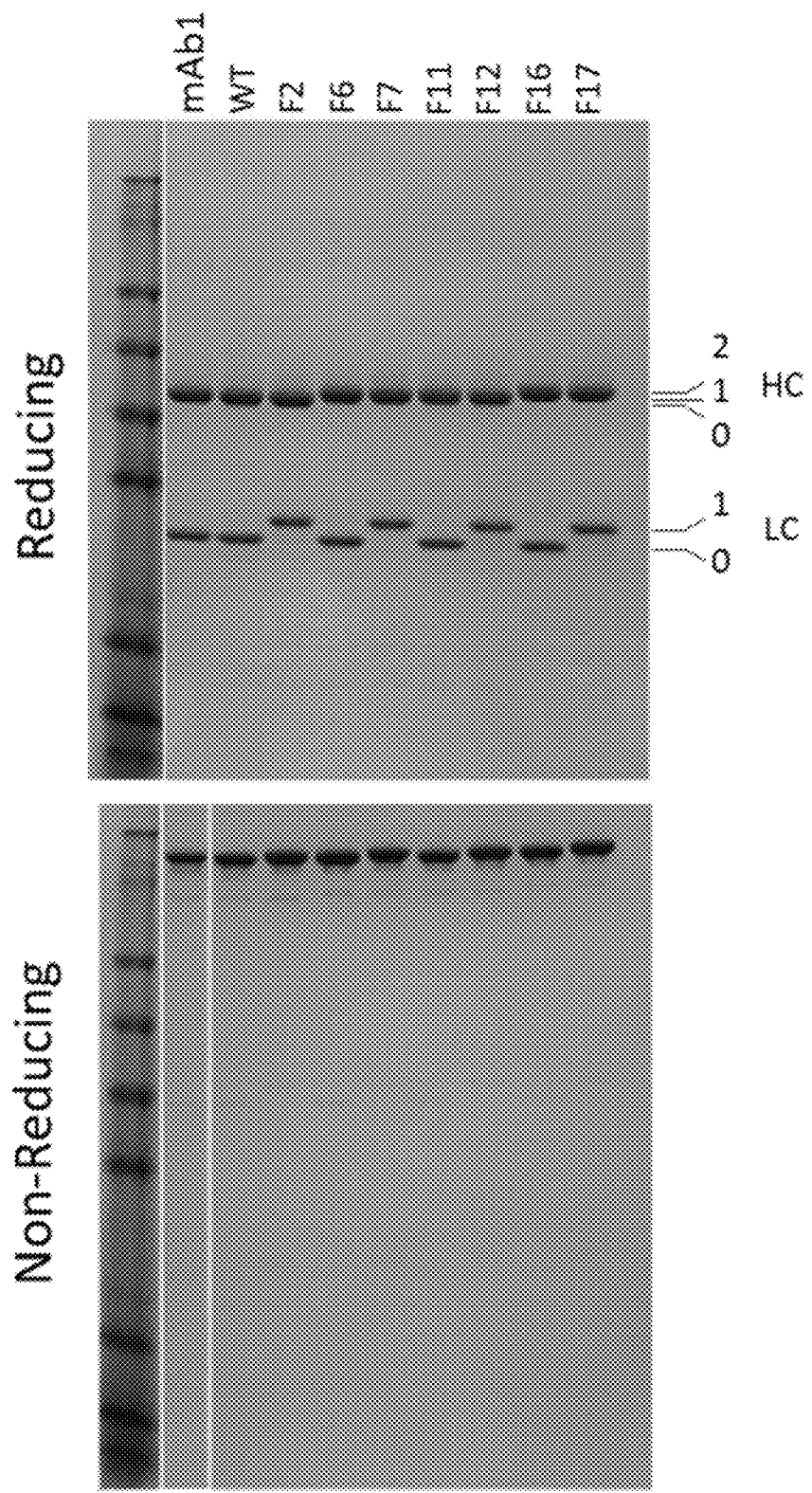
FIG. 10 depicts SDS-PAGE of the indicated purified recombinant mAb1 fusion variants under reducing (upper gel) or non-reducing (lower gel) conditions.

Purified WT construct and recombinant fusion variants mAb1 F2, mAb1 F6, mAb1 F7, mAb1 F11, mAb1 F12, mAb1 F16, and mAb1 F17 were analyzed on 4-20% Tris-Glycine SDS-PAGE gels (Novex, Life Sciences) under reducing and non-reducing conditions and stained with Coomassie Blue. A visible light image collected by a ProteinSimple® imager is depicted in FIG. 10. A small reduction in the mobility of the heavy and/or light chain was observed which matched the expected presence and number of D10 peptides on each. Impurities and covalent aggregates were not detectable.

Thermal Stability by Differential Scanning Fluorimetry (DSF)

Figure 11:
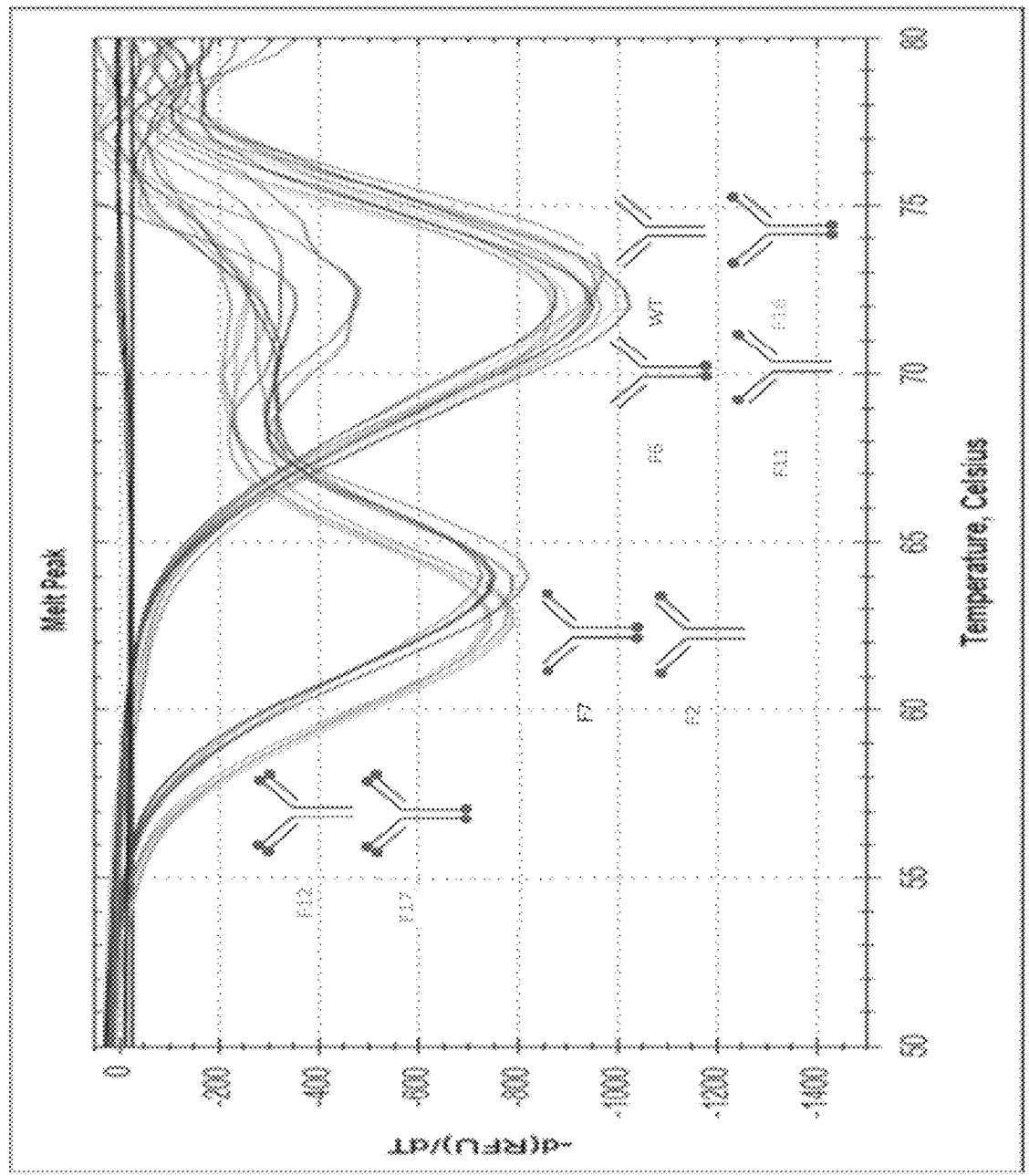
FIG. 11 depicts thermostability of recombinant mAb1 fusion variants as determined by differential scanning fluorimetry (DSF). The transition to a partially-denatured form at each temperature is detected by an increase in dye fluorescence. The slope of fluorescence increase with temperature (−d(RFU)/dT) was calculated and is displayed versus the temperature of the sample. The rate of the denaturation is maximal at the minima of the curves which represent the midpoint of the thermal transitions (Tm). For reference, the structures of each of the recombinant mAb1 fusion variants are shown diagrammatically.
Figure 12A:
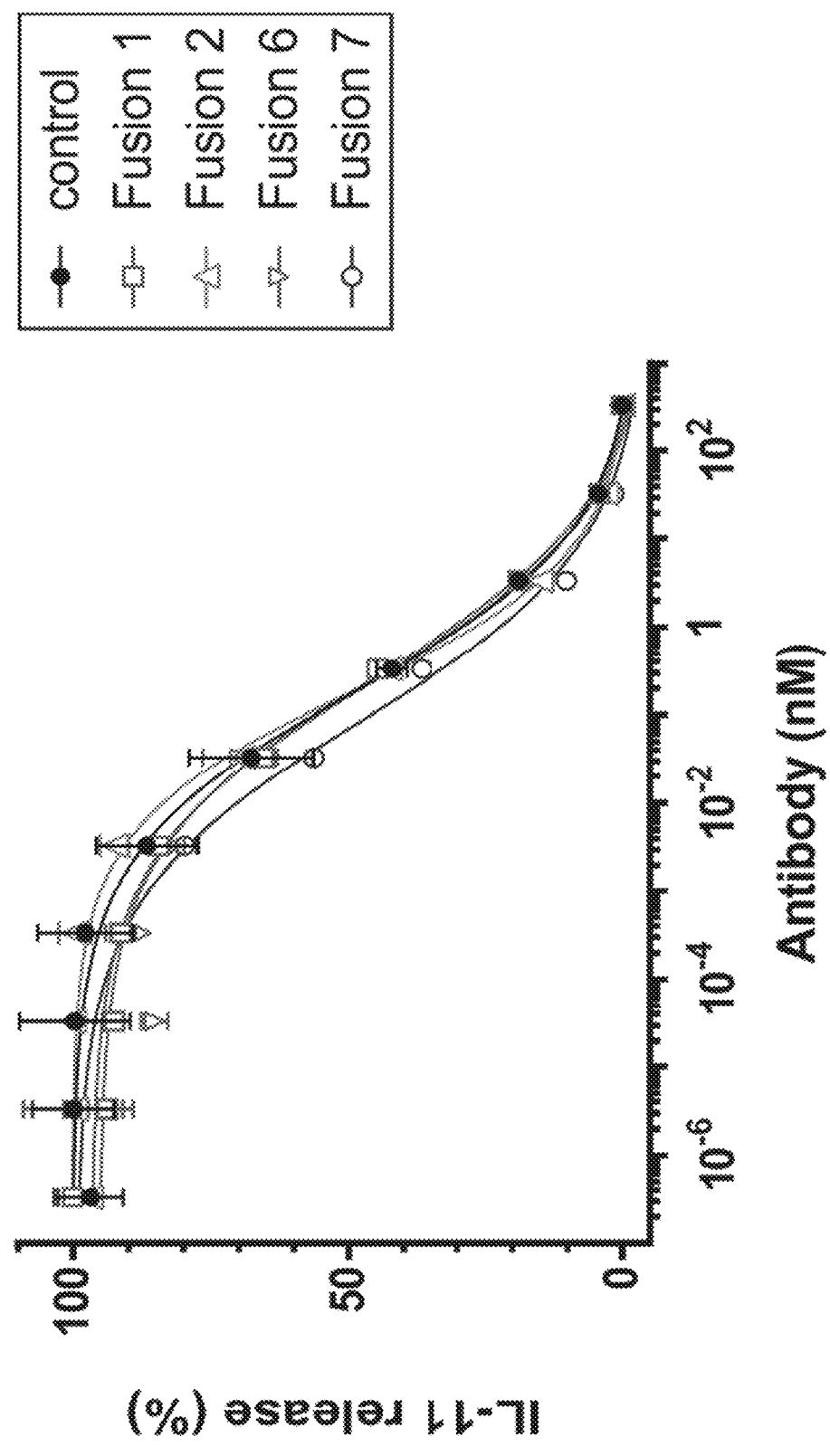
FIGS. 12A and 12B depict the neutralization of TGFβ in eliciting the production of IL-11 by A549 cells in vitro by eight recombinant mAb1 fusion variants shown diagrammatically in FIG. 9B.
Figure 12B:
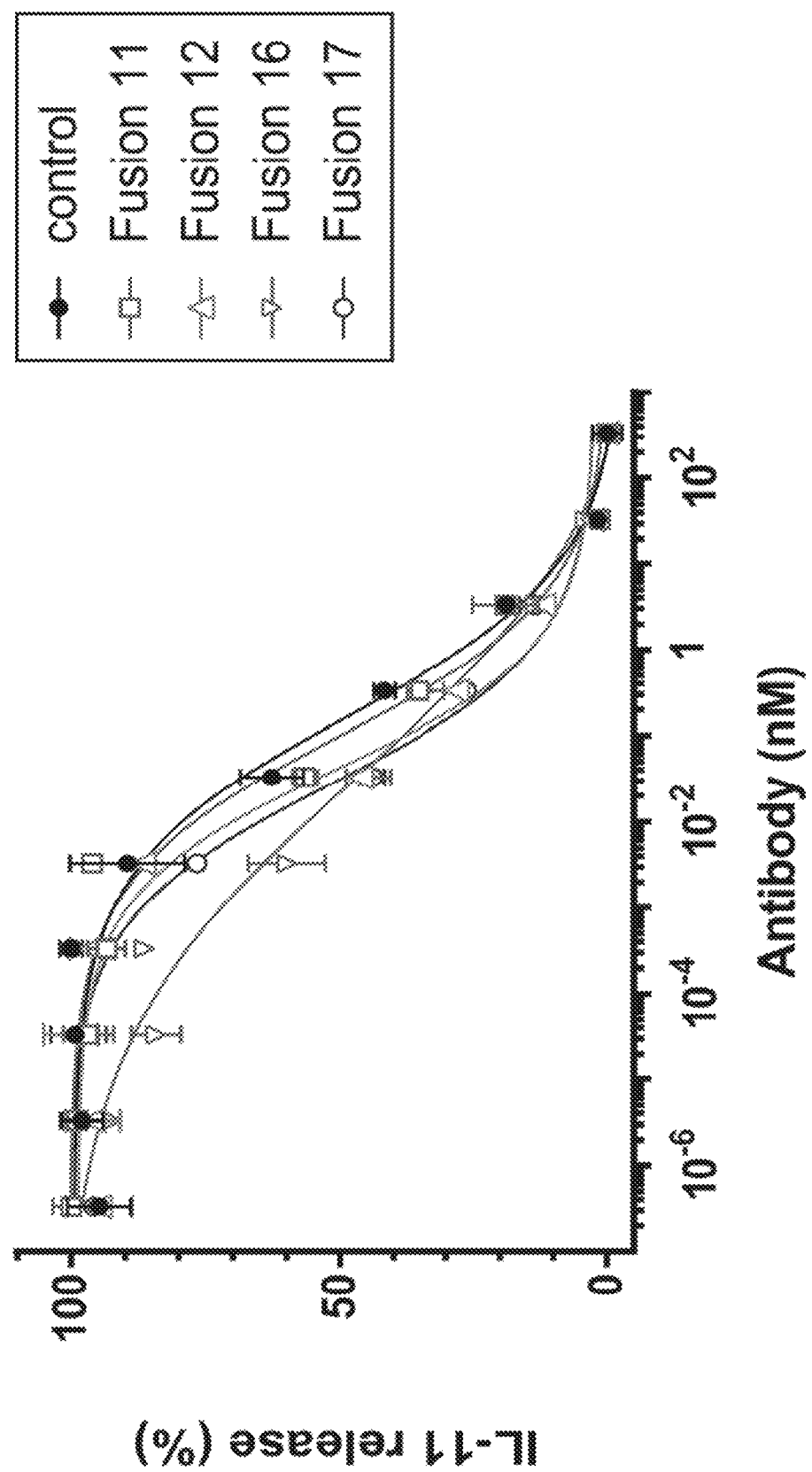
Figure 13:
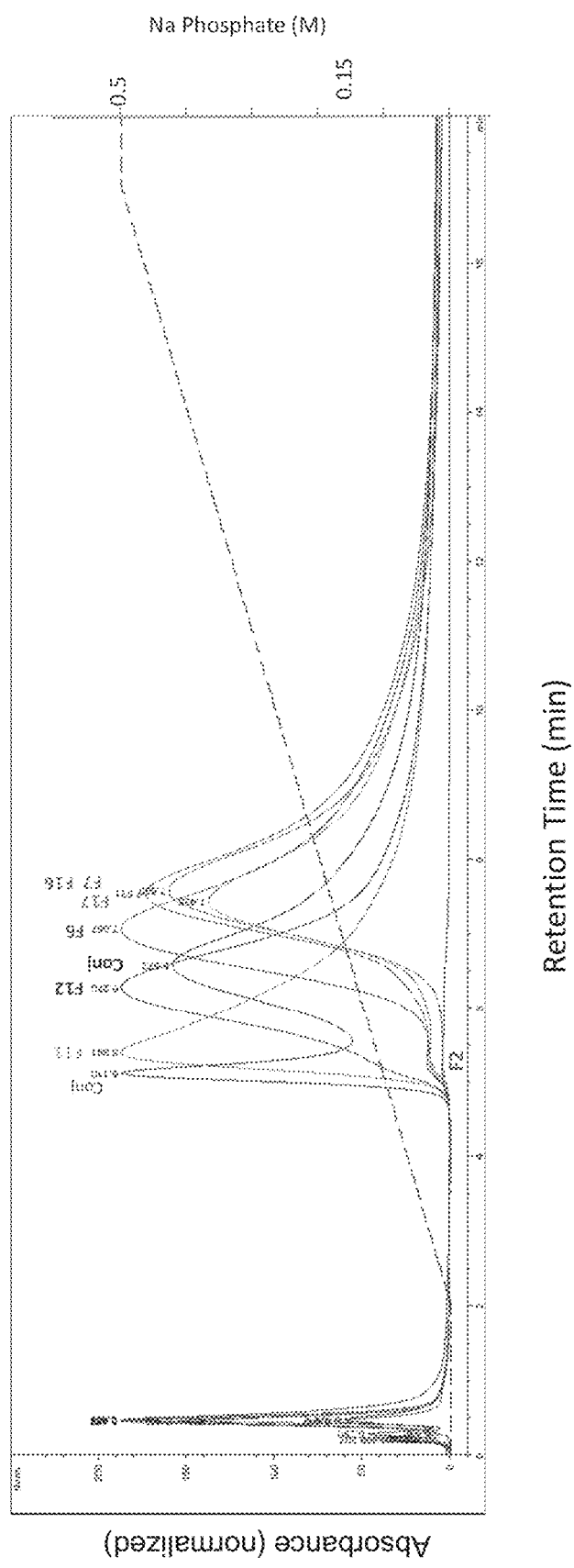
FIG. 13 depicts the affinity of recombinant mAb1 fusion variants and mAb1 chemical conjugates to hydroxyapatite as assessed by column chromatography on a column of ceramic hydroxyapatite.

Thermal stabilities of several recombinant mAb1-D10 fusion variants representing all possible combinations of D10 peptides at the termini on the heavy and light chains were determined by differential scanning fluorimetry using SYPRO® Orange (Thermo Scientific) as a reporter dye. It is generally accepted that the stability of proteins at higher temperature is predictive of their stability under typical storage conditions and thus can be used to assess their suitability for manufacture and use as therapeutics. Thermal stability can be assessed with dyes which exhibit an increase in fluorescence upon binding hydrophobic regions exposed by unfolding of protein structure on real-time PCR instruments (Lo et al., 2004, Anal. Biochem. 332(1): 153-9). The fluorescence of samples (10 μL at 0.5 mg/ml protein) containing a 1:1000 dilution of SYPRO® Orange was followed while raising the temperature on a CFX96 Real-time PCR Detection System. Data were analyzed using CFX Manager 3.0 (Bio-Rad Laboratories). FIG. 11 depicts the rate of change of the fluorescence with temperature for several variants. The rate of change is typically used rather than absolute fluorescence in order to separate out the binding of dye to portions of the protein structure which are unaffected by structural transitions. A negative displacement reflects an increase in the rate of fluorescence change and a minimum represents the midpoint of the transition to an unfolded state ("Tm"). Several of the variants tested (mAb1 F6, mAb1 F11, mAb1 F16) showed Tm profiles indistinguishable from the unmodified antibody control ("WT"=mAb1 F1). Two others (mAb1 F2 and mAb1 F7) showed a significant decrease in the Tm for the major transition. Two variants (mAb1 F12 and mAb1 F17) showed the lowest Tm values. Notably, all four of the recombinant mAb1-D10 fusion variants containing a D10 peptide at the N-terminus of the light chain showed a significant decrease in Tm suggesting placement of the peptide at this position on the mAb1 antibody destabilizes its structure. Conversely, placement of the D10 peptide on either terminus of the heavy chain did not correlate with any change in Tm. The Tm values of the predominant transitions for several fusion variants observed as depicted in FIG. 11 are tabulated in Table 3.

TABLE 3

Differential scanning fluorimetry of expressed recombinant fusion variants

| Variant ID[A] | (5'-HC-3'):(5'-LC-3') | PAR | Tm |
|---|---|---|---|
| mAb1 F1[B] | WT | 0 | 72.5 |
| mAb1 F2 | WT-HC:D10-LC | 2 | 64.0 |
| mAb1 F6 | HC-D10:WT-LC | 2 | 72.3 |
| mAb1 F7 | HC-D10:D10-LC | 4 | 64.0 |
| mAb1 F11 | D10-HC:WT-LC | 2 | 72.0 |
| mAb1 F12 | D10-HC:D10-LC | 4 | 62.7 |
| mAb1 F16 | D10-HC-D10:WT-LC | 4 | 72.0 |
| mAb1 F17 | D10-HC-D10:D10-LC | 6 | 62.5 |

[A]see Table 2; [B]mAb1 F1 is a recombinant version of mAb1.

Example 9: Potency of Recombinant mAb1-D10 Fusion Variants in Neutralizing TGF-β1 In Vitro The potency of recombinant mAb1-D10 fusion variants in neutralizing TGF-β1 activity was determined by inhibition of the secretion of IL-11 by A549 tumor cells in vitro in response to TGF-β1 added to the medium. The procedure was performed as described in Example 3. Several representative fusion variants from Example 7 were selected on the basis of their affinity for protein G (as an indicator of their ease of purification). The TGF-β1 inhibition profiles for eight variants (mAb1 F1, mAb1 F2, mAb1 F6, mAb1 F7, mAb1 F11, mAb1 F12, mAb1 F16, and mAb1 F17) are depicted in FIGS. 12A and 12B. All of the fusion proteins showed a similar $EC_{50}$ as the mAb1 control.

Example 10: Binding of TGF-β1 by Recombinant Fusion Variants

Recombinant mAb1-D10 fusion variants of Example 7 were also quantitatively assessed for TGF-β1 binding using surface plasmon resonance (SPR) as detected by Biacore. Samples containing purified variants were passed over a sensor chip with amine-coupled TGF-β1 to determine the equilibrium constant, KD. A target immobilization level of less than 100 response units (RU) of TGF-β1 was chosen to minimize the potential for avidity effects arising from binding adjacent TGF-β1 molecules on the chip. The level of immobilization was determined by the change in response units after NHS/EDC activation of the chip surface, but before quenching with ethanolamine. The fusion variants, WT fusion variant F1, and mAb1 control were diluted to 30, 10, 3, 1 and 0.37 nM in HBS-EP buffer and passed over the TGF-β1 chip at 30 μL/min for 3 min, followed by 5 min dissociation in the same buffer. Between runs, the chip surface was regenerated to remove any bound antibody by passing two 30 sec injections of 40 mM HCl over the chip at a flow rate of 75 μL/min. As shown in Table 4, the equilibrium constants (KD) for all of the fusion variants and the WT construct (F1) were within 2.4-fold of the mAb1 control. Unexpectedly, the maximum signal (RU) elicited by the fusion variants decreased with increasing number of peptides, with variant F17 (D10-HC-D10/D10-LC, PAR=6) showing the lowest signal. This is in contrast to the A549 cell potency assay as described in Example 9 which showed all the tested fusion variants to be comparable to or more potent than either mAb1 or the WT construct in neutralizing TGF-β1. A possible explanation of this decline may reflect electrostatic repulsion between the chip matrix (carboxymethyl dextran) and the negatively charged D10 peptides.

TABLE 4

| Equilibrium constants for mAb1-D10 fusion variants binding to TGF-β1 by Biacore analysis | | | | | | |
|---|---|---|---|---|---|---|
| Variant ID[A] | Sample | PAR | Kinetic Fit Conc. Range | $K_a(\times10^5 M^{-1}s^{-1})$ | $K_d(\times10^{-3}s^{-1})$ | TGFβ1 $K_D$ (nM) |
| mAb1 | unmodified mAb | 0 | 90-3 nM | 1.67 | 1.00 | 6.00 |
| mAb1 F1 | WT-HC: WT-LC | 0 | 30-3 nM | 3.38 | 0.85 | 2.51 |
| mAb1 F2 | WT-HC: D10-LC | 2 | 90-3 nM | 1.66 | 1.00 | 6.01 |
| mAb1 F6 | HC-D10: WT-LC | 2 | 90-3 nM | 1.82 | 0.84 | 4.58 |
| mAb1 F7 | HC-D10: D10-LC | 4 | 90-3 nM | 1.72 | 0.94 | 5.43 |
| mAb1 F11 | D10-HC: WT-LC | 2 | 90-3 nM | 1.64 | 0.92 | 5.62 |
| mAb1 F12 | D10-HC: D10-LC | 4 | 90-3 nM | 1.71 | 0.93 | 5.41 |
| mAb1 F16 | D10-HC-D10: WT-LC | 4 | 90-3 nM | 1.59 | 1.10 | 6.88 |
| mAb1 F17 | D10-HC-D10: D10-LC | 6 | 90-3 nM | 1.91 | 0.79 | 4.15 |

[A]see Table 2

Example 11: Binding of Recombinant mAb1-D10 Fusion Variants to Hydroxyapatite

Recombinant mAb1-D10 fusion variants from Example 7 were also tested for binding ceramic hydroxyapatite (CHT) columns as described in Example 3 to assess their potential for binding to the mineral structure of bone. Recombinant mAb1-D10 fusion variants (25 μg each in 5 mM Na phosphate pH 7.4) were applied to a 100 μL column of hydroxyapatite (CHT type II, BioRad) and eluted using a gradient from 0.005 to 0.5 M $Na^+$ phosphate pH 7.4. Protein in the mobile phase eluting from the column was followed by $A_{280}$. A standard (usually a mAb1-D10 chemical conjugate) was run at the beginning and end of each set of runs to insure consistency in column performance. FIG. 13 depicts the $A_{280}$ profiles for each run. The retention time (RT) and fraction bound are shown in Table 5 below. All but one of the recombinant fusion variants were bound nearly quantitatively but showed differences in affinity as reflected in their retention times. The rank order of retention time did not correlate well with the PAR suggesting a significant effect of peptide location on binding. In particular, the strongest binding (highest RT) was observed with variant F7 (PAR4) while variant F17 (PAR6) showed slightly weaker binding. One variant (F6, PAR2) showed weaker binding than most of the PAR4 variants but significantly better than other PAR2 variants (F2 and F11). One variant (F2) with the peptide solely at the N-terminus of the light chains showed only weak binding as reflected in its RT and fraction bound (23%). The mAb1-D10 chemical conjugate ("CC"; PAR~4) yielded two peaks, with 84% eluting at an earlier RT than all of the PAR4 fusion variants.

TABLE 5

Hydroxyapatite binding by mAb1-D10 recombinant fusion variants and chemical conjugates

| Variant ID[A] | Description | PAR | RT (min) |
|---|---|---|---|
| mAb1 | Unmodified mAb | 0 | Nd* |
| F7 | HC-D10/D10-LC | 4 | 7.58 |
| F16 | D10-HC-D10/wt LC | 4 | 7.53 |
| F17 | D10-HC-D10/D10-LC | 6 | 7.44 |
| F6 | HC-D10/wt-LC | 2 | 7.07 |
| CC[B] | NA[C] | 4.8 | 6.57 (84%[†]) |
| F12 | D10-HC/D10-LC | 4 | 6.27 |
| F11 | D10-HC/wt LC | 2 | 5.39 |
| F2 | wt HC/D10-LC | 2 | 5.17 (23%) |

*none detected, [†]fraction bound (if < 100%); [A]see Table 2; [B]mAb1-D10 chemical conjugate (conjugated on hinge region cysteines and light chain C-terminus cysteines, see FIG. 3A); [C]not applicable.

Example 12: Biodistribution of Recombinant Fusion Variants in Mice

The biodistributions of a selected subset of the recombinant mAb1-D10 fusion variants (F6, F16, and F17) and the mAb1-D10 chemical conjugate produced as described in Example 6 were determined following tail vein injection into CD-1 mice. The recombinant variants were selected on the basis of several factors including expression and purification yield, TGF-β1 binding affinity, cell-based potency, and binding to hydroxyapatite. These variants included examples containing two, four, or six D10 peptides to assess whether targeting recapitulates binding to hydroxyapatite or if it is a function of peptide number. The proteins were expressed in HEK293 cells and purified over protein A. Three recombinant mAb1 fusion variants were characterized in detail in vitro and in vivo. In these, D10 peptides were recombinantly added either solely to the C-terminus of the heavy chain (mAb1 F6), both the N- and C-termini of the heavy chain (mAb1 F16), or to the N- and C-termini of the heavy chain and C-terminus of the light chains (mAb1 F17). The mAb1 F6, F16 and F17 recombinant variants have peptide to antibody ratios (PAR) of 2, 4, and 6, respectively. The mAb1-D10 peptide chemical conjugate (~4.8 PAR), which showed targeting to bone in the study in Example 6, was chosen as a positive control.

The recombinant fusion variants and chemical conjugate were labeled by reaction with Dylight® 800-4×PEG NHS ester (Thermo Scientific) in 50 mM sodium borate pH 8.65 and a dye:protein molar ratio of approximately 5:1. The degree of labeling (DOL) was maintained within 20% (~1.2 mol:mol) by adjustment of the dye:protein ratio. The labelled proteins were then administered at 1 mg/kg to CD-1 mice by tail vein injection. Anesthetized animals were subsequently imaged on an IVIS small animal near-infrared imager (Perkin Elmer) at 24, 48, 168, and 504 hours (3 weeks) following administration. Femurs and spine were recovered from an animal from each group at 240 and 504 hr to verify delivery to bone.

Figure 14:
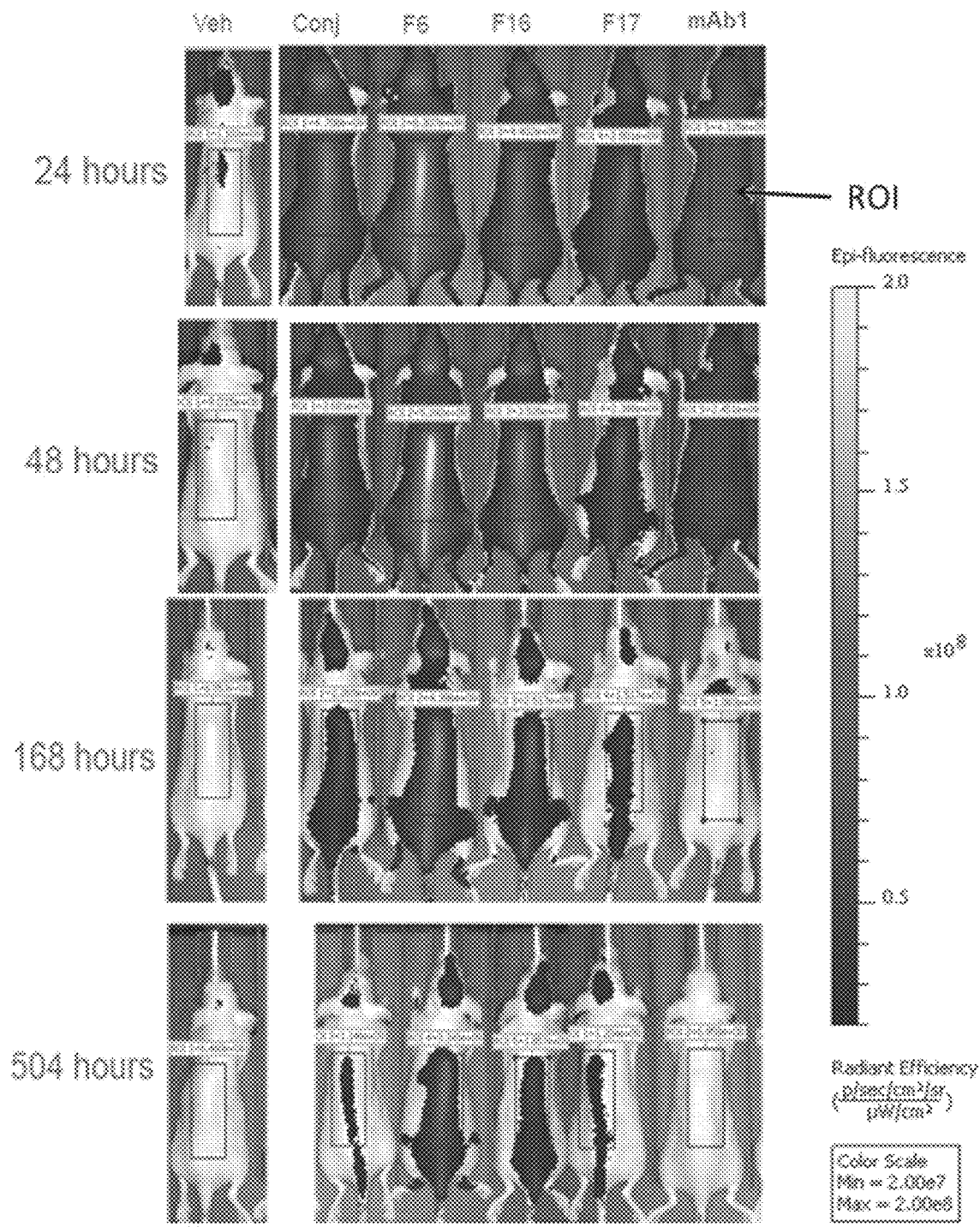
FIG. 14 depicts the biodistribution of selected fluorophore-labeled recombinant mAb1 fusion variants and mAb1 chemical conjugates in CD-1 mice obtained by live imaging at various times post-administration.
Figure 15:
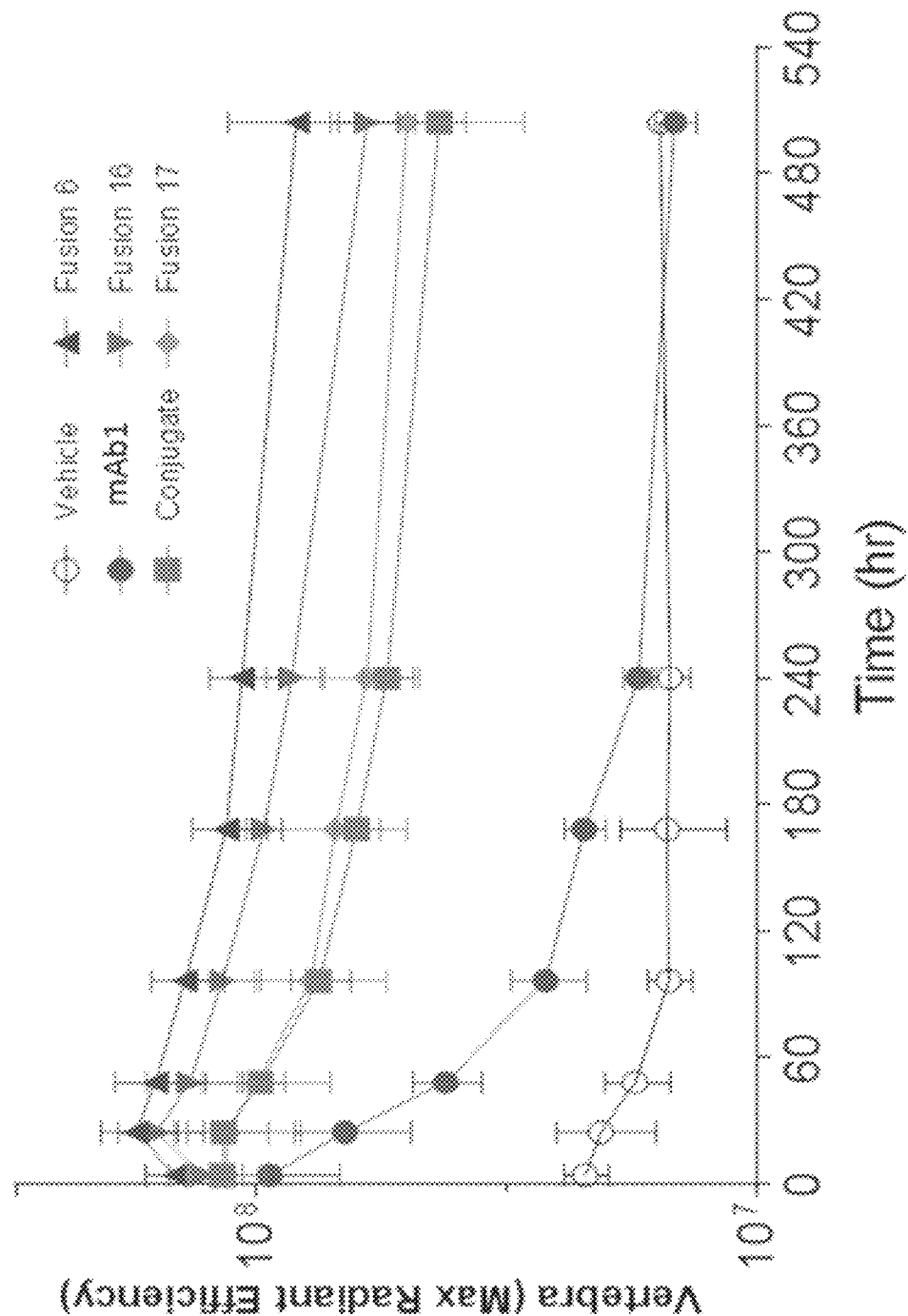
FIG. 15 depicts the amount of fluorescent dye-labeled antibody, recombinant mAb1 fusion variant and mAb1 chemical conjugate localized to the vertebral column after administration to CD-1 mice. Fluorescence was measured by an IVIS instrument over a 3-week period. The logarithm of the maximum fluorescence within the ROI is shown.

As shown in the dorsal view images in FIG. 14, all of the mAb1-D10 fusion variants and chemical conjugate were concentrated at the dorsal midline near the vertebral column and remained there for 3 weeks (504 hours) although significant differences were observed between the signal intensity for the test articles. A region of interest (ROI) was used for quantitation which included the portion of the spinal column between the shoulders and pelvis, as shown in FIG. 14. The maximum radiant efficiency within the ROI normalized for the DOL was calculated and plotted as shown in FIG. 15. Recombinant fusion variant F6, which has a D10 peptide on each of the heavy chain C-termini, showed the highest level at the spinal column of all the constructs over the entire course of the study (3 weeks). After 48 hours, the rank order of signal intensity within the ROI was variant F6>variant F16>variant F17≈chemical conjugate, and this order was maintained throughout the course of study (FIG. 15). The area under the curve (AUC) for the maximum radiant efficiencies within the ROI over time less the background autofluorescence (from vehicle-only control animals) calculated using Phoenix® WinNonlin® software (Pharsight) is shown in Table 6. There was an 8- to 22-fold increase in the bone exposure (AUC) compared to the mAb1 control and modest differences (up to 2.5-fold) between the D10-containing constructs. Variant F6 showed the highest increase compared to mAb1 (21.8-fold, p<0.05). The tissue half-life as calculated using WinNonlin® similarly showed a >10-fold increase in the half-life in bone for variant F6 compared to mAb1 (p<0.05).

Figure 16:
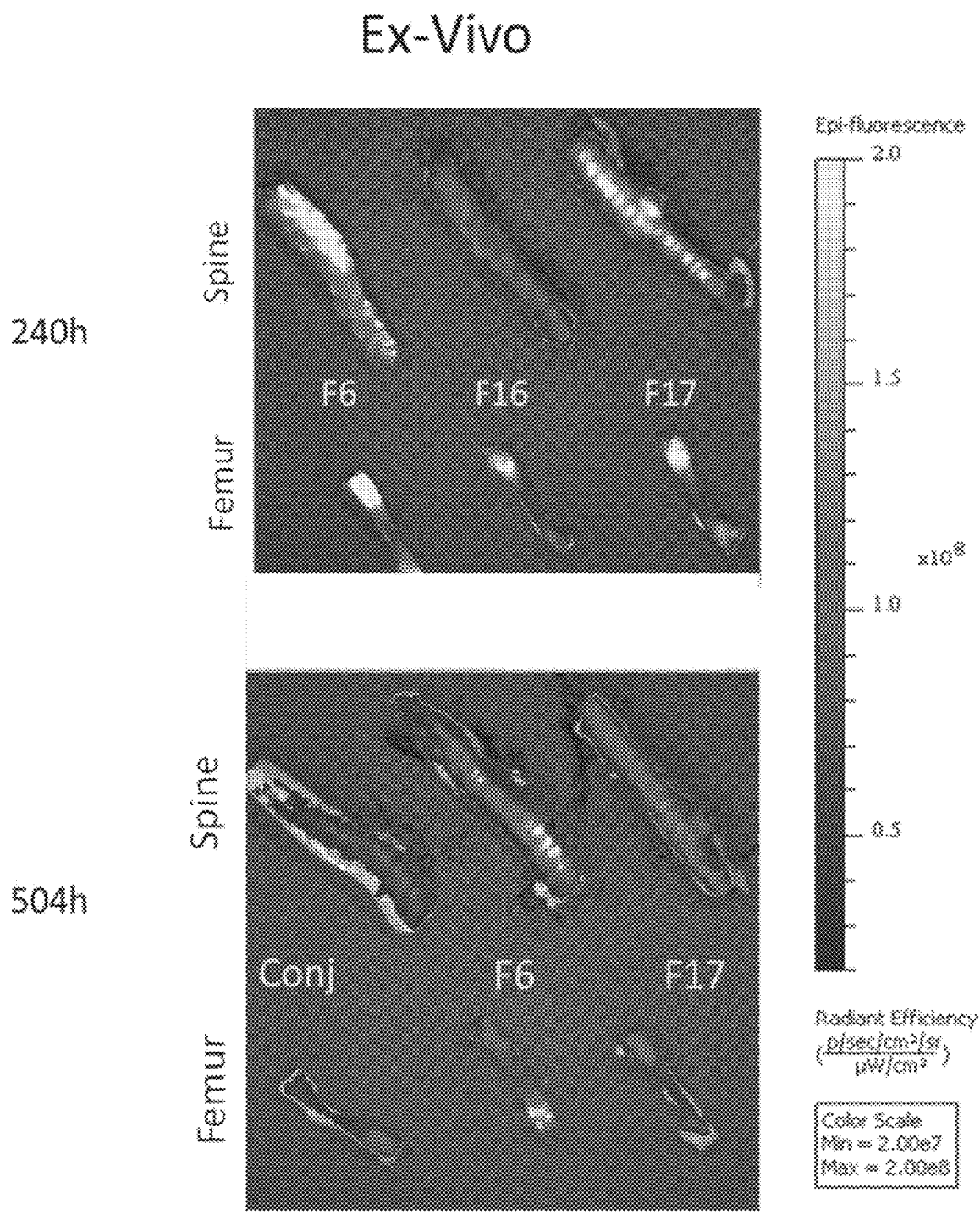
FIG. 16 depicts fluorescence images of resected spine and femurs of mice administered recombinant mAb1 fusion variants mAb1 F6, mAb1 F16, and mAb1 F17 and mAb1 chemical conjugate ("Conj") in the study described in Example 13 and FIG. 15 after 10 and 21 days.

Spines and femurs from representative animals in each cohort were isolated after 240 and 504 hr, separated from surrounding tissue and imaged (FIG. 16). The relative fluorescence intensities of these samples were consistent with the dorsal image signals observed in live animals indicating that they reflect the presence of the recombinant fusion variants and chemical conjugate on bone.

TABLE 6

Vertebral exposures from fluorescence AUC data

| Variant ID | $AUC_{inf}$(norm)[A] | Tissue $t_{1/2}$ (d)[A] |
|---|---|---|
| mAb1 | (1.0) | 2.3 ± 0.1 |
| F6 | 21.8 ± 9.1* | 25.4 ± 9.9* |
| F16 | 10.0 ± 1.6 | 14.2 ± 2.4 |
| F17 | 9.5 ± 3.1 | 19.0 ± 3.7 |
| CC[B] | 7.7 ± 1.0 | 17.9 ± 3.4 |

[A]Mean ± SEM, adjusted for DOL and normalized to mAb1;
[B]mAb1-D10 chemical conjugate
*P < 0.05 compared to mAb1

Example 13: Preparation of a Recombinant Human Anti-TGFβ-D10 Antibody Fusion Variant An expression vector for preparing mAb2 (a human anti-TGFβ IgG4 antibody with a hinge mutation S228P) bearing a C-terminal D10 sequence on the heavy chain (i.e., mAb2 HC-D10/mAb2 wt LC (SEQ ID NO: 14/SEQ ID NO: 15), which has corresponding configuration as in variant F6 (see FIG. 9B), and hereafter referred to as mAb2 F6; see Table 7) was generated in the same fashion as described in Example 7. Expi293F cells were transfected with miniprep DNA and after 6 days, conditioned medium (60 mL) was harvested, and the product protein purified over HiTrap protein A (G.E. Healthcare).

TABLE 7

Recombinant fusion variants of mAb2 with D10

| Variant ID | Heavy Chain Construct | SEQ ID NO: | Light Chain Construct | SEQ ID NO: |
|---|---|---|---|---|
| mAb2 F1 | HC | 13 | LC | 15 |
| mAb2 F2 | HC | 13 | D10-LC | 18 |
| mAb2 F3 | HC | 13 | LC-D10 | 19 |
| mAb2 F4 | HC | 13 | LC-(G4S)-D10 | 21 |
| mAb2 F5 | HC | 13 | LC-(G4S)$_2$-D10 | 22 |
| mAb2 F6 | HC-D10 | 14 | LC | 15 |
| mAb2 F7 | HC-D10 | 14 | D10-LC | 18 |
| mAb2 F8 | HC-D10 | 14 | LC-D10 | 19 |
| mAb2 F9 | HC-D10 | 14 | LC-(G4S)-D10 | 21 |
| mAb2 F10 | HC-D10 | 14 | LC-(G4S)$_2$-D10 | 22 |
| mAb2 F11 | D10-HC | 16 | LC | 15 |
| mAb2 F12 | D10-HC | 16 | D10-LC | 18 |
| mAb2 F13 | D10-HC | 16 | LC-D10 | 19 |
| mAb2 F14 | D10-HC | 16 | LC-(G4S)-D10 | 21 |
| mAb2 F15 | D10-HC | 16 | LC-(G4S)$_2$-D10 | 22 |
| mAb2 F16 | D10-HC-D10 | 17 | LC | 15 |
| mAb2 F17 | D10-HC-D10 | 17 | D10-LC | 18 |
| mAb2 F18 | D10-HC-D10 | 17 | LC-D10 | 19 |
| mAb2 F19 | D10-HC-D10 | 17 | LC-(G4S)-D10 | 21 |
| mAb2 F20 | D10-HC-D10 | 17 | LC-(G4S)$_2$-D10 | 22 |

Figure 17A:
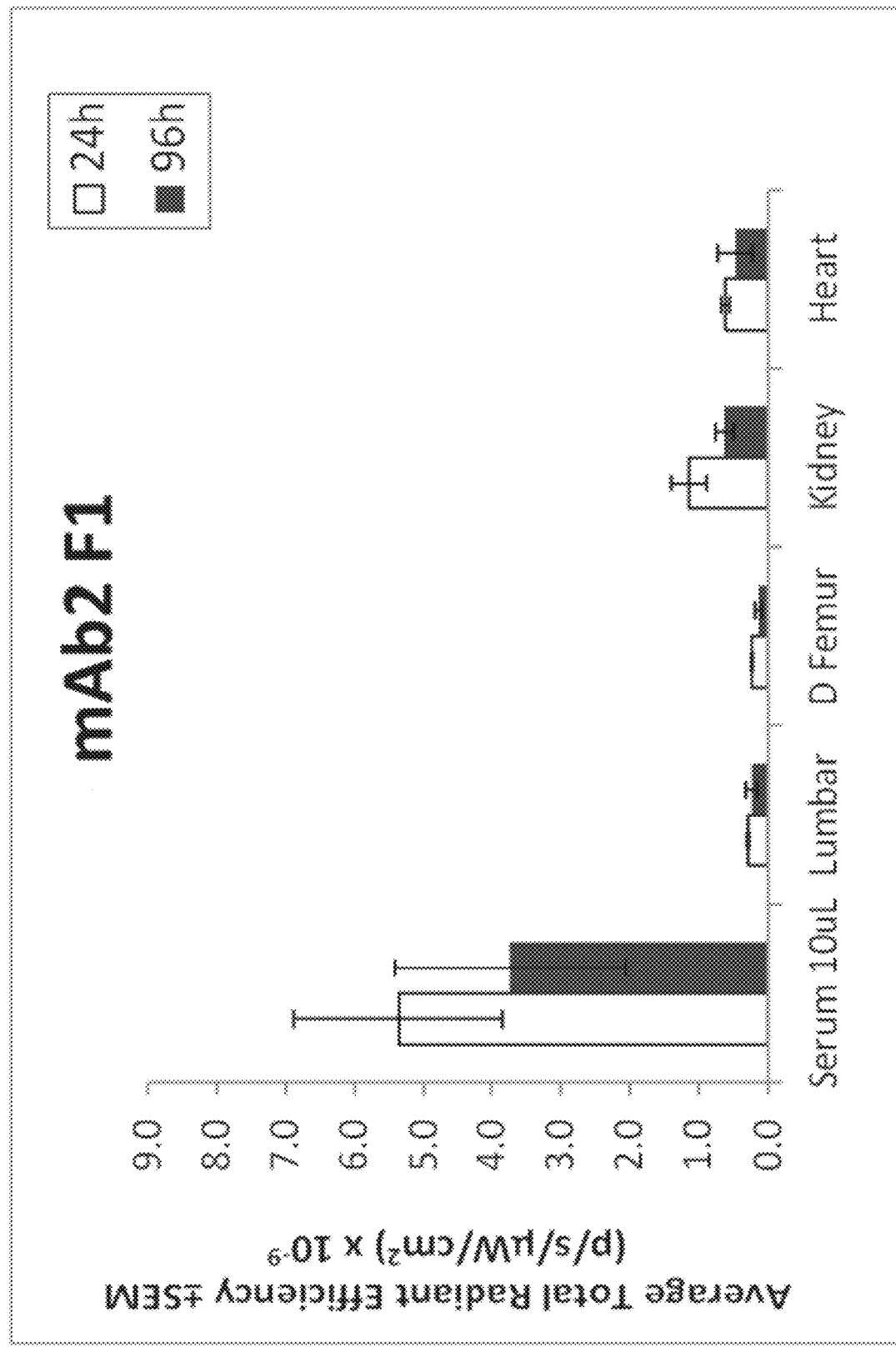
FIGS. 17A and 17B depict the fluorescence levels of mAb2 F1 and mAb2 F6 in 10 μL serum, and resected lumbar portion of spine, distal (trabecular) femur, kidney and heart after 24 and 96 hr as described in Example 15.
Figure 17B:
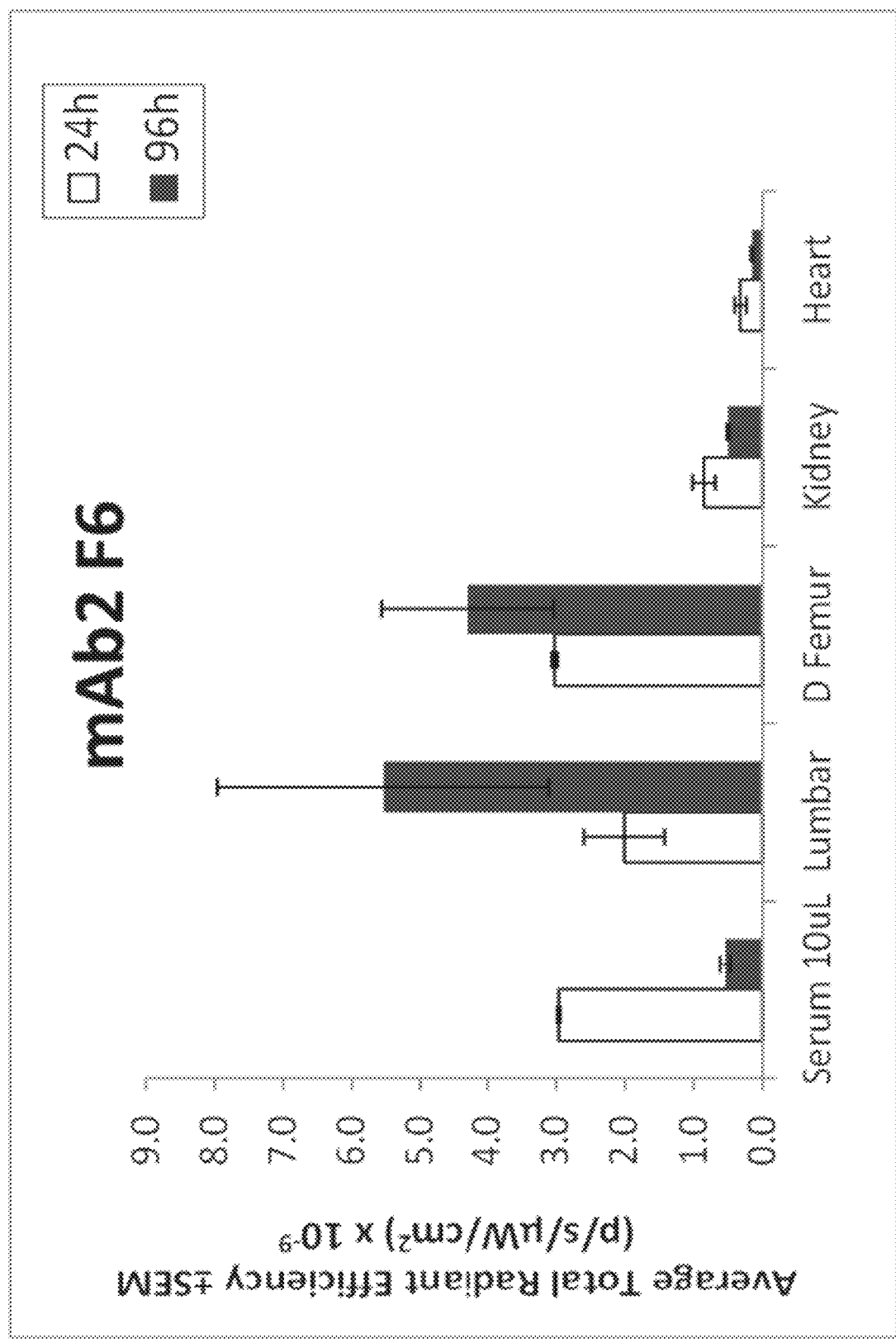

Example 14: Biodistribution of Human Anti-TGFβ-D10 Antibody Fusion Protein in Mice The recombinant mAb2 variant F6 (mAb2 F6) and mAb2 control antibodies were labeled with AlexaFluor® 647 (Thermo Scientific) and administered intraperitoneally to C57BL/6 mice at a dose of 1 mg/kg. After 24 and 96 hours, some mice were sacrificed and spines and femurs resected and imaged on an IVIS instrument. A sample of serum (10 µL) obtained at sacrifice was imaged in parallel. The average total radiant efficiency for the distal femur (trabecular) ROI and lumbar spine is shown in FIGS. 17A and 17B. The relative intensities are tabulated in Table 8. These results show a large increase in the amount of antibody in the lumbar spine and femur with significantly less in serum after 96 hours as a result of recombinant addition of D10 to mAb2.

TABLE 8

Relative bone exposure in mice for human anti-TGFβ-D10 fusion proteins in C57BL/6
Bone/serum Signal Ratio*

| | Bone | 24 h | 96 h |
|---|---|---|---|
| mAb2 F1 | Lumbar | (1.00) | 1.2 |
| | D. Femur | 0.82 | 0.70 |
| mAb2 F6 | Lumbar | 12.6 | 189 |
| | D. Femur | 19.0 | 147 |

*normalized to mAb2 lumbar at 24 h

Example 15: Single Dose Serum and Bone Pharmacokinetics of Murine Anti-TGFβ-D10 Antibody Fusion Protein in Mice In this example, the pharmacokinetics of murine anti-TGFβ-D10 antibody fusion proteins was measured in mice.

A single dose of mAb1 or recombinant mAb1 F6 (see Table 2) was administered intraperitoneally to G610C mice (an osteogenesis imperfecta animal model; n=12 per time point) and blood samples were collected at 4 hr or 2, 7, 15, 22, and 43 days post-dose. An ELISA optimized for detecting and quantifying serum concentrations of relevant antibodies was utilized.

For bone imaging, a single dose of fluorophore-labeled mAb1, recombinant mAb1 F6 or various other D10 alternatives was administered intravenously to nude CD-1 mice (n=3 per time point) and in vivo optical imaging performed at 4 hr or 1, 2, 4, 7, 10, and 21 days post-dose. Fluorescent images of mouse spinal column were generated which allowed for relative test article comparisons between mAb1 and mAb1 F6 in the bone (not shown).

Figure 18A:
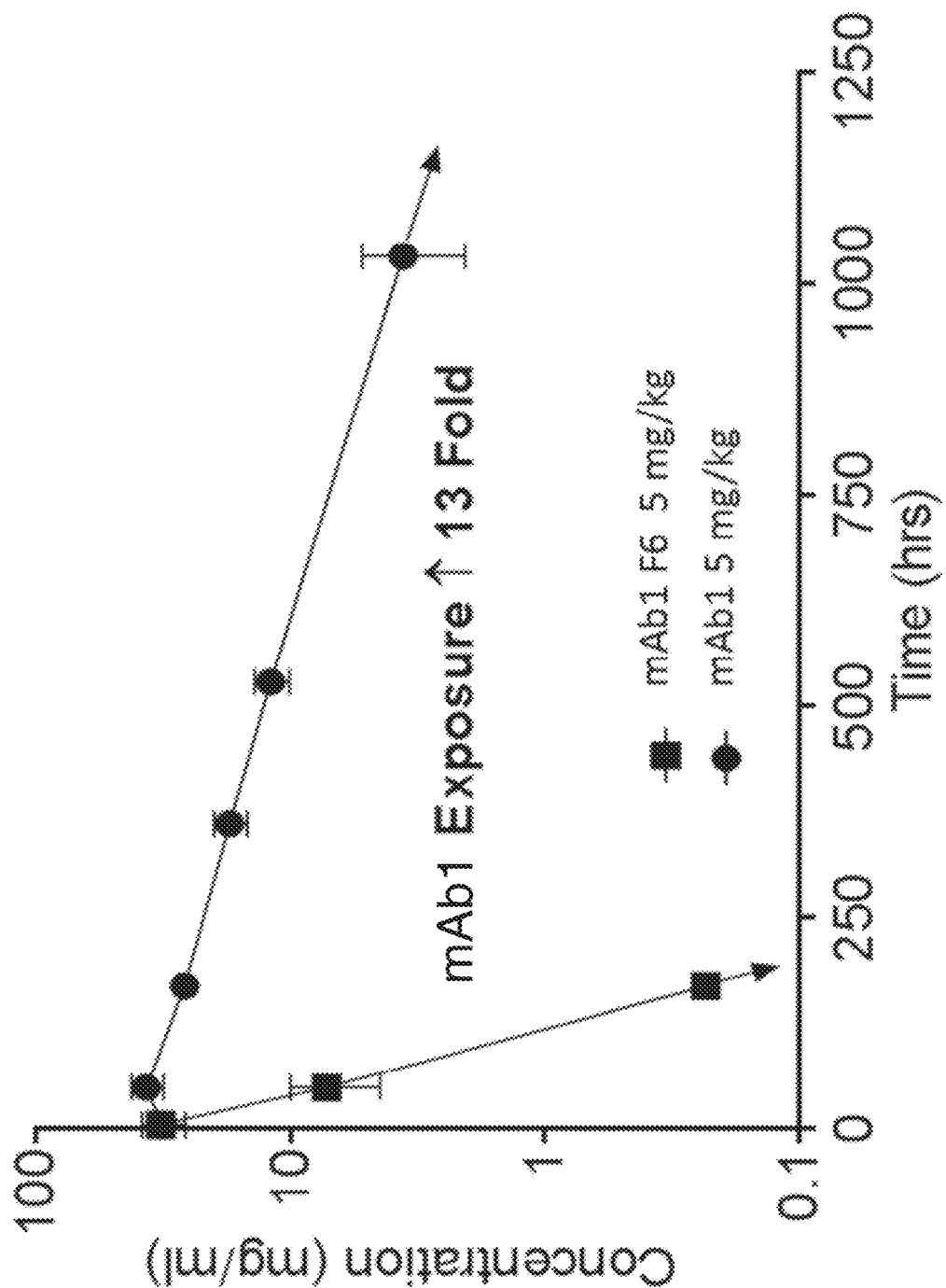
FIG. 18A shows that bone targeting via mAb1-D10 (mAb1 F6) profoundly influences serum PK following single dose administration. mAb1 F6 exhibits 13- to 14-fold lower serum exposure (AUC), faster serum clearance, and shorter serum half-life ($t_{1/2}$) than mAb1 as measured by ELISA. Data are expressed as mean±SD: Statistical significance (*p≤0.05 mAb1 F6 compared to mAb1) was observed as measured by analysis of variance (AVOVA), Dunnet's Multiple Comparison Test. mAb1 is murinized inhibitory anti-TGFβ monoclonal antibody and mAb1 F6 is a recombinant murinized inhibitory anti-TGFβ monoclonal antibody with an aspartate polypeptide D10 attached to the C-terminus of the heavy chain of mAb1. AUC for Imaging/Bone was normalized to 1.0. Doses were 5 mg/kg for each mAb1 F6 and mAb1.
Figure 18B:
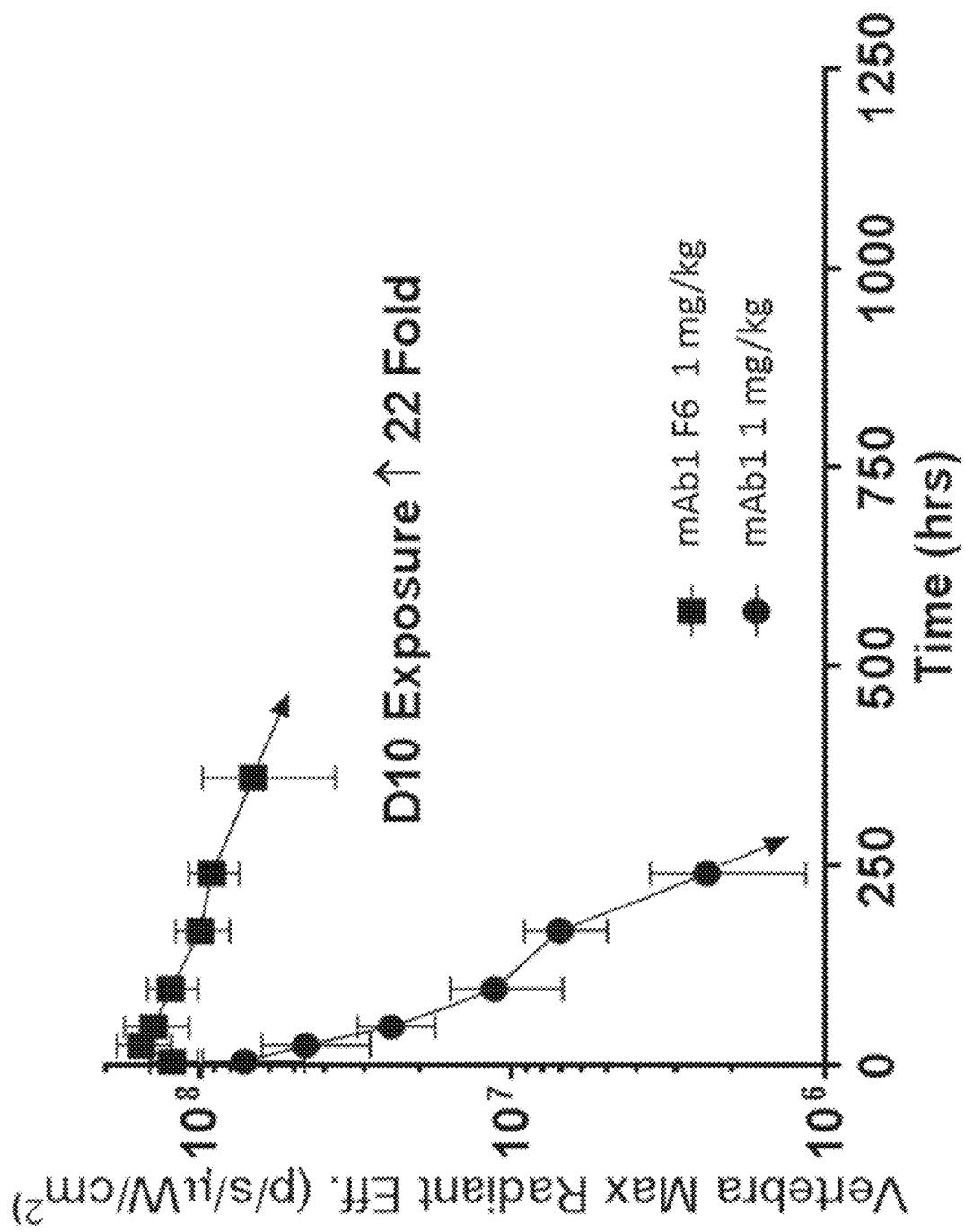
FIG. 18B shows that mAb1 F6 exhibits a 22-fold higher exposure (AUC) in the bone as measured by Optical Imaging compared to mAb1. Data expressed as mean±SD: Statistical significance (*p≤0.05 mAb1 F6 compared to mAb1) was observed as measured by AVOVA, Dunnet's Multiple Comparison Test. Doses were 1 mg/kg for each mAb1 F6 and mAb1.

Pharmacokinetic profiles in the serum and bone, respectively, can be seen in FIGS. 18A and 18B and resulting pharmacokinetic parameters in Table 9 below.

The results demonstrated fundamental contrasts in pharmacokinetics between mAb1 and mAb1 F6 in the serum and bone following a single dose. mAb1 F6 exhibited 13-fold less AUC (exposure) in the serum and 22-fold higher exposure in the bone compared to mAb1. Additionally, mAb1 F6 exhibited a 14-fold shorter $t_{1/2}$ in serum than mAb1 and commensurately 13-fold faster clearance. And lastly for bone, mAb1 F6 exhibited an 11-fold longer $t_{1/2}$ than mAb1 and commensurately 17-fold slower clearance. These attributes may be advantageous for a human form of mAb1-D10 in the clinical realm where peripheral (serum) inhibition of TGFβ may not be desired from a safety standpoint, while higher exposure in the bone may enhance efficacy.

TABLE 9

Single Dose PK Parameters

| Test Article | Method/Analyte | AUC | $t_{1/2}$(day) | Clearance |
|---|---|---|---|---|
| mAb1 | ELISA/Serum | 740 ± 91.6 | 12.6 ± 2.51 | 0.14 ± 0.034 |
| mAb1 F6 | | 56.3 ± 13.1* | 0.91 ± 0.21* | 1.78 ± 0.27* |
| mAb1 | Imaging/Bone | (1.0)# | 2.3 ± 0.1 | 1.82 ± 0.08 |
| mAb1 F6 | | 21.8 ± 9.1* | 25.4 ± 9.9* | 0.11 ± 0.03* |

*p < 0.05 compared to mAb1; #AUC normalized to 1.0 for mAb1

Figure 19:
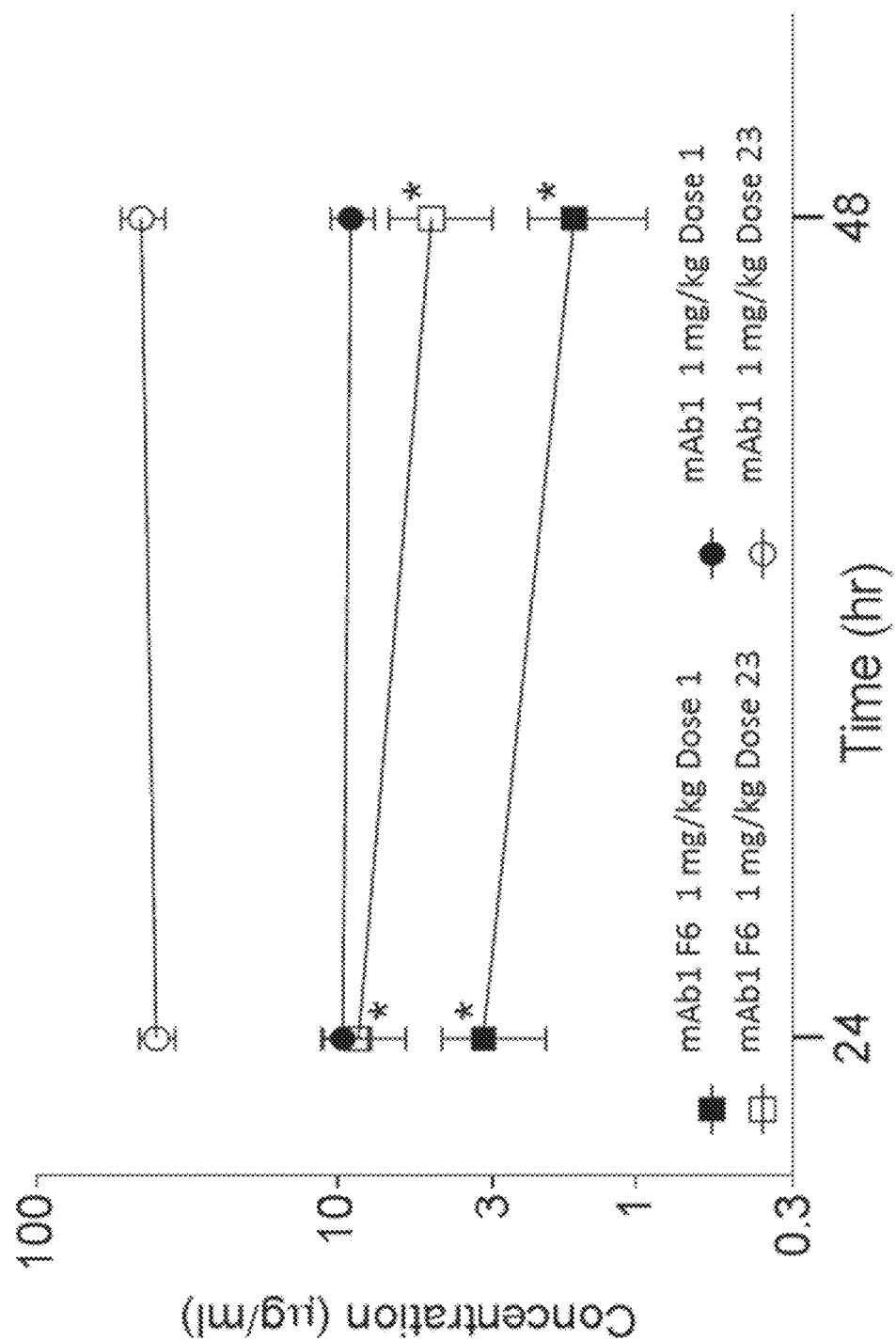
FIG. 19 illustrates multiple dose peak-trough PK profiles. Bone targeting (via mAb1 F6) profoundly influences multiple dose peak-trough serum PK. mAb1 F6 exhibits lower serum concentrations than mAb1 at both 24 and 48 hr post-dose and following the first dose and dose 23. Fold-differences were lower for mAb1 F6 by 3 to 4.5 fold at 24 hr and 6 to 9 fold at 48 hr. Accumulation also appeared less with mAb1 F6 than with mAb1. Data expressed as mean±SD: Statistical significance (*p≤0.05 mAb1 F6 compared to mAb1) was observed as measured by unpaired t-test. Serum concentrations were measured via mass spectrometry.

Example 16: Multiple Dose Peak Trough Serum Pharmacokinetics of Murine Anti-TGFβ-D10 Antibody Fusion Protein in Mice In this example, a multiple dose peak-trough pharmacokinetic study was performed in an animal model of osteogenesis imperfecta.

mAb1 and mAb1 F6 (see Table 2) were dosed intraperitoneally at a concentration of 0.3 mg/kg and 1 mg/kg, 3× weekly for 8 weeks (24 total doses) to G610C mice (n=10) and blood samples were collected at 24 and 48 hr post dose following dose 1 and 23 (beginning and end of study). Results are shown only for the 1 mg/kg dose (see FIG. 19). A Mass Spec assay, optimized for detecting and quantifying serum concentrations of relevant antibodies, was utilized.

Results are quantified in Table 10 below. The results demonstrated fundamental contrasts in pharmacokinetics between mAb1 and mAb1 F6 in the serum following both dose 1 and 23. Significantly lower serum concentrations were observed for mAb1 F6 compared to mAb1 at both 24 and 48 hr post dose on both dose 1 and 23. Additionally, the slope between 24 and 48 hr post dose for mAb1 F6 was steeper compared to mAb1 at both dose 1 and 23, suggesting that mAb1 F6 is leaving the serum (systemic circulation) at a faster rate than mAb1, likely due to its high affinity for bone (hydroxyapatite). Lastly, both mAb1 F6 and mAb1 appear to be accumulating in the serum from dose 1 to 23, but mAb1 F6 appears to accumulate at a decreased concentration compared to mAb1 (mAb1 F6: 2.5- to 3.5-fold accumulation and mAb1: 4 to 5.5 fold accumulation from dose 1 to 23). These attributes may be advantageous for a human form of mAb1 F6 in the clinical realm where peripheral (serum) inhibition of TGFβ may not be desired from a safety standpoint.

TABLE 10 mAb1 dosing study results

| Dose Groups (1 mg/kg) | Avg. Serum (μg/mL) | |
|---|---|---|
| | 24 hr | 48 hr |
| mAb1 F6 Dose 1 | 3.24 ± 1.25* | 1.60 ± 0.68* |
| mAb1 Dose 1 | 9.60 ± 1.72 | 9.03 ± 1.51 |
| mAb1 F6 Dose 23 | 8.52 ± 2.61* | 4.86 ± 1.85* |
| mAb1 Dose 23 | 40.07 ± 5.43 | 44.95 ± 7.58 |

*p ≤ 0.05 compared to mAb1

Example 17: Multiple Dose Efficacy Study in Lumbar Bone with mAb1 and mAb1 F6

In this example, a multiple dose efficacy study was performed in an animal model of osteogenesis imperfecta to determine effectiveness of bone targeted (mAb1 F6) versus untargeted mAb1 on bone density and strength.

mAb1 and mAb1 F6 were dosed intraperitoneally 3× weekly at 0.3, 1, and 5 mg/kg for 8 weeks to G610C mice. Following the final dose, mice were necropsied and the 6th lumbar bone was imaged via μCT to determine bone volume over total volume (BV/TV) and subjected to biomechanical testing to ascertain maximum force to failure (bone strength).

Figure 20:
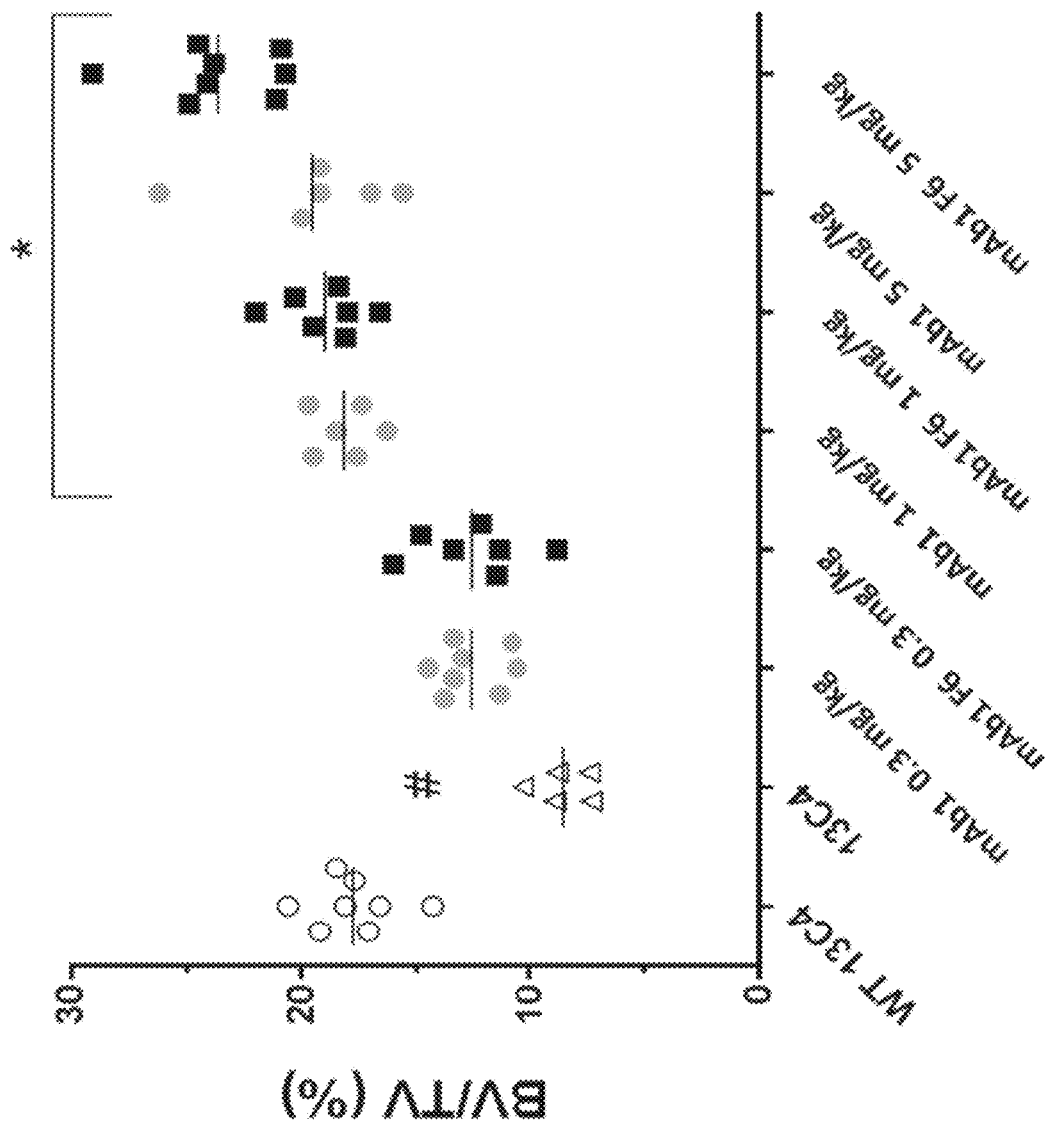
FIG. 20 shows that bone targeting (mAb1 F6) and mAb1 increase BV/TV (%) in a dose responsive fashion in G610C (01) mice. Significant changes on BV/TV (%) compared to control antibody 13C4 (mouse IgG$_1$ antibody) treated G610C mice were observed at doses of 1 and 5 mg/kg, for both treatments. G610C mice treated with 13C4 (13C4) exhibited significant decreases in BV/TV compared to WT background strain (WT 13C4). Data expressed as mean±SD: Statistical significance (*p≤0.05 mAb1 F6 compared to mAb1; #p≤0.05 13C4 compared to WT 13C4) was observed as measured by one way ANOVA. BV/TV (%) measured via μCT imaging.
Figure 21:
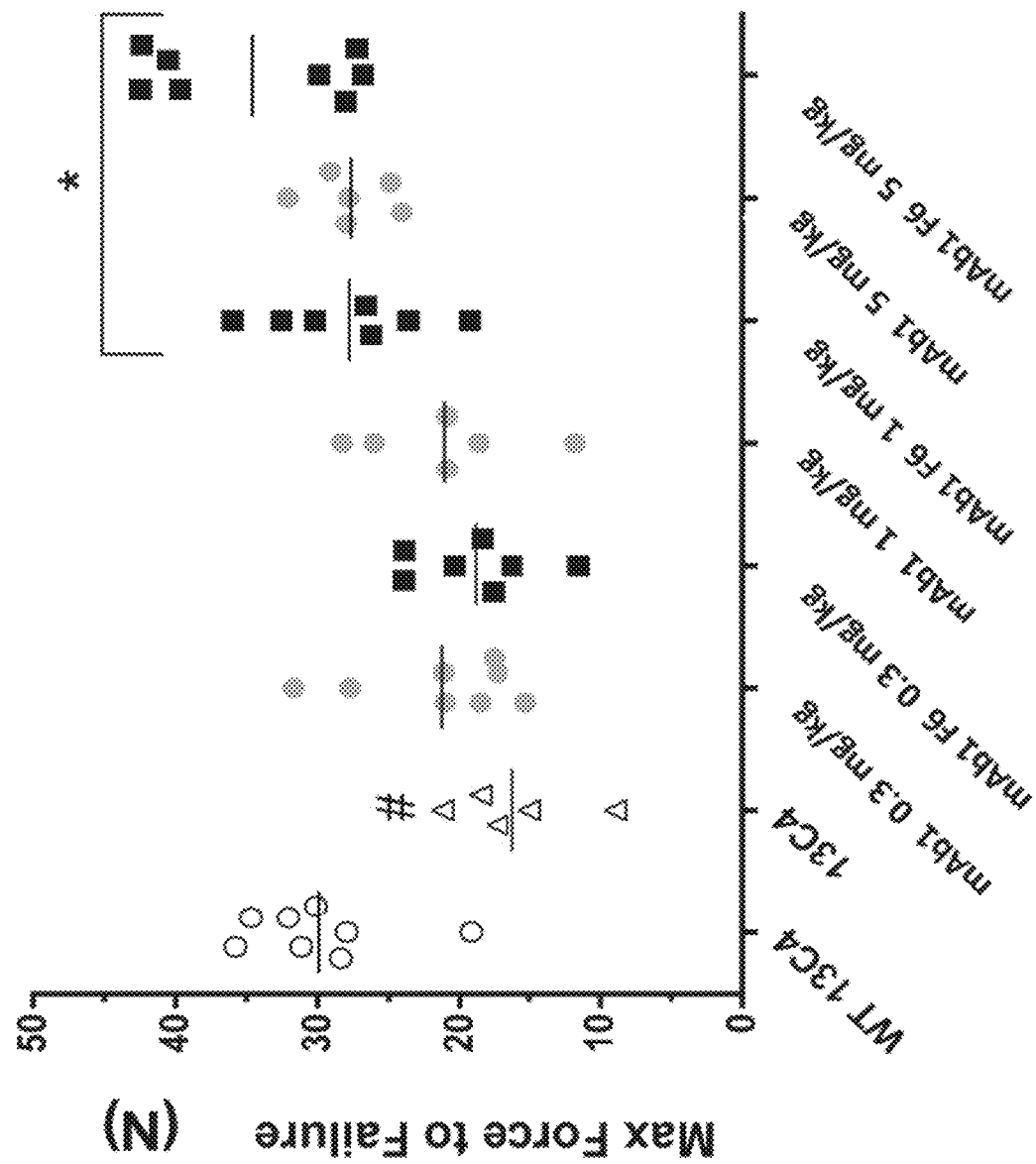
FIG. 21 shows that bone targeting (mAb1 F6) and mAb1 increase maximum force to failure in a dose responsive fashion in G610C (OI) mice. Significant changes on maximum force to failure compared to 13C4-treated G610C mice were observed at 1 and 5 mg/kg for mAb1 F6 and 5 mg/kg, only, for mAb1. G610C mice treated with an antibody control (13C4) exhibited significant decreases in maximum force to failure compared to WT background strain. Data expressed as mean±SD: Statistical significance (*p≤0.05 mAb1 F6 compared to mAb1; #p≤0.05 13C4 compared to WT 13C4) was observed as measured by one-way ANOVA. Maximum force to failure was measured via biomechanical compression test.

Results are shown in FIGS. 20 and 21. Significant changes of BV/TV (%) compared to 13C4 treated G610C mice were observed at 1 and 5 mg/kg for both treatments. Significant changes of maximum force to failure compared to 13C4 treated G610C mice were observed at 1 and 5 mg/kg for mAb1 F6 and 1 mg/kg only for mAb1. G610C mice treated with an antibody control (13C4) exhibited significant decreases in both BV/TV and maximum force to failure compared to WT background strain. These results demonstrate that both treatments induce similar dose related changes in BV/TV and maximum force to failure in the G610C mouse at this regimen of 3× weekly dosing. Trends did exist for enhanced efficacy for mAb1 F6 on bone strength, as half of the cohort of mice at 5 mg/kg exhibited substantially higher maximum force to failure values (40 Newtons or higher) than mice treated with mAb1 at 1 mg/kg or 5 mg/kg.

Example 18: Dosing Frequency Study in Lumbar Bone with mAb1 and mAb1 F6

In this example, a dosing frequency study was performed in an animal model of osteogenesis imperfecta to determine the appropriate frequency of dosing for mAb1 F6 to achieve its optimal effectiveness of bone targeted antibodies.

mAb1 and mAb1 F6 were dosed intraperitoneally at various frequencies (3× weekly, 1× weekly, 1× every 2 weeks, or 1× every 4 weeks) at 5 mg/kg for 12 weeks to G610C mice. Pharmacokinetic (PK) serum samples were taken at the beginning and end of study to ascertain Peak and Trough values for both mAb1 and mAb1 F6. Following the final dose, mice were necropsied and the 6th lumbar bone was imaged via μCT to determine bone volume over total volume (BV/TV) and subjected to biomechanical testing to ascertain maximum force to failure (bone strength).

Figure 22:
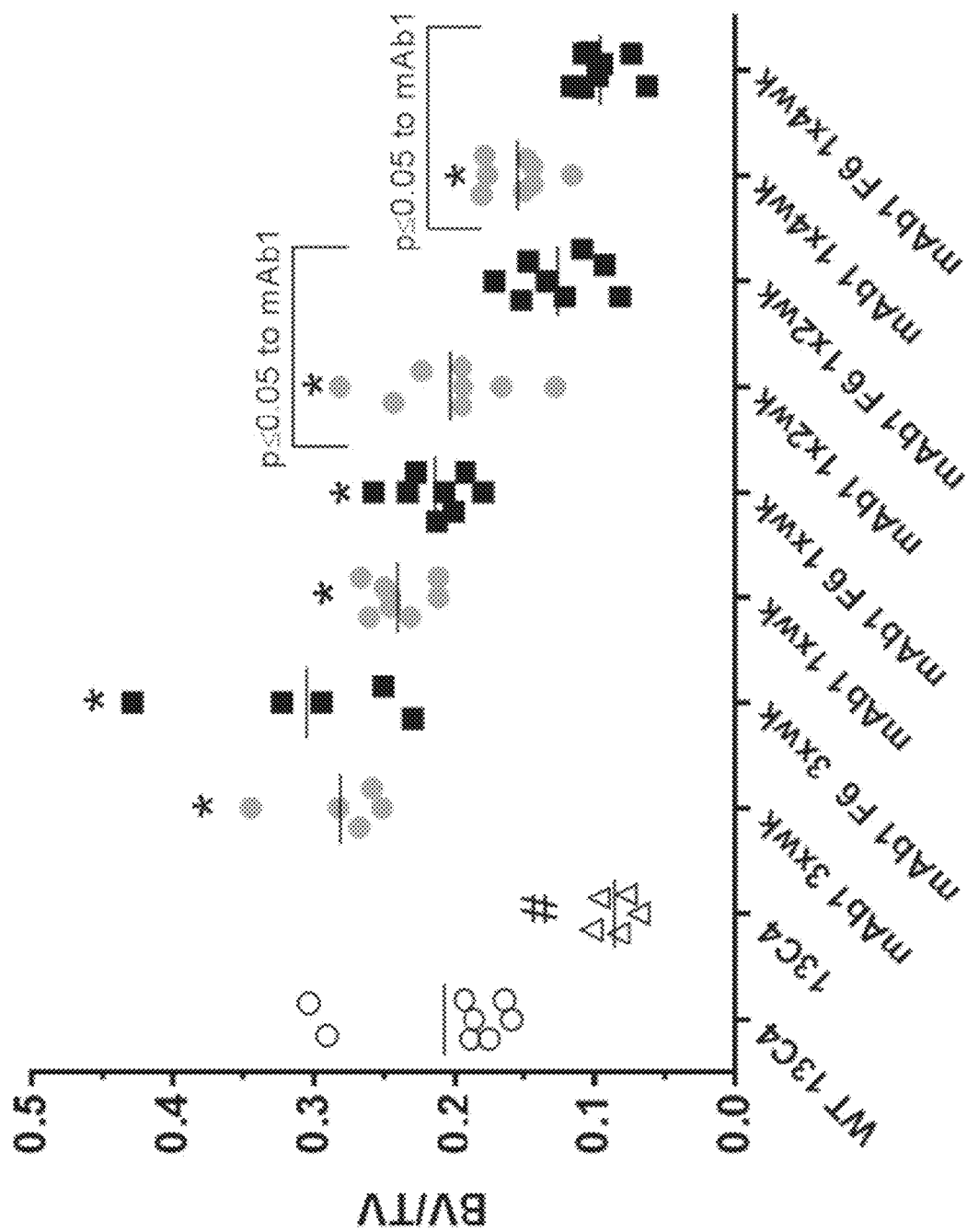
FIG. 22 shows the effects of mAb1 and mAb1 F6 on BV/TV in G610C mice. The antibodies were dosed at various frequencies (3× weekly, 1× weekly, 1× every 2 weeks, or 1× every 4 weeks) at 5 mg/kg for 12 weeks. Antibody 13C4 was used as control. Statistical significance (*p≤0.05 mAb1 F6 compared to mAb1; #p≤0.05 13C4 compared to WT 13C4) was observed as measured by one way ANOVA. BV/TV was measured via μCT imaging.
Figure 23:
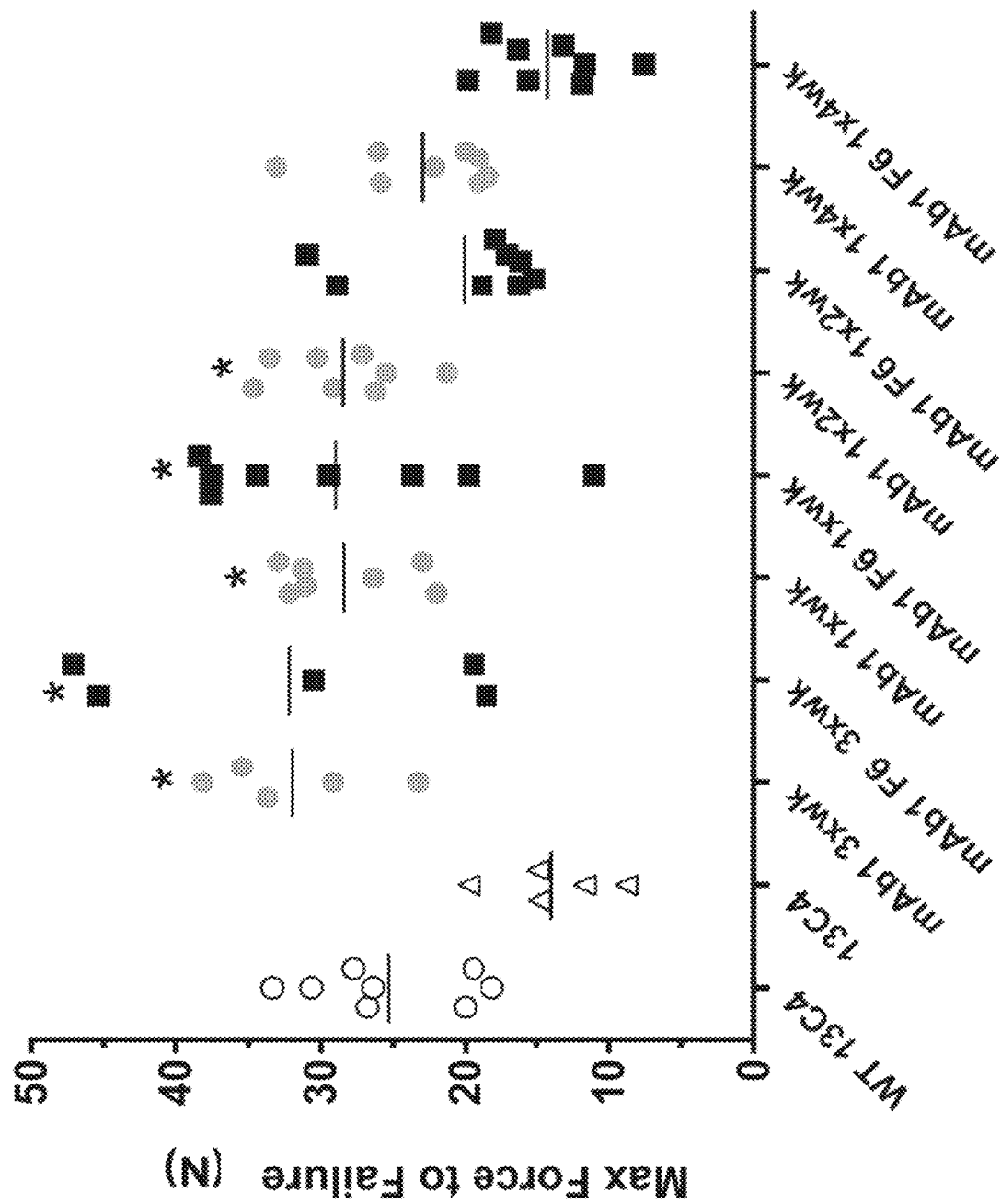
FIG. 23 shows the effects of mAb1 and mAb1 F6 on maximum force to failure in G610C mice. The antibodies were dosed at various frequencies (3× weekly, 1× weekly, 1× every 2 weeks, or 1× every 4 weeks) at 5 mg/kg for 12 weeks. Antibody 13C4 was used as control. Statistical significance (*p≤0.05 mAb1 or mAb1 F6 compared to 13C4) was observed as measured by one-way ANOVA. Maximum force to failure was measured via biomechanical compression test.
Figure 24:
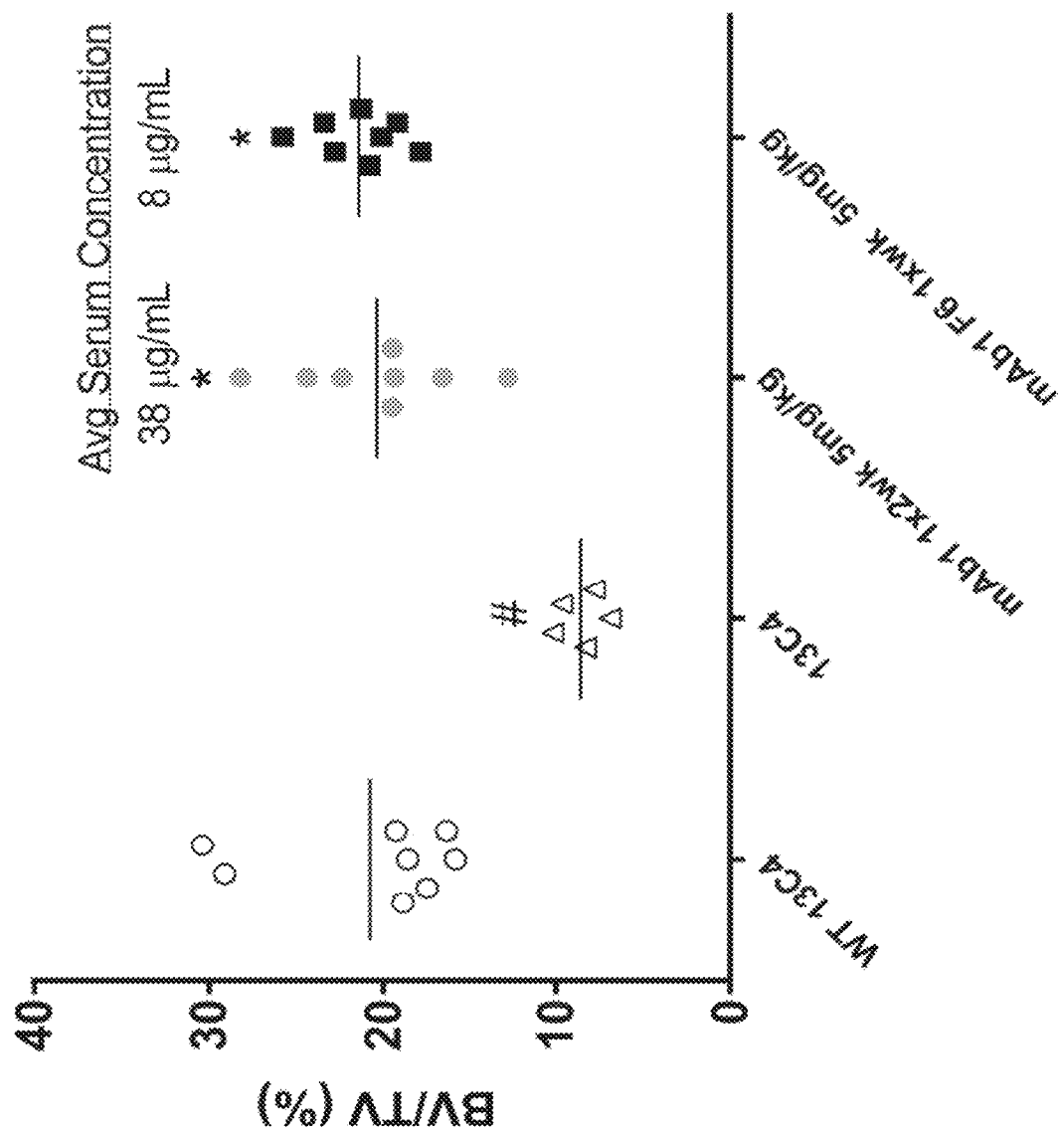
FIG. 24 shows the effects of mAb1 and mAb1 F6 on BV/TV (%) and the antibodies' average serum levels in G610C mice. The antibodies were dosed 1× every 2 weeks or 1× weekly at 5 mg/kg for 12 weeks. Antibody 13C4 was used as control. Statistical significance (*p≤0.05 mAb1 or mAb1 F6 compared to 13C4; #p≤0.05 13C4 compared to WT 13C4) was observed as measured by one-way ANOVA. BV/TV (%) was measured via μCT imaging.

Results are shown in FIGS. 22, 23, and 24. Significant changes of BV/TV (%) compared to 13C4-treated G610C mice were observed for mAb1 at 3× weekly, 1× weekly, 1× every 2 weeks, and 1× every 4 weeks. Significant changes of BV/TV (%) compared to 13C4-treated G610C mice were observed for mAb1 F6 at 3× weekly and 1× weekly. mAb1 treatment exhibited significantly higher BV/TV compared to mAb1 F6 treatment at 1× every 2 weeks and 1× every 4 weeks dosing frequency. Significant changes of maximum force to failure compared to 13C4-treated G610C mice were observed for mAb1 at 3× weekly, 1× weekly and 1× every 2 weeks. Significant changes of maximum force to failure compared to 13C4-treated G610C mice were observed for mAb1 F6 at 3× weekly and 1× weekly. G610C mice treated with a control antibody (13C4) exhibited significant decreases in BV/TV and a trend of lower maximum force to failure, compared to WT background strain.

These results demonstrate that both mAb1 and mAb1 F6 can induce similar maximum effects in BV/TV and maximum force to failure in the G610C mice. mAb1 appears to have an advantage in durability of efficacy compared to mAb1 F6, maintaining significant efficacy when dosed once every 4 weeks for BV/TV and once every 2 weeks for maximum force to failure. However, PK serum sample averages at equivalently efficacious dosing regimens (mAb1, 1× every 2 weeks and mAb1 F6, 1× weekly) resulted in approximately 38 μg/mL and 8 μg/mL for mAb1 and mAb1 F6, respectively. This suggests that serum exposure may be less with mAb 1 F6, which may offer safety advantages to OI patients.

Example 19: Dosing Frequency Study in Lumbar Bone with mAb1 F16

In this example, a dosing frequency study was performed in an animal model of osteogenesis imperfecta to determine the appropriate dosing frequency for mAb1 F16 to achieve its optimal impact on bone density.

mAb1 and mAb1 F16 were dosed intraperitoneally 3× weekly at 5 mg/kg for 8 weeks in G610C mice. Following the final dose, mice were necropsied and the 6th lumbar bone was imaged via μCT to determine bone volume over total volume (BV/TV).

Figure 25:
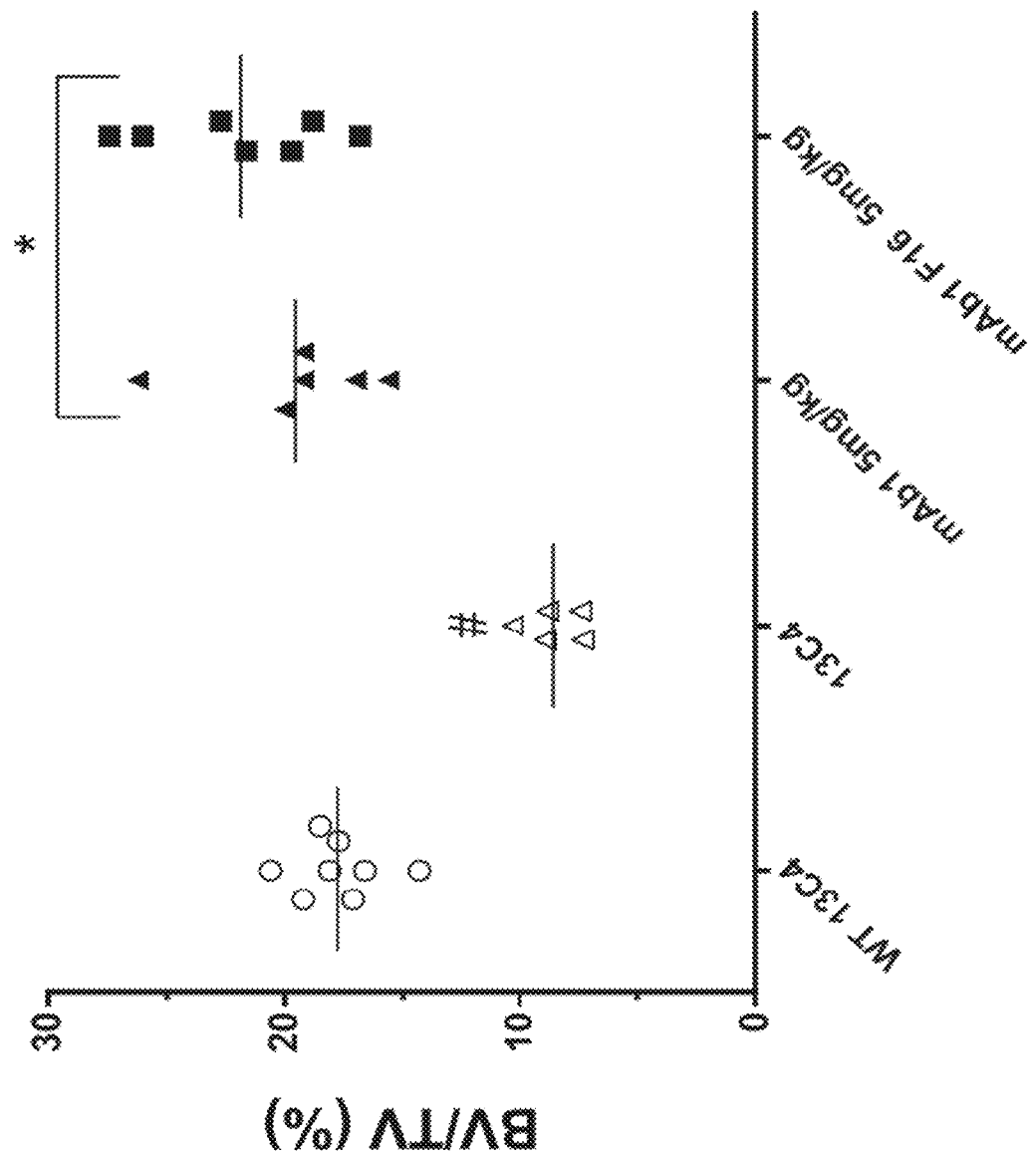
FIG. 25 shows the effects of mAb1 and mAb1 F16 on BV/TV (%) in G610C mice. The antibodies were dosed 3× weekly at 5 mg/kg for 8 weeks. Antibody 13C4 was used as control. Statistical significance (*p≤0.05 mAb1 or mAb1 F16 compared to 13C4; #p≤0.05 13C4 compared to WT 13C4) was observed as measured by one-way ANOVA. BV/TV (%) was measured via μCT imaging.

Results are shown in FIG. 25. Significant changes of BV/TV (%) compared to 13C4-treated G610C mice were observed at 5 mg/kg for both mAb1 and mAb F16. G610C mice treated with the control antibody (13C4) exhibited significant decreases in BV/TV compared to WT background strain. These results demonstrate that both mAb1 and mAb F16 induce similar dose-related changes in BV/TV in the G610C mice under this dosing regimen.

Example 20: Dosing Frequency Study in Bone with mAb1 F11

In this example, a dosing frequency study was performed in wild type mice to determine the appropriate frequency of dosing for mAb1 F11 to achieve its optimal impact on bone density.

mAb1 and mAb1 F11 were dosed intraperitoneally 3× weekly at 5 mg/kg for 11 weeks in wild type mice. Several in vivo μCT time points were taken during the in life portion of the study. Data is shown only at 9 weeks post dose for bone volume over total volume (BV/TV %).

Figure 26:
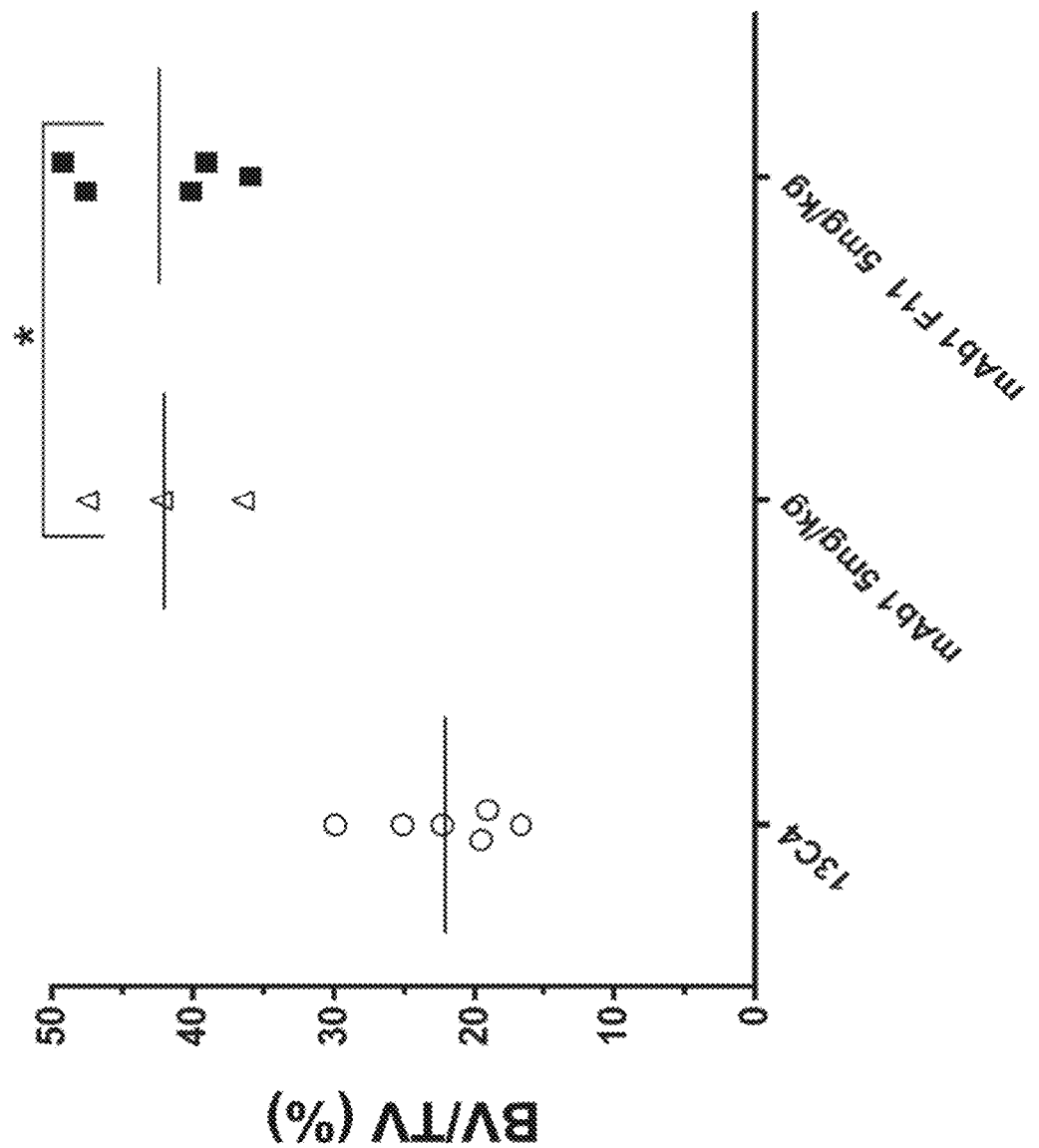
FIG. 26 shows the effects of mAb1 and mAb1 F11 on BV/TV (%) in wild type mice. The antibodies were dosed 3× weekly at 5 mg/kg for 9 weeks. Statistical significance (*p≤0.05 mAb1 or mAb1 F11 compared to 13C4) was observed as measured by one-way ANOVA. BV/TV (%) was measured via μCT imaging.
Figure 27:
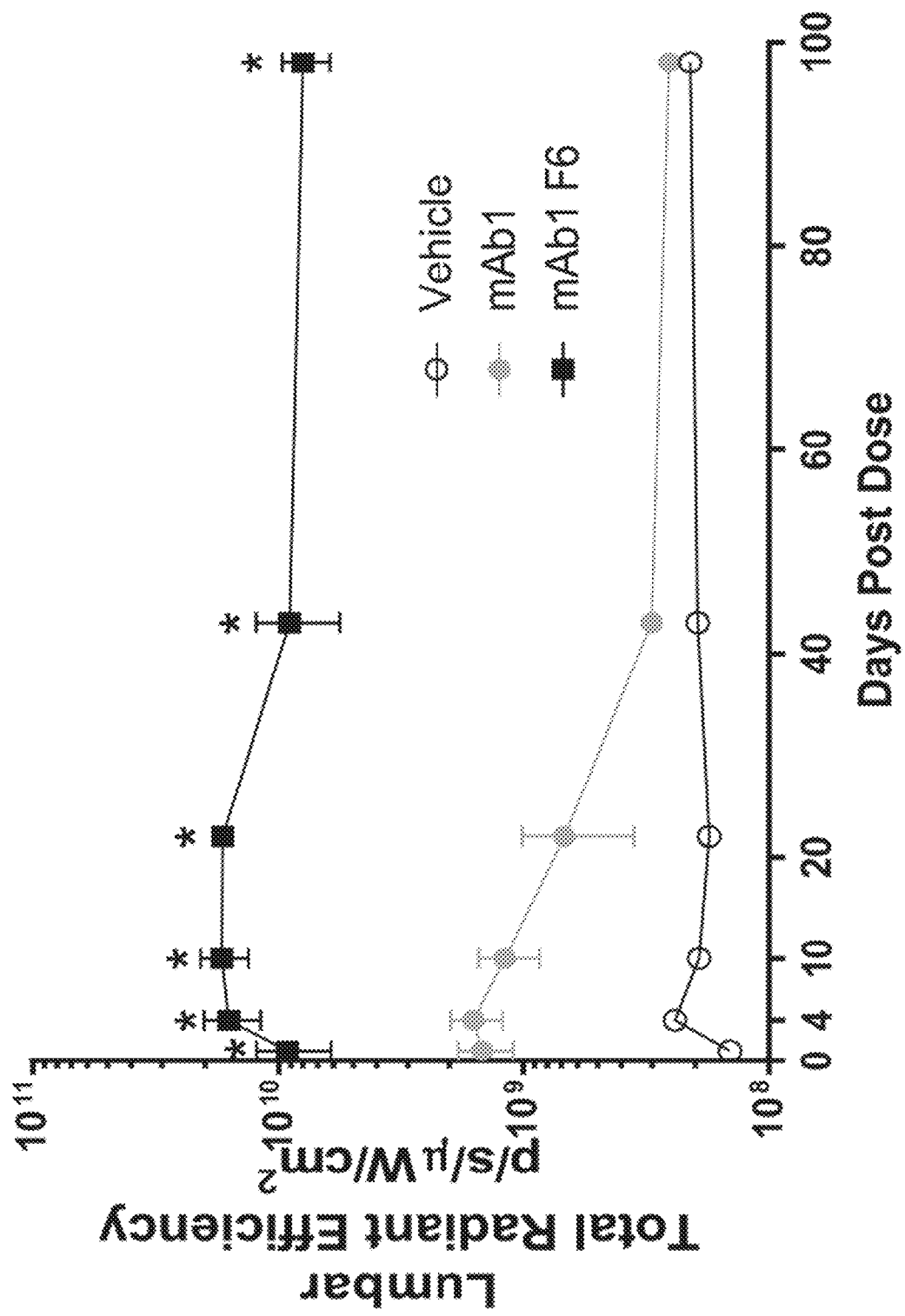
FIG. 27 shows the total radiant efficiency in the lumbar of wild type mice after receiving a single intraperitoneal dose of vehicle or fluorescently labeled mAb1 or mAb1 F6. Statistical significance (*p≤0.05 mAb1 F6 compared to mAb1) was observed as measured by one-way ANOVA.
Figure 28:
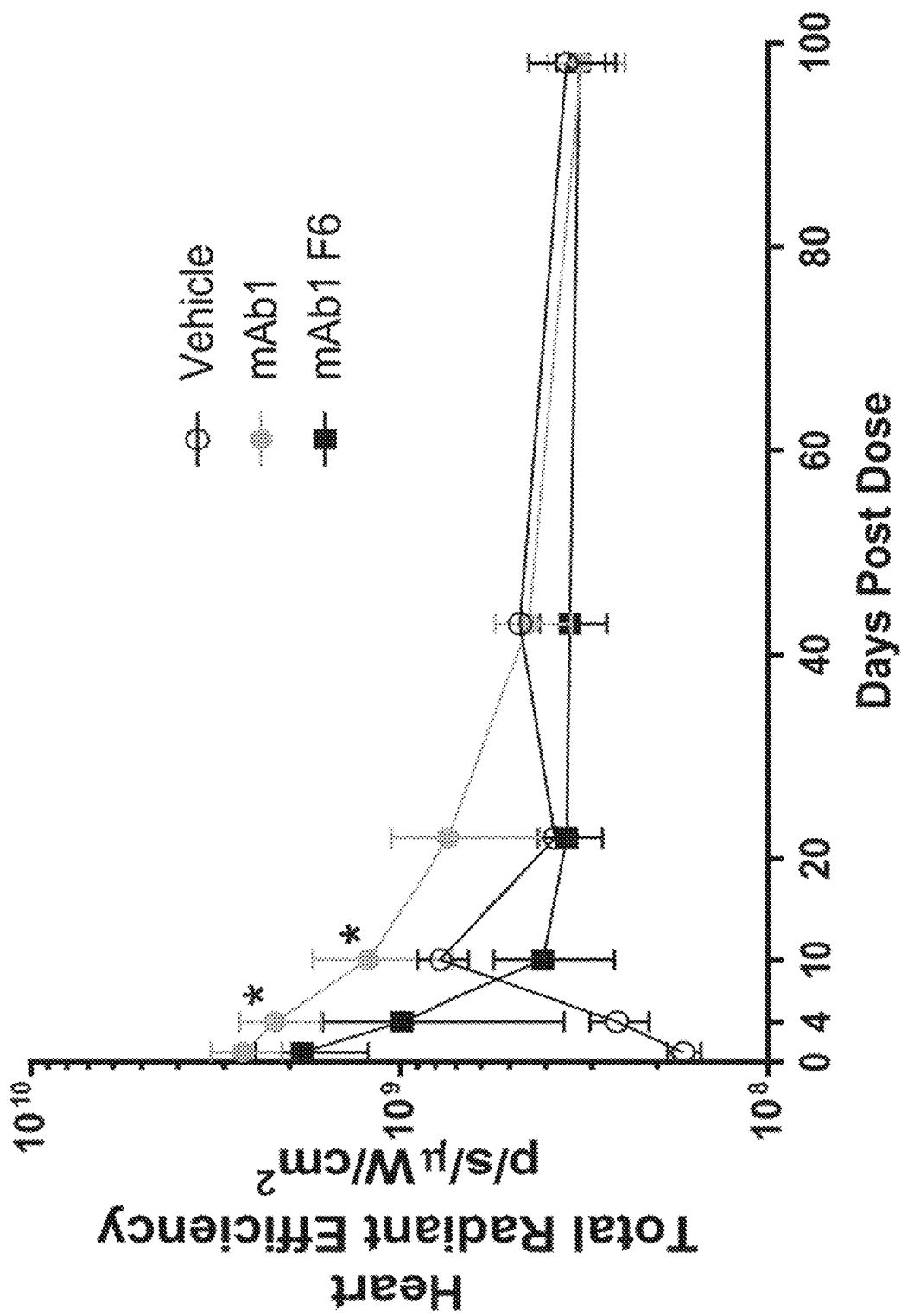
FIG. 28 shows the total radiant efficiency in the heart of wild type mice after receiving a single intraperitoneal dose of vehicle or fluorescently labeled mAb1 or mAb1 F6. Statistical significance (*p≤0.05 mAb1 compared to mAb1 F6) was observed as measured by one-way ANOVA.
Figure 29:
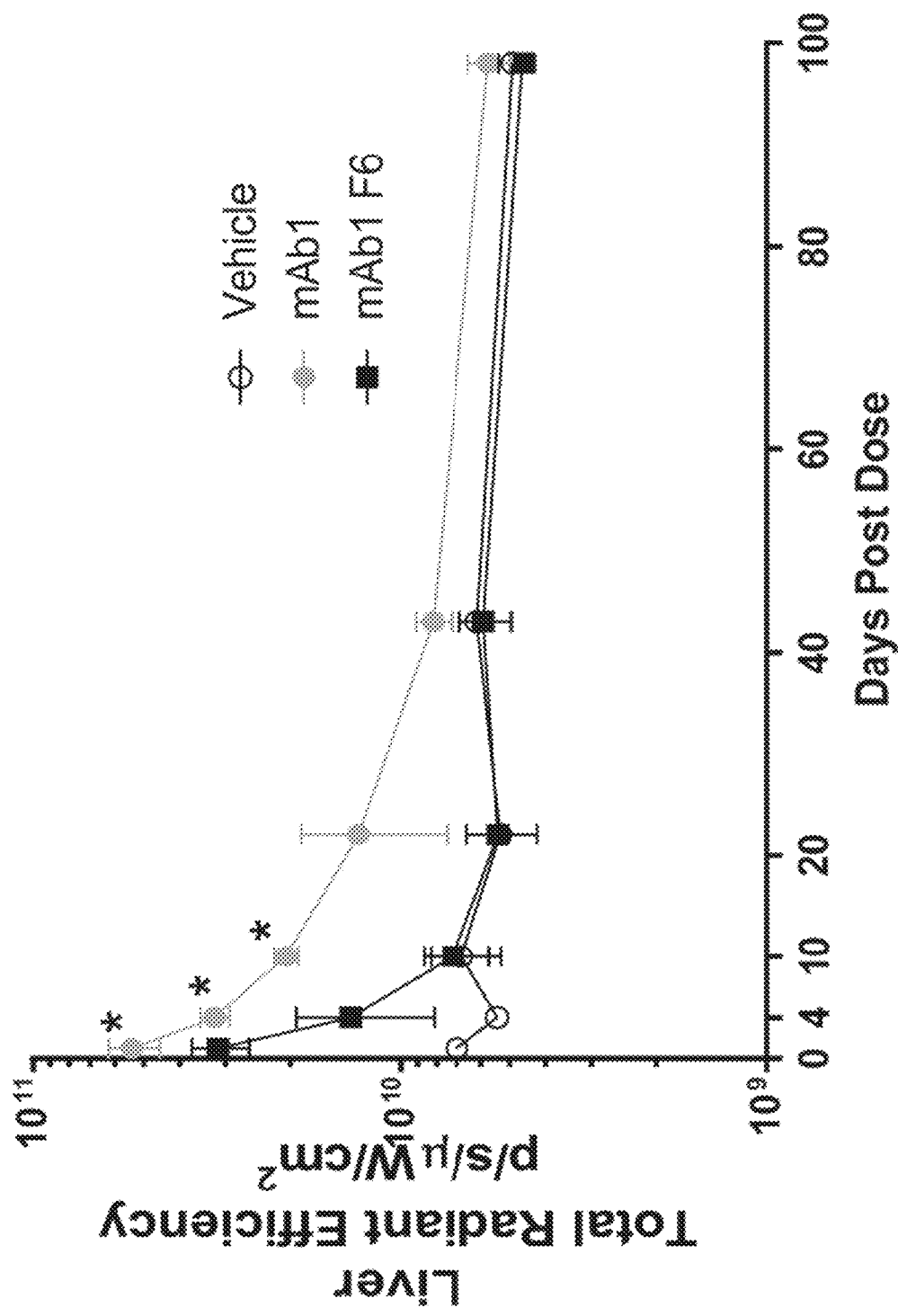
FIG. 29 shows the total radiant efficiency in the liver of wild type mice after receiving a single intraperitoneal dose of vehicle or fluorescently labeled mAb1 or mAb1 F6. Statistical significance (*p≤0.05 mAb1 compared to mAb1 F6) was observed as measured by one-way ANOVA.
Figure 30:
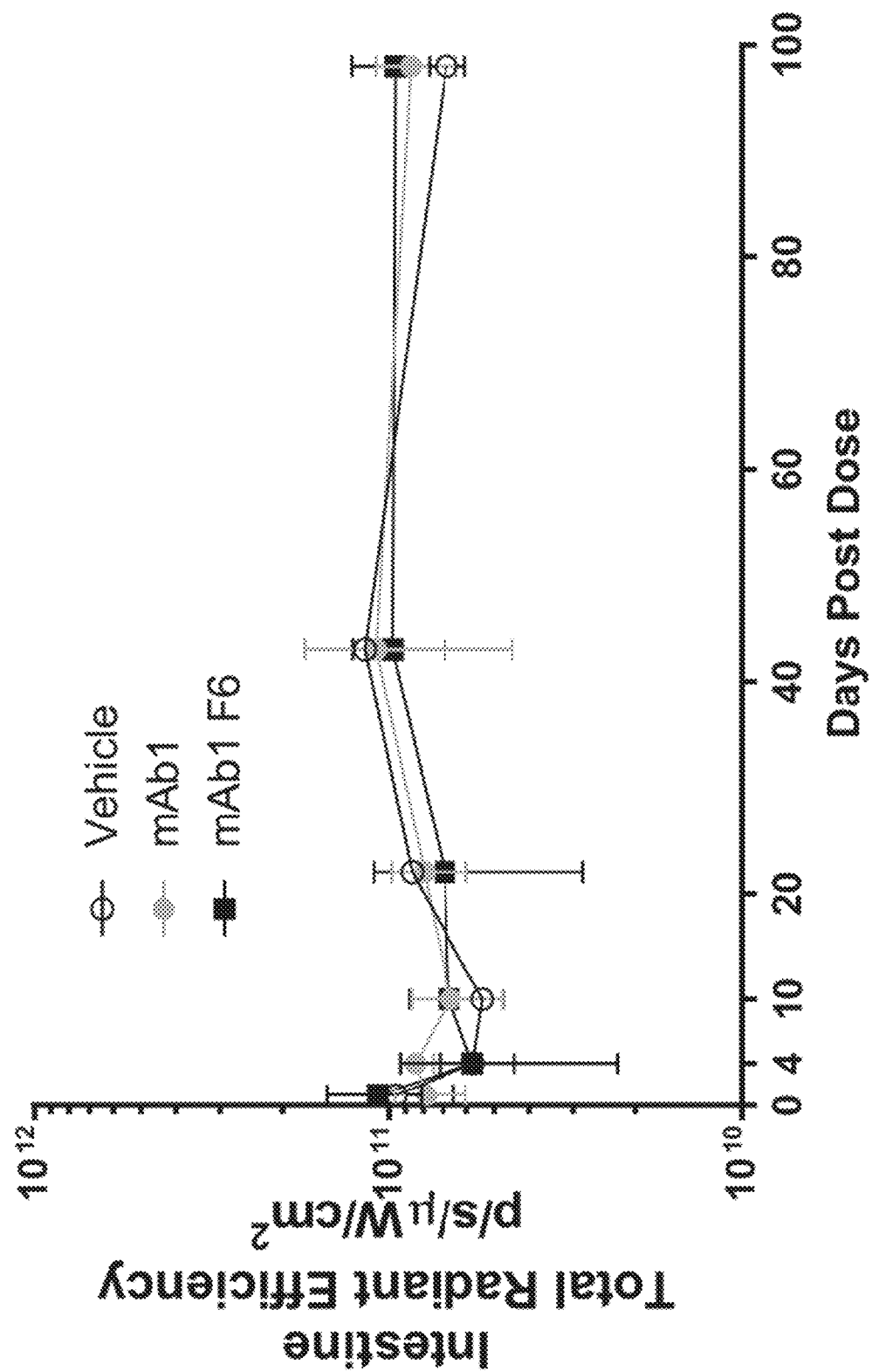
FIG. 30 shows the total radiant efficiency in the intestine of wild type mice after receiving a single intraperitoneal dose of vehicle or fluorescently labeled mAb1 or mAb1 F6.

Results are shown in FIG. 26. Significant changes of BV/TV (%) compared to 13C4-treated wild type mice were observed at 5 mg/kg for both treatments. These results demonstrate that both mAb1 and mAb1 F11 induce similar dose related changes in BV/TV in wild type mice at this dosing regimen.

Example 21: Biodistribution of Mouse and Human Bone Targeting Anti-TGFβ Antibodies mAb1 F6 and mAb2 F6 in Mice In this example, a study was conducted to compare the biodistribution of fluorescently labeled mAb1, mAb1 F6, mAb2, and mAb2 D10 (D10 conjugated to the heavy chain C-terminus of mAb2; mAb2 F6) in wild type mice. A single intraperitoneal dose of each test article and vehicle was administered to the mice, which were euthanized at various time points for tissue collection. Among other tissues harvested (data not shown), lumbar vertebrae, heart, liver, and intestines were collected at 1, 4, 10, 20, 43, and 98 days post dosing with mAb1 and mAb1 F6. Tissues were also sampled following dosing with mAb2 and mAb2 D10 at 24 and 96 hrs.

Results are shown in FIGS. 27-33. FIGS. 27-30 show total radiant efficiencies (TREs) in tissues from mice dosed with mAb1, mAb1 F6, or vehicle at 1-98 days post dose. Lumbar vertebrae exhibit robust persistent presence of mAb1 F6 compared to mAb1, with significantly higher total radiant efficiency (TRE) at every time point. In the heart and liver, mAb1 F6 exhibits much lower TRE relative to mAb1. Lastly, no significant differences were noted between vehicle and either test article in the intestines.

These results demonstrate that mAb1 F6 is characterized by high bone affinity that conversely leads to lower exposure in other tissues (e.g., heart and liver) The results also indicate the safety advantage of targeting the site of TGF-β inhibition in the bone while limiting systemic TGF-β inhibition and reducing adverse side effects. The lack of any TRE relative to vehicle in the intestines demonstrates that the fluorophore maintained its labeling on the respective antibodies. Previous data have shown if the flourophore did not maintain its label on the antibodies, it would be detected in the intestines.

Figure 31:
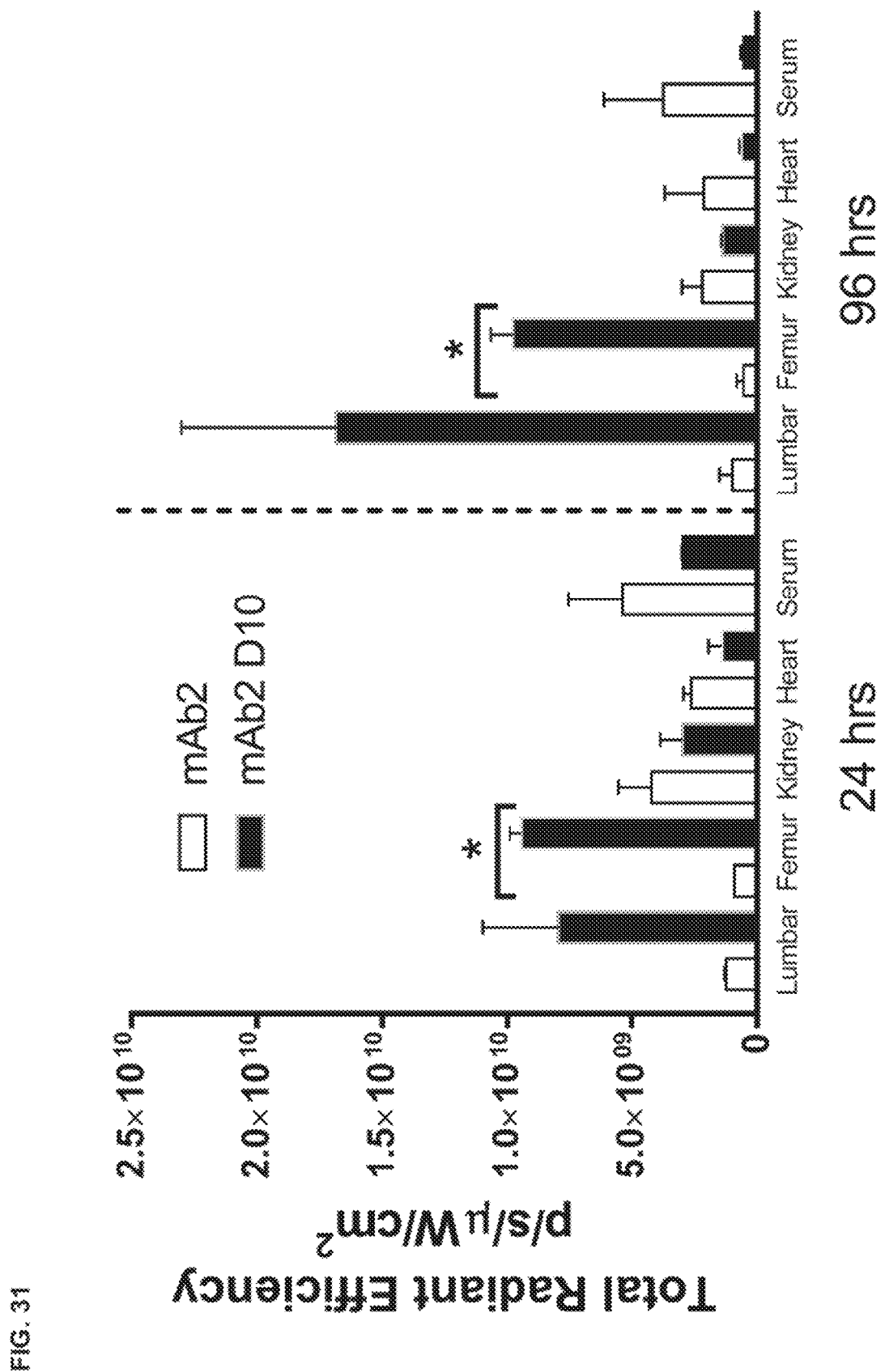
FIG. 31 shows the total radiant efficiency in the indicated tissues of wild type mice at 24 hrs or 96 hrs after receiving a single intraperitoneal dose of fluorescently labeled mAb2 or mAb2 D10. Statistical significance (*p≤0.05 mAb1 compared to mAb1 F6) was observed as measured by t test.
Figure 32:
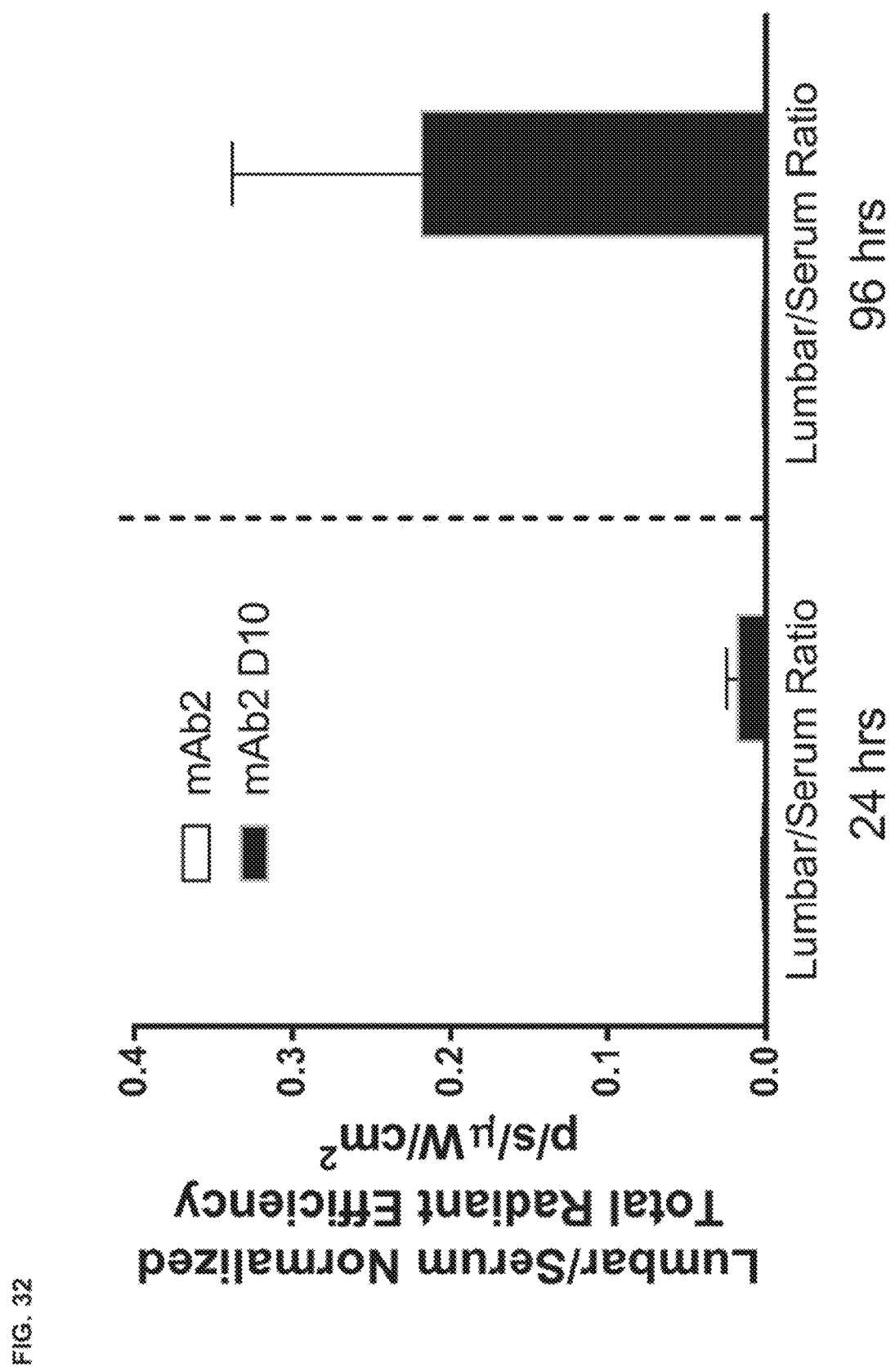
FIG. 32 shows the lumbar/serum total radiant efficiency ratios in wild type mice at 24 hrs or 96 hrs after receiving a single intraperitoneal dose of fluorescently labeled mAb2 or mAb2 D10.
Figure 33:
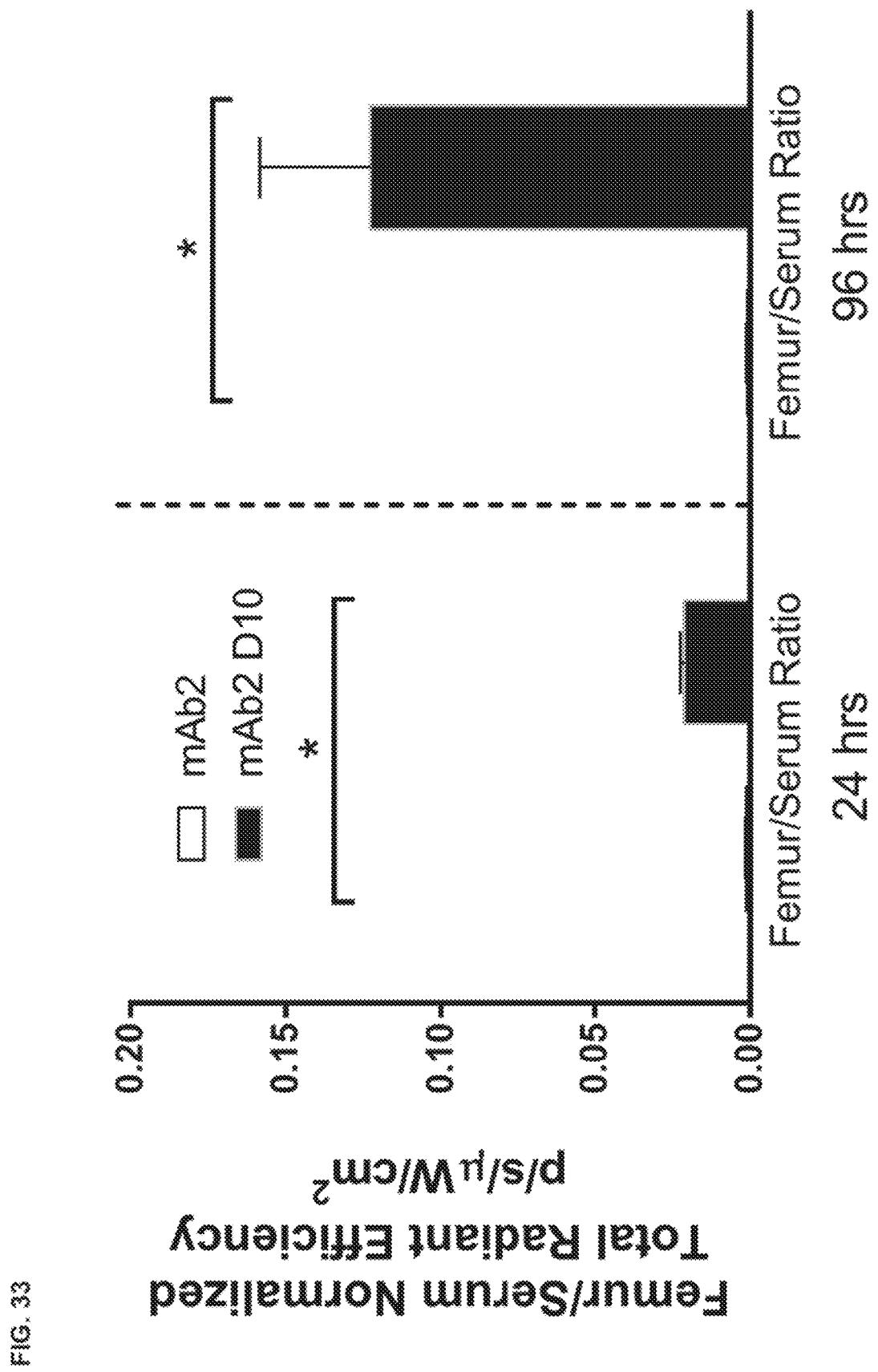
FIG. 33 shows the femur/serum total radiant efficiency ratios in wild type mice at 24 hrs or 96 hrs after receiving a single intraperitoneal dose of fluorescently labeled mAb2 or mAb2 D10. Statistical significance (*p≤0.05 mAb2 D10 compared to mAb2) was observed as measured by t test.

FIGS. 31-33 show TREs in tissues from mice dosed with either mAb2 or mAb2 D10. FIG. 31 demonstrates the high bone affinity of mAb2 D10 compared to mAb2. Significantly, higher TRE is observed in the femur for mAb2 D10 compared to mAb2. The same overall trend was observed in the lumbar. The lumbar/serum and femur/serum ratios in mAb2 D10 dosed mice as compared to those in mAb2 dosed mice also strongly support the bone targeting capability of mAb2 D10 (FIGS. 32 and 33).

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention. In some embodiments, values disclosed herein may alternatively vary in amount by ±10, 20, or 30% from values disclosed and remain within the scope of the contemplated invention.

Unless otherwise defined herein, scientific and technical terms used in connection with the present invention shall have the meanings that are commonly understood by those of ordinary skill in the art. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art. Further, unless otherwise required by context, singular terms shall include pluralities and plural terms shall include the singular. Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein. Throughout this specification and embodiments, the words "have" and "comprise," or variations such as "has," "having," "comprises," or "comprising," will be understood to imply the inclusion of a stated integer or group of integers but not the exclusion of any other integer or group of integers. Further, the singular forms "a," "an," and "the" include plural referents unless the context clearly dictates otherwise. For example, reference to "an antibody" means one or more antibodies.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

As used herein, the term "about" refers to ±10% of a given quantity, however whenever the quantity in question refers to an indivisible object, such as an amino acid or other object that would lose its identity is subdivided, then "about" refers to ±1 of the indivisible object. For example, about 2% water refers to 1.8% to 2.2% water, whereas about 6 amino acid residues refers to 5-7 amino acid residues.

As used herein, the terms "or" and "and/or" are utilized to describe multiple components in combination or exclusive of one another. For example, "x, y, and/or z" can refer to 'Y' alone, "y" alone, "z" alone, "x, y, and z," "(x and y) or z," "x or (y and z)," or "x or y or z."

Sequences referred to in the specification are provided in Table 11 below as well as in the Sequence Listing.

TABLE 11

| | Sequences |
|---|---|
| Amino acid sequence for D10 (SEQ ID NO: 1) | DDDDDDDDDD |
| Amino acid sequence for mAb1 Heavy Chain (WT HC) (SEQ ID NO: 2) | HVQLQQSGPELVRPGASVKLSCKASGYIFITYWMNWVKQR PGQGLEWIGQIFPASGSTNYNEMFEGKATLTVDTSSSTAY MQLSSLTSEDSAVYYCARGDGNYALDAMDYWGQGTSVTVS SAKTTPPSVYPLAPGSAAQTNSMVTLGCLVKGYFPEPVTV TWNSGSLSSGVHTFPAVLQSDLYTLSSSVTVPSSTWPSQT VTCNVAHPASSTKVDKKIVPRDCGCKPCICTVPEVSSVFI FPPKPKDVLTITLTPKVTCVVVDISKDDPEVQFSWFVDDV EVHTAQTKPREEQFNSTFRSVSELPIMHQDWLNGKEFKCR VNSAAFPAPIEKTISKTKGRPKAPQVYTIPPPKEQMAKDK VSLTCMITDFFPEDITVEWQWNGQPAENYKNTQPIMDTDG SYFVYSKLNVQKSNWEAGNTFTCSVLHEGLHNHHTEKSLS HSPGK |
| Amino acid sequence for mAb1 Heavy Chain with C-terminal D10 (HC-D10) (SEQ ID NO: 3) | HVQLQQSGPELVRPGASVKLSCKASGYIFITYWMNWVKQR PGQGLEWIGQIFPASGSTNYNEMFEGKATLTVDTSSSTAY MQLSSLTSEDSAVYYCARGDGNYALDAMDYWGQGTSVTVS SAKTTPPSVYPLAPGSAAQTNSMVTLGCLVKGYFPEPVTV TWNSGSLSSGVHTFPAVLQSDLYTLSSSVTVPSSTWPSQT VTCNVAHPASSTKVDKKIVPRDCGCKPCICTVPEVSSVFI FPPKPKDVLTITLTPKVTCVVVDISKDDPEVQFSWFVDDV EVHTAQTKPREEQFNSTFRSVSELPIMHQDWLNGKEFKCR VNSAAFPAPIEKTISKTKGRPKAPQVYTIPPPKEQMAKDK VSLTCMITDFFPEDITVEWQWNGQPAENYKNTQPIMDTDG SYFVYSKLNVQKSNWEAGNTFTCSVLHEGLHNHHTEKSLS HSPGKDDDDDDDDDD |
| Amino acid sequence for mAb1 Heavy Chain with N-terminal D10 (D10-HC) (SEQ ID NO: 4) | DDDDDDDDDD HVQLQQSGPELVRPGASVKLSCKASGYIFITYWMNWVKQR PGQGLEWIGQIFPASGSTNYNEMFEGKATLTVDTSSSTAY MQLSSLTSEDSAVYYCARGDGNYALDAMDYWGQGTSVTVS SAKTTPPSVYPLAPGSAAQTNSMVTLGCLVKGYFPEPVTV TWNSGSLSSGVHTFPAVLQSDLYTLSSSVTVPSSTWPSQT VTCNVAHPASSTKVDKKIVPRDCGCKPCICTVPEVSSVFI FPPKPKDVLTITLTPKVTCVVVDISKDDPEVQFSWFVDDV EVHTAQTKPREEQFNSTFRSVSELPIMHQDWLNGKEFKCR VNSAAFPAPIEKTISKTKGRPKAPQVYTIPPPKEQMAKDK VSLTCMITDFFPEDITVEWQWNGQPAENYKNTQPIMDTDG SYFVYSKLNVQKSNWEAGNTFTCSVLHEGLHNHHTEKSLS HSPGK |
| Amino acid sequence for mAb1 Heavy Chain with N- and C-termini D10 (D10-HC-D10) (SEQ ID NO: 5) | DDDDDDDDDD HVQLQQSGPELVRPGASVKLSCKASGYIFITYWMNWVKQR PGQGLEWIGQIFPASGSTNYNEMFEGKATLTVDTSSSTAY MQLSSLTSEDSAVYYCARGDGNYALDAMDYWGQGTSVTVS SAKTTPPSVYPLAPGSAAQTNSMVTLGCLVKGYFPEPVTV TWNSGSLSSGVHTFPAVLQSDLYTLSSSVTVPSSTWPSQT VTCNVAHPASSTKVDKKIVPRDCGCKPCICTVPEVSSVFI FPPKPKDVLTITLTPKVTCVVVDISKDDPEVQFSWFVDDV EVHTAQTKPREEQFNSTFRSVSELPIMHQDWLNGKEFKCR VNSAAFPAPIEKTISKTKGRPKAPQVYTIPPPKEQMAKDK VSLTCMITDFFPEDITVEWQWNGQPAENYKNTQPIMDTDG SYFVYSKLNVQKSNWEAGNTFTCSVLHEGLHNHHTEKSLS HSPGKDDDDDDDDDD |
| Amino acid sequence for mAb1 Light Chain (WT LC) (SEQ ID NO: 6) | NIVLTQSPASLAVSLGQRATISCRASESVDSYGNSFMHWY QQKSGQPPKLLIYLASNLESGVPARFSGSGSRTDFTLTID PVEADDAATYYCQQNNEDPLTFGAGTKLELKRADAAPTVS IFPPSSEQLTSGGASVVCFLNNFYPKDINVKWKIDGSERQ NGVLNSWTDQDSKDSTYSMSSTLTLTKDEYERHNSYTCEA THKTSTSPIVKSFNRNEC |
| Amino acid sequence for mAb1 Light Chain with N-terminal D10 (D10-LC) (SEQ ID NO: 7) | DDDDDDDDDD NIVLTQSPASLAVSLGQRATISCRASESVDSYGNSFMHWY QQKSGQPPKLLIYLASNLESGVPARFSGSGSRTDFTLTID PVEADDAATYYCQQNNEDPLTFGAGTKLELKRADAAPTVS IFPPSSEQLTSGGASVVCFLNNFYPKDINVKWKIDGSERQ NGVLNSWTDQDSKDSTYSMSSTLTLTKDEYERHNSYTCEA THKTSTSPIVKSFNRNEC |
| Amino acid sequence for mAb1 Light Chain with C-terminal D10 (LC-D10) (SEQ ID NO: 8) | NIVLTQSPASLAVSLGQRATISCRASESVDSYGNSFMHWY QQKSGQPPKLLIYLASNLESGVPARFSGSGSRTDFTLTID PVEADDAATYYCQQNNEDPLTFGAGTKLELKRADAAPTVS IFPPSSEQLTSGGASVVCFLNNFYPKDINVKWKIDGSERQ NGVLNSWTDQDSKDSTYSMSSTLTLTKDEYERHNSYTCEA THKTSTSPIVKSFNRNECDDDDDDDDDD |

TABLE 11-continued

| Sequences | |
|---|---|
| Amino acid sequence for D10 (SEQ ID NO: 1) | DDDDDDDDDD |
| Amino acid sequence for: 1x peptide linker (G4S) (SEQ ID NO: 9) | GGGGS |
| Amino acid sequence for: 2x peptide linker ((G4S) x 2) (SEQ ID NO: 10) | GGGGSGGGGS |
| Amino acid sequence for mAb1 Light Chain with 1x Linker and C-terminal D10 (LC-G4S-D10) (SEQ ID NO: 11) | NIVLTQSPASLAVSLGQRATISCRASESVDSYGNSFMHWY QQKSGQPPKLLIYLASNLESGVPARFSGSGSRTDFTLTID PVEADDAATYYCQQNNEDPLTFGAGTKLELKRADAAPTVS IFPPSSEQLTSGGASVVCFLNNFYPKDINVKWKIDGSERQ NGVLNSWTDQDSKDSTYSMSSTLTLTKDEYERHNSYTCEA THKTSTSPIVKSFNRNECGGGGSDDDDDDDDDD |
| Amino acid sequence for mAb1 Light Chain with 2x Linker and C-terminal D10 (LC-(G4S)2-D10) (SEQ ID NO: 12) | NIVLTQSPASLAVSLGQRATISCRASESVDSYGNSFMHWY QQKSGQPPKLLIYLASNLESGVPARFSGSGSRTDFTLTID PVEADDAATYYCQQNNEDPLTFGAGTKLELKRADAAPTVS IFPPSSEQLTSGGASVVCFLNNFYPKDINVKWKIDGSERQ NGVLNSWTDQDSKDSTYSMSSTLTLTKDEYERHNSYTCEA THKTSTSPIVKSFNRNECGGGGSGGGGSDDDDDDDDDD |
| Amino acid sequence for mAb2 Heavy Chain WT (WT HC) (SEQ ID NO: 13) | QVQLVQSGAEVKKPGSSVKVSCKASGYTFSSNVISWVRQA PGQGLEWMGGVIPIVDIANYAQRFKGRVTITADESTSTTY MELSSLRSEDTAVYYCASTLGLVLDAMDYWGQGTLVTVSS ASTKGPSVFPLAPCSRSTSESTAALGCLVKDYFPEPVTVS WNSGALTSGVHTFPAVLQSSGLYSLSSVVTVPSSSLGTKT YTCNVDHKPSNTKVDKRVESKYGPPCPPCPAPEFLGGPSV FLFPPKPKDTLMISRTPEVTCVVVDVSQEDPEVQFNWYVD GVEVHNAKTKPREEQFNSTYRVVSVLTVLHQDWLNGKEYK CKVSNKGLPSSIEKTISKAKGQPREPQVYTLPPSQEEMTK NQVSLTCLVKGFYPSDIAVEWESNGQPENNYKTTPPVLDS DGSFFLYSRLTVDKSRWQEGNVFSCSVMHEALHNHYTQKS LSLSLGK |
| Amino acid sequence for mAb2 Heavy Chain with C-terminal D10 (HC-D10) (SEQ ID NO: 14) | QVQLVQSGAEVKKPGSSVKVSCKASGYTFSSNVISWVRQA PGQGLEWMGGVIPIVDIANYAQRFKGRVTITADESTSTTY MELSSLRSEDTAVYYCASTLGLVLDAMDYWGQGTLVTVSS ASTKGPSVFPLAPCSRSTSESTAALGCLVKDYFPEPVTVS WNSGALTSGVHTFPAVLQSSGLYSLSSVVTVPSSSLGTKT YTCNVDHKPSNTKVDKRVESKYGPPCPPCPAPEFLGGPSV FLFPPKPKDTLMISRTPEVTCVVVDVSQEDPEVQFNWYVD GVEVHNAKTKPREEQFNSTYRVVSVLTVLHQDWLNGKEYK CKVSNKGLPSSIEKTISKAKGQPREPQVYTLPPSQEEMTK NQVSLTCLVKGFYPSDIAVEWESNGQPENNYKTTPPVLDS DGSFFLYSRLTVDKSRWQEGNVFSCSVMHEALHNHYTQKS LSLSLGKDDDDDDDDDD |
| Amino acid sequence for mAb2 Light Chain WT (WT LC) (SEQ ID NO: 15) | ETVLTQSPGTLSLSPGERATLSCRASQSLGSSYLAWYQQK PGQAPRLLIYGASSRAPGIPDRFSGSGSGTDFTLTISRLE PEDFAVYYCQQYADSPITFGQGTRLEIKRTVAAPSVFIFP PSDEQLKSGTASVVCLLNNFYPREAKVQWKVDNALQSGNS QESVTEQDSKDSTYSLSSTLTLSKADYEKHKVYACEVTHQ GLSSPVTKSFNRGEC |
| Amino acid sequence for mAb2 Heavy Chain with N-terminal D10 (D10-HC) (SEQ ID NO: 16) | DDDDDDDDDD QVQLVQSGAEVKKPGSSVKVSCKASGYTFSSNVISWVRQA PGQGLEWMGGVIPIVDIANYAQRFKGRVTITADESTSTTY MELSSLRSEDTAVYYCASTLGLVLDAMDYWGQGTLVTVSS ASTKGPSVFPLAPCSRSTSESTAALGCLVKDYFPEPVTVS WNSGALTSGVHTFPAVLQSSGLYSLSSVVTVPSSSLGTKT YTCNVDHKPSNTKVDKRVESKYGPPCPPCPAPEFLGGPSV FLFPPKPKDTLMISRTPEVTCVVVDVSQEDPEVQFNWYVD GVEVHNAKTKPREEQFNSTYRVVSVLTVLHQDWLNGKEYK CKVSNKGLPSSIEKTISKAKGQPREPQVYTLPPSQEEMTK NQVSLTCLVKGFYPSDIAVEWESNGQPENNYKTTPPVLDS DGSFFLYSRLTVDKSRWQEGNVFSCSVMHEALHNHYTQKS LSLSLGK |

TABLE 11-continued

| Sequences | |
|---|---|
| Amino acid sequence for D10 (SEQ ID NO: 1) | DDDDDDDDDD |
| Amino acid sequence for mAb2 Heavy Chain with N-terminal D10 and C-terminal D10 (D10-HC-D10) (SEQ ID NO: 17) | DDDDDDDDDD QVQLVQSGAEVKKPGSSVKVSCKASGYTFSSNVISWVRQA PGQGLEWMGGVIPIVDIANYAQRFKGRVTITADESTSTTY MELSSLRSEDTAVYYCASTLGLVLDAMDYWGQGTLVTVSS ASTKGPSVFPLAPCSRSTSESTAALGCLVKDYFPEPVTVS WNSGALTSGVHTFPAVLQSSGLYSLSSVVTVPSSSLGTKT YTCNVDHKPSNTKVDKRVESKYGPPCPPCPAPEFLGGPSV FLFPPKPKDTLMISRTPEVTCVVVDVSQEDPEVQFNWYVD GVEVHNAKTKPREEQFNSTYRVVSVLTVLHQDWLNGKEYK CKVSNKGLPSSIEKTISKAKGQPREPQVYTLPPSQEEMTK NQVSLTCLVKGFYPSDIAVEWESNGQPENNYKTTPPVLDS DGSFFLYSRLTVDKSRWQEGNVFSCSVMHEALHNHYTQKS LSLSLGKDDDDDDDDDD |
| Amino acid sequence for mAb2 Light Chain with N-terminal D10 (D10-LC) (SEQ ID NO: 18) | DDDDDDDDDD ETVLTQSPGTLSLSPGERATLSCRASQSLGSSYLAWYQQK PGQAPRLLIYGASSRAPGIPDRFSGSGSGTDFTLTISRLE PEDFAVYYCQQYADSPITFGQGTRLEIKRTVAAPSVFIFP PSDEQLKSGTASVVCLLNNFYPREAKVQWKVDNALQSGNS QESVTEQDSKDSTYSLSSTLTLSKADYEKHKVYACEVTHQ GLSSPVTKSFNRGEC |
| Amino acid sequence for mAb2 Light Chain with C-terminal D10 (LC-D10) (SEQ ID NO: 19) | ETVLTQSPGTLSLSPGERATLSCRASQSLGSSYLAWYQQK PGQAPRLLIYGASSRAPGIPDRFSGSGSGTDFTLTISRLE PEDFAVYYCQQYADSPITFGQGTRLEIKRTVAAPSVFIFP PSDEQLKSGTASVVCLLNNFYPREAKVQWKVDNALQSGNS QESVTEQDSKDSTYSLSSTLTLSKADYEKHKVYACEVTHQ GLSSPVTKSFNRGECDDDDDDDDDD |
| Amino acid sequence for mAb2 Light Chain with N-terminal D10 and C-terminal D10 (D10-LC-D10) (SEQ ID NO: 20) | DDDDDDDDDD ETVLTQSPGTLSLSPGERATLSCRASQSLGSSYLAWYQQK PGQAPRLLIYGASSRAPGIPDRFSGSGSGTDFTLTISRLE PEDFAVYYCQQYADSPITFGQGTRLEIKRTVAAPSVFIFP PSDEQLKSGTASVVCLLNNFYPREAKVQWKVDNALQSGNS QESVTEQDSKDSTYSLSSTLTLSKADYEKHKVYACEVTHQ GLSSPVTKSFNRGECDDDDDDDDDD |
| Amino acid sequence for mAb2 Light Chain with 1x Linker and C-terminal D10 (LC-G4S-D10) (SEQ ID NO: 21) | ETVLTQSPGTLSLSPGERATLSCRASQSLGSSYLAWYQQK PGQAPRLLIYGASSRAPGIPDRFSGSGSGTDFTLTISRLE PEDFAVYYCQQYADSPITFGQGTRLEIKRTVAAPSVFIFP PSDEQLKSGTASVVCLLNNFYPREAKVQWKVDNALQSGNS QESVTEQDSKDSTYSLSSTLTLSKADYEKHKVYACEVTHQ GLSSPVTKSFNRGECGGGGSDDDDDDDDDD |
| Amino acid sequence for mAb2 Light Chain with 2x Linker and C-terminal D10 (LC-(G4S)2-D10) (SEQ ID NO: 22) | ETVLTQSPGTLSLSPGERATLSCRASQSLGSSYLAWYQQK PGQAPRLLIYGASSRAPGIPDRFSGSGSGTDFTLTISRLE PEDFAVYYCQQYADSPITFGQGTRLEIKRTVAAPSVFIFP PSDEQLKSGTASVVCLLNNFYPREAKVQWKVDNALQSGNS QESVTEQDSKDSTYSLSSTLTLSKADYEKHKVYACEVTHQ GLSSPVTKSFNRGECGGGGSGGGGSDDDDDDDDDD |
| Nucleic acid sequence for mAb2 Heavy Chain WT (WT HC) (SEQ ID NO: 23) | CAGGTGCAGCTGGTGCAGTCTGGGGCTGAGGTGAAGAA GCCTGGGTCCTCGGTGAAGGTCTCCTGCAAGGCTTCTGG ATACACCTTCAGTAGCAATGTTATCAGCTGGGTGCGCCA GGCCCCTGGACAAGGGCTCGAGTGGATGGGGGGGGTCA TCCCTATTGTTGATATTGCGAACTACGCACAGAGATTCAA GGGCAGAGTCACGATTACCGCGGACGAATCCACTAGTAC AACTTACATGGAGTTGAGCAGCCTGAGGTCTGAGGACAC GGCCGTGTATTACTGTGCGAGCACACTTGGTCTCGTCCT GGATGCTATGGACTACTGGGGTCAGGGTACGTTAGTGAC GGTCTCGAGTGCTTCCACCAAGGGCCCATCCGTCTTCCC CCTGGCGCCCTGCTCCAGGAGCACCTCCGAGAGCACAG CCGCCCTGGGCTGCCTGGTCAAGGACTACTTCCCCGAAC CGGTGACGGTGTCGTGGAACTCAGGCGCCCTGACCAGC GGCGTGCACACCTTCCCGGCTGTCCTACAGTCCTCAGGA CTCTACTCCCTCAGCAGCGTGGTGACCGTGCCCTCCAGC AGCTTGGGCACGAAGACCTACACCTGCAACGTAGATCAC AAGCCCAGCAACACCAAGGTCGACAAGAGAGTTGAGTCC AAATATGGTCCCCCATGCCCACCATGCCCAGCACCTGAG TTCCTGGGGGGACCATCAGTCTTCCTGTTCCCCCCAAAA CCCAAGGACACTCTCATGATCTCCCGGACCCCTGAGGTC ACGTGCGTGGTGGTGGACGTGAGCCAGGAAGACCCCGA GGTCCAGTTCAACTGGTACGTGGATGGCGTGGAGGTGCA TAATGCCAAGACAAAGCCGCGGGAGGAGCAGTTCAACAG CACGTACCGTGTGGTCAGCGTCCTCACCGTCCTGCACCA |

TABLE 11-continued

| Sequences | |
|---|---|
| Amino acid sequence for D10 (SEQ ID NO: 1) | DDDDDDDDDD |
| | GGACTGGCTGAACGGCAAGGAGTACAAGTGCAAGGTCTC<br>CAACAAAGGCCTCCCGTCCTCCATCGAGAAAACCATCTC<br>CAAAGCCAAAGGGCAGCCCCGAGAGCCACAGGTGTACA<br>CCCTGCCCCCATCCCAGGAGGAGATGACCAAGAACCAG<br>GTCAGCCTGACCTGCCTGGTCAAAGGCTTCTACCCCAGC<br>GACATCGCCGTGGAGTGGGAGAGCAATGGGCAGCCGGA<br>GAACAACTACAAGACCACGCCTCCCGTGCTGGACTCCGA<br>CGGCTCCTTCTTCCTCTACAGCAGGCTAACCGTGGACAA<br>GAGCAGGTGGCAGGAGGGGAATGTCTTCTCATGCTCCGT<br>GATGCATGAGGCTCTGCACAACCACTACACACAGAAGAG<br>CCTCTCCCTGTCTCTGGGGAAATGA |
| Nucleic acid sequence for mAb2 Heavy Chain with N-terminal D10 (D10-HC) (SEQ ID NO: 24) | GACGACGATGATGACGATGACGACGACGATCAGGTGCAG<br>CTGGTGCAGTCTGGGGCTGAGGTGAAGAAGCCTGGGTC<br>CTCGGTGAAGGTCTCCTGCAAGGCTTCTGGATACACCTT<br>CAGTAGCAATGTTATCAGCTGGGTGCGCCAGGCCCCTGG<br>ACAAGGGCTCGAGTGGATGGGGGGGGTCATCCCTATTGT<br>TGATATTGCGAACTACGCACAGAGATTCAAGGGCAGAGT<br>CACGATTACCGCGGACGAATCCACTAGTACAACTTACATG<br>GAGTTGAGCAGCCTGAGGTCTGAGGACACGGCCGTGTAT<br>TACTGTGCGAGCACACTTGGTCTCGTCCTGGATGCTATG<br>GACTACTGGGGTCAGGGTACGTTAGTGACGGTCTCGAGT<br>GCTTCCACCAAGGGCCCATCCGTCTTCCCCCTGGCGCCC<br>TGCTCCAGGAGCACCTCCGAGAGCACAGCCGCCCTGGG<br>CTGCCTGGTCAAGGACTACTTCCCCGAACCGGTGACGGT<br>GTCGTGGAACTCAGGCGCCCTGACCAGCGGCGTGCACA<br>CCTTCCCGGCTGTCCTACAGTCCTCAGGACTCTACTCCCT<br>CAGCAGCGTGGTGACCGTGCCCTCCAGCAGCTTGGGCA<br>CGAAGACCTACACCTGCAACGTAGATCACAAGCCCAGCA<br>ACACCAAGGTCGACAAGAGAGTTGAGTCCAAATATGGTC<br>CCCCATGCCCACCATGCCCAGCACCTGAGTTCCTGGGGG<br>GACCATCAGTCTTCCTGTTCCCCCCAAAACCCAAGGACA<br>CTCTCATGATCTCCCGGACCCCTGAGGTCACGTGCGTGG<br>TGGTGGACGTGAGCCAGGAAGACCCCGAGGTCCAGTTC<br>AACTGGTACGTGGATGGCGTGGAGGTGCATAATGCCAAG<br>ACAAAGCCGCGGGAGGAGCAGTTCAACAGCACGTACCGT<br>GTGGTCAGCGTCCTCACCGTCCTGCACCAGGACTGGCTG<br>AACGGCAAGGAGTACAAGTGCAAGGTCTCCAACAAAGGC<br>CTCCCGTCCTCCATCGAGAAAACCATCTCCAAAGCCAAA<br>GGGCAGCCCCGAGAGCCACAGGTGTACACCCTGCCCCC<br>ATCCCAGGAGGAGATGACCAAGAACCAGGTCAGCCTGAC<br>CTGCCTGGTCAAAGGCTTCTACCCCAGCGACATCGCCGT<br>GGAGTGGGAGAGCAATGGGCAGCCGGAGAACAACTACA<br>AGACCACGCCTCCCGTGCTGGACTCCGACGGCTCCTTCT<br>TCCTCTACAGCAGGCTAACCGTGGACAAGAGCAGGTGGC<br>AGGAGGGGAATGTCTTCTCATGCTCCGTGATGCATGAGG<br>CTCTGCACAACCACTACACACAGAAGAGCCTCTCCCTGT<br>CTCTGGGGAAATGA |
| Nucleic acid sequence for mAb2 Heavy Chain with C-terminal D10 (HC-D10) (SEQ ID NO: 25) | CAGGTGCAGCTGGTGCAGTCTGGGGCTGAGGTGAAGAA<br>GCCTGGGTCCTCGGTGAAGGTCTCCTGCAAGGCTTCTGG<br>ATACACCTTCAGTAGCAATGTTATCAGCTGGGTGCGCCA<br>GGCCCCTGGACAAGGGCTCGAGTGGATGGGGGGGGTCA<br>TCCCTATTGTTGATATTGCGAACTACGCACAGAGATTCAA<br>GGGCAGAGTCACGATTACCGCGGACGAATCCACTAGTAC<br>AACTTACATGGAGTTGAGCAGCCTGAGGTCTGAGGACAC<br>GGCCGTGTATTACTGTGCGAGCACACTTGGTCTCGTCCT<br>GGATGCTATGGACTACTGGGGTCAGGGTACGTTAGTGAC<br>GGTCTCGAGTGCTTCCACCAAGGGCCCATCCGTCTTCCC<br>CCTGGCGCCCTGCTCCAGGAGCACCTCCGAGAGCACAG<br>CCGCCCTGGGCTGCCTGGTCAAGGACTACTTCCCCGAAC<br>CGGTGACGGTGTCGTGGAACTCAGGCGCCCTGACCAGC<br>GGCGTGCACACCTTCCCGGCTGTCCTACAGTCCTCAGGA<br>CTCTACTCCCTCAGCAGCGTGGTGACCGTGCCCTCCAGC<br>AGCTTGGGCACGAAGACCTACACCTGCAACGTAGATCAC<br>AAGCCCAGCAACACCAAGGTCGACAAGAGAGTTGAGTCC<br>AAATATGGTCCCCCATGCCCACCATGCCCAGCACCTGAG<br>TTCCTGGGGGGACCATCAGTCTTCCTGTTCCCCCCAAAA<br>CCCAAGGACACTCTCATGATCTCCCGGACCCCTGAGGTC<br>ACGTGCGTGGTGGTGGACGTGAGCCAGGAAGACCCCGA<br>GGTCCAGTTCAACTGGTACGTGGATGGCGTGGAGGTGCA<br>TAATGCCAAGACAAAGCCGCGGGAGGAGCAGTTCAACAG<br>CACGTACCGTGTGGTCAGCGTCCTCACCGTCCTGCACCA<br>GGACTGGCTGAACGGCAAGGAGTACAAGTGCAAGGTCTC<br>CAACAAAGGCCTCCCGTCCTCCATCGAGAAAACCATCTC |

TABLE 11-continued

| Sequences | |
|---|---|
| Amino acid sequence for D10 (SEQ ID NO: 1) | DDDDDDDDDD |
| | CAAAGCCAAAGGGCAGCCCCGAGAGCCACAGGTGTACA<br>CCCTGCCCCCATCCCAGGAGGAGATGACCAAGAACCAG<br>GTCAGCCTGACCTGCCTGGTCAAAGGCTTCTACCCCAGC<br>GACATCGCCGTGGAGTGGGAGAGCAATGGGCAGCCGGA<br>GAACAACTACAAGACCACGCCTCCCGTGCTGGACTCCGA<br>CGGCTCCTTCTTCCTCTACAGCAGGCTAACCGTGGACAA<br>GAGCAGGTGGCAGGAGGGGAATGTCTTCTCATGCTCCGT<br>GATGCATGAGGCTCTGCACAACCACTACACACAGAAGAG<br>CCTCTCCCTGTCTCTGGGGAAAGACGACGATGATGACGA<br>TGACGACGACGATTGA |
| Nucleic acid sequence for mAb2 Heavy Chain with N-terminal D10 and C-termina (D10-HC-D10) (SEQ ID NO: 26) | GACGACGATGATGACGATGACGACGACGATCAGGTGCAG<br>CTGGTGCAGTCTGGGGCTGAGGTGAAGAAGCCTGGGTC<br>CTCGGTGAAGGTCTCCTGCAAGGCTTCTGGATACACCTT<br>CAGTAGCAATGTTATCAGCTGGGTGCGCCAGGCCCCTGG<br>ACAAGGGCTCGAGTGGATGGGGGGGTCATCCCTATTGT<br>TGATATTGCGAACTACGCACAGAGATTCAAGGGCAGAGT<br>CACGATTACCGCGGACGAATCCACTAGTACAACTTACATG<br>GAGTTGAGCAGCCTGAGGTCTGAGGACACGGCCGTGTAT<br>TACTGTGCGAGCACACTTGGTCTCGTCCTGGATGCTATG<br>GACTACTGGGGTCAGGGTACGTTAGTGACGGTCTCGAGT<br>GCTTCCACCAAGGGCCCATCCGTCTTCCCCCTGGCGCCC<br>TGCTCCAGGAGCACCTCCGAGAGCACAGCCGCCCTGGG<br>CTGCCTGGTCAAGGACTACTTCCCCGAACCGGTGACGGT<br>GTCGTGGAACTCAGGCGCCCTGACCAGCGGCGTGCACA<br>CCTTCCCGGCTGTCCTACAGTCCTCAGGACTCTACTCCCT<br>CAGCAGCGTGGTGACCGTGCCCTCCAGCAGCTTGGGCA<br>CGAAGACCTACACCTGCAACGTAGATCACAAGCCCAGCA<br>ACACCAAGGTCGACAAGAGAGTTGAGTCCAAATATGGTC<br>CCCCATGCCCACCATGCCCAGCACCTGAGTTCCTGGGGG<br>GACCATCAGTCTTCCTGTTCCCCCCAAAACCCAAGGACA<br>CTCTCATGATCTCCCGGACCCCTGAGGTCACGTGCGTGG<br>TGGTGGACGTGAGCCAGGAAGACCCCGAGGTCCAGTTC<br>AACTGGTACGTGGATGGCGTGGAGGTGCATAATGCCAAG<br>ACAAAGCCGCGGGAGGAGCAGTTCAACAGCACGTACCGT<br>GTGGTCAGCGTCCTCACCGTCCTGCACCAGGACTGGCTG<br>AACGGCAAGGAGTACAAGTGCAAGGTCTCCAACAAAGGC<br>CTCCCGTCCTCCATCGAGAAAACCATCTCCAAAGCCAAA<br>GGGCAGCCCCGAGAGCCACAGGTGTACACCCTGCCCCC<br>ATCCCAGGAGGAGATGACCAAGAACCAGGTCAGCCTGAC<br>CTGCCTGGTCAAAGGCTTCTACCCCAGCGACATCGCCGT<br>GGAGTGGGAGAGCAATGGGCAGCCGGAGAACAACTACA<br>AGACCACGCCTCCCGTGCTGGACTCCGACGGCTCCTTCT<br>TCCTCTACAGCAGGCTAACCGTGGACAAGAGCAGGTGGC<br>AGGAGGGGAATGTCTTCTCATGCTCCGTGATGCATGAGG<br>CTCTGCACAACCACTACACACAGAAGAGCCTCTCCCTGT<br>CTCTGGGGAAAGACGACGATGATGACGATGACGACGACG<br>ATTGA |
| Nucleic acid sequence for mAb2 Light Chain WT (WT LC) (SEQ ID NO: 27) | GAAACGGTACTCACGCAGTCTCCAGGTACCCTGTCTTTGT<br>CTCCAGGGGAAAGAGCCACCCTCTCCTGCAGGGCCAGT<br>CAGAGTCTTGGCAGCAGCTACTTAGCCTGGTATCAGCAG<br>AAACCTGGTCAGGCTCCCAGGCTCCTCATCTATGGTGCA<br>TCCAGCAGGGCACCTGGCATCCCAGACAGGTTCAGTGGC<br>AGTGGGTCTGGTACCGACTTCACTCTCACCATCAGCCGA<br>CTGGAGCCTGAAGATTTTGCAGTTTATTACTGTCAGCAGT<br>ATGCTGACTCACCGATCACCTTCGGCCAAGGGACACGAC<br>TGGAGATTAAACGTACGGTGGCTGCACCATCTGTCTTCAT<br>CTTCCCGCCATCTGATGAGCAGTTGAAATCTGGAACTGC<br>CTCTGTTGTGTGCCTGCTGAATAACTTCTATCCCAGAGAG<br>GCCAAAGTACAGTGGAAGGTGGATAACGCCCTCCAATCG<br>GGTAACTCCCAGGAGAGTGTCACAGAGCAGGACAGCAAG<br>GACAGCACCTACAGCCTCAGCAGCACCCTGACGCTGAGC<br>AAAGCAGACTACGAGAAACACAAAGTCTACGCCTGCGAA<br>GTCACCCATCAGGGCCTGAGCTCGCCCGTCACAAAGAGC<br>TTCAACAGGGGAGAGTGTTAG |
| Nucleic acid sequence for mAb2 Light Chain with N-terminal D10 (D10-LC) (SEQ ID NO: 28) | GACGACGATGATGACGATGACGACGACGATGAAACGGTA<br>CTCACGCAGTCTCCAGGTACCCTGTCTTTGTCTCCAGGG<br>GAAAGAGCCACCCTCTCCTGCAGGGCCAGTCAGAGTCTT<br>GGCAGCAGCTACTTAGCCTGGTATCAGCAGAAACCTGGT<br>CAGGCTCCCAGGCTCCTCATCTATGGTGCATCCAGCAGG<br>GCACCTGGCATCCCAGACAGGTTCAGTGGCAGTGGGTCT<br>GGTACCGACTTCACTCTCACCATCAGCCGACTGGAGCCT<br>GAAGATTTTGCAGTTTATTACTGTCAGCAGTATGCTGACT |

TABLE 11-continued

Sequences

| | |
|---|---|
| Amino acid sequence for D10 (SEQ ID NO: 1) | DDDDDDDDDD |
| | CACCGATCACCTTCGGCCAAGGGACACGACTGGAGATTA<br>AACGTACGGTGGCTGCACCATCTGTCTTCATCTTCCCGC<br>CATCTGATGAGCAGTTGAAATCTGGAACTGCCTCTGTTGT<br>GTGCCTGCTGAATAACTTCTATCCCAGAGAGGCCAAAGTA<br>CAGTGGAAGGTGGATAACGCCCTCCAATCGGGTAACTCC<br>CAGGAGAGTGTCACAGAGCAGGACAGCAAGGACAGCAC<br>CTACAGCCTCAGCAGCACCCTGACGCTGAGCAAAGCAGA<br>CTACGAGAAACACAAAGTCTACGCCTGCGAAGTCACCCA<br>TCAGGGCCTGAGCTCGCCCGTCACAAAGAGCTTCAACAG<br>GGGAGAGTGTTAG |
| Nucleic acid sequence for mAb2 Light Chain with C-terminal D10 (LC-D10) (SEQ ID NO: 29) | GAAACGGTACTCACGCAGTCTCCAGGTACCCTGTCTTTGT<br>CTCCAGGGGAAAGAGCCACCCTCTCCTGCAGGGCCAGT<br>CAGAGTCTTGGCAGCAGCTACTTAGCCTGGTATCAGCAG<br>AAACCTGGTCAGGCTCCCAGGCTCCTCATCTATGGTGCA<br>TCCAGCAGGGCACCTGGCATCCCAGACAGGTTCAGTGGC<br>AGTGGGTCTGGTACCGACTTCACTCTCACCATCAGCCGA<br>CTGGAGCCTGAAGATTTTGCAGTTTATTACTGTCAGCAGT<br>ATGCTGACTCACCGATCACCTTCGGCCAAGGGACACGAC<br>TGGAGATTAAACGTACGGTGGCTGCACCATCTGTCTTCAT<br>CTTCCCGCCATCTGATGAGCAGTTGAAATCTGGAACTGC<br>CTCTGTTGTGTGCCTGCTGAATAACTTCTATCCCAGAGAG<br>GCCAAAGTACAGTGGAAGGTGGATAACGCCCTCCAATCG<br>GGTAACTCCCAGGAGAGTGTCACAGAGCAGGACAGCAAG<br>GACAGCACCTACAGCCTCAGCAGCACCCTGACGCTGAGC<br>AAAGCAGACTACGAGAAACACAAAGTCTACGCCTGCGAA<br>GTCACCCATCAGGGCCTGAGCTCGCCCGTCACAAAGAGC<br>TTCAACAGGGGAGAGTGTGACGACGATGATGACGATGAC<br>GACGACGATTAG |
| Nucleic acid sequence for mAb2 Light Chain with N-terminal D10 and C-terminal D10 (D10-LC-D10) (SEQ ID NO: 30) | GACGACGATGATGACGATGACGACGACGATGAAACGGTA<br>CTCACGCAGTCTCCAGGTACCCTGTCTTTGTCTCCAGGG<br>GAAAGAGCCACCCTCTCCTGCAGGGCCAGTCAGAGTCTT<br>GGCAGCAGCTACTTAGCCTGGTATCAGCAGAAACCTGGT<br>CAGGCTCCCAGGCTCCTCATCTATGGTGCATCCAGCAGG<br>GCACCTGGCATCCCAGACAGGTTCAGTGGCAGTGGGTCT<br>GGTACCGACTTCACTCTCACCATCAGCCGACTGGAGCCT<br>GAAGATTTTGCAGTTTATTACTGTCAGCAGTATGCTGACT<br>CACCGATCACCTTCGGCCAAGGGACACGACTGGAGATTA<br>AACGTACGGTGGCTGCACCATCTGTCTTCATCTTCCCGC<br>CATCTGATGAGCAGTTGAAATCTGGAACTGCCTCTGTTGT<br>GTGCCTGCTGAATAACTTCTATCCCAGAGAGGCCAAAGTA<br>CAGTGGAAGGTGGATAACGCCCTCCAATCGGGTAACTCC<br>CAGGAGAGTGTCACAGAGCAGGACAGCAAGGACAGCAC<br>CTACAGCCTCAGCAGCACCCTGACGCTGAGCAAAGCAGA<br>CTACGAGAAACACAAAGTCTACGCCTGCGAAGTCACCCA<br>TCAGGGCCTGAGCTCGCCCGTCACAAAGAGCTTCAACAG<br>GGGAGAGTGTGACGACGATGATGACGATGACGACGACG<br>ATTAG |
| Nucleic acid sequence for mAb2 Light Chain with 1x Linker and C-terminal D10 (LC-G4S-D10) (SEQ ID NO: 31) | GAAACGGTACTCACGCAGTCTCCAGGTACCCTGTCTTTGT<br>CTCCAGGGGAAAGAGCCACCCTCTCCTGCAGGGCCAGT<br>CAGAGTCTTGGCAGCAGCTACTTAGCCTGGTATCAGCAG<br>AAACCTGGTCAGGCTCCCAGGCTCCTCATCTATGGTGCA<br>TCCAGCAGGGCACCTGGCATCCCAGACAGGTTCAGTGGC<br>AGTGGGTCTGGTACCGACTTCACTCTCACCATCAGCCGA<br>CTGGAGCCTGAAGATTTTGCAGTTTATTACTGTCAGCAGT<br>ATGCTGACTCACCGATCACCTTCGGCCAAGGGACACGAC<br>TGGAGATTAAACGTACGGTGGCTGCACCATCTGTCTTCAT<br>CTTCCCGCCATCTGATGAGCAGTTGAAATCTGGAACTGC<br>CTCTGTTGTGTGCCTGCTGAATAACTTCTATCCCAGAGAG<br>GCCAAAGTACAGTGGAAGGTGGATAACGCCCTCCAATCG<br>GGTAACTCCCAGGAGAGTGTCACAGAGCAGGACAGCAAG<br>GACAGCACCTACAGCCTCAGCAGCACCCTGACGCTGAGC<br>AAAGCAGACTACGAGAAACACAAAGTCTACGCCTGCGAA<br>GTCACCCATCAGGGCCTGAGCTCGCCCGTCACAAAGAGC<br>TTCAACAGGGGAGAGTGTGGCGGAGGCGGCAGCGACGA<br>CGATGATGACGATGACGACGACGATTAG |
| Nucleic acid sequence for mAb2 Light Chain with 2x Linker and C-terminal D10 (LC-(G4S)2-D10) (SEQ ID NO: 32) | GAAACGGTACTCACGCAGTCTCCAGGTACCCTGTCTTTGT<br>CTCCAGGGGAAAGAGCCACCCTCTCCTGCAGGGCCAGT<br>CAGAGTCTTGGCAGCAGCTACTTAGCCTGGTATCAGCAG<br>AAACCTGGTCAGGCTCCCAGGCTCCTCATCTATGGTGCA<br>TCCAGCAGGGCACCTGGCATCCCAGACAGGTTCAGTGGC<br>AGTGGGTCTGGTACCGACTTCACTCTCACCATCAGCCGA |

TABLE 11-continued

Sequences

Amino acid sequence for
D10 (SEQ ID NO: 1)          DDDDDDDDDD

CTGGAGCCTGAAGATTTTGCAGTTTATTACTGTCAGCAGT
                            ATGCTGACTCACCGATCACCTTCGGCCAAGGGACACGAC
                            TGGAGATTAAACGTACGGTGGCTGCACCATCTGTCTTCAT
                            CTTCCCGCCATCTGATGAGCAGTTGAAATCTGGAACTGC
                            CTCTGTTGTGTGCCTGCTGAATAACTTCTATCCCAGAGAG
                            GCCAAAGTACAGTGGAAGGTGGATAACGCCCTCCAATCG
                            GGTAACTCCCAGGAGAGTGTCACAGAGCAGGACAGCAAG
                            GACAGCACCTACAGCCTCAGCAGCACCCTGACGCTGAGC
                            AAAGCAGACTACGAGAAACACAAAGTCTACGCCTGCGAA
                            GTCACCCATCAGGGCCTGAGCTCGCCCGTCACAAAGAGC
                            TTCAACAGGGGAGAGTGTGGCGGAGGCGGCAGCGGCGG
                            AGGCGGCAGCGACGACGATGATGACGATGACGACGACG
                            ATTAG mAb2 HCDR1                  SNVIS
(SEQ ID NO: 33)

mAb2 HCDR2                  GVIPIVDIANYAQRFKG
(SEQ ID NO: 34)

mAb2 HCDR3                  TLGLVLDAMDY
(SEQ ID NO: 35)

mAb2 LCDR1                  RASQSLGSSYLA
(SEQ ID NO: 36)

mAb2 LCDR2                  GASSRAP
(SEQ ID NO: 37)

mAb2 LCDR3                  QQYADSPIT
(SEQ ID NO: 38)

mAb2 HCVD                   QVQLVQSGAEVKKPGSSVKVSCKASGYTFSSNVISWVRQA
(SEQ ID NO: 39)             PGQGLEWMGGVIPIVDIANYAQRFKGRVTITADESTSTTY
                            MELSSLRSEDTAVYYCASTLGLVLDAMDYWGQGTLVTVSS mAb2 LCVD                   ETVLTQSPGTLSLSPGERATLSCRASQSLGSSYLAWYQQK
(SEQ ID NO: 40)             PGQAPRLLIYGASSRAPGIPDRFSGSGSGTDFTLTISRLE
                            PEDFAVYYCQQYADSPITFGQGTRLEIK

What is claimed is:

1. A method for treating a bone condition that benefits from inhibition of TGFβ, comprising administering to a human subject in need thereof an effective amount of an anti-TGFβ antibody or an antigen-binding fragment thereof comprising a heavy chain and a light chain, wherein (i) the heavy chain is a fusion polypeptide comprising a poly-aspartic acid (poly-D) peptide at either or both of its N- and C-termini; and/or (ii) the light chain is a fusion polypeptide comprising a poly-D peptide at its C-terminus, wherein the poly-D peptide(s) each comprise SEQ ID NO: 1; and wherein the antibody comprises the heavy chain complementarity-determining regions (CDRs) 1-3 in SEQ ID NO: 13 and the light chain CDR1-3 in SEQ ID NO: 15, or the heavy chain CDR1-3 in SEQ ID NO: 2 and the light chain CDR1-3 in SEQ ID NO: 6.

2. The method of claim 1, comprising (i) a poly-D peptide integral with the N-terminus of the heavy chain, (ii) a poly-D peptide integral with the C-terminus of the heavy chain, or (iii) both (i) and (ii).

3. The method of claim 1, comprising a poly-D peptide integral with the C-terminus of the light chain.

4. The method of claim 1, wherein the poly-D peptide(s) are fused to the heavy or light chain via a peptide linker.

5. The method of claim 1, wherein the antibody is an IgG$_1$ or IgG$_4$.

6. The method of claim 5, wherein the antibody comprises a human IgG$_4$ constant region having a proline at position 228 (Eu numbering).

7. The method of claim 1, wherein the antibody comprises a heavy chain variable domain (V$_H$) amino acid sequence corresponding to residues 1-120 of SED ID NO: 13 and a light chain variable domain (V$_L$) amino acid sequence corresponding to residues 1-108 of SEQ ID NO:15.

8. The method of claim 1, wherein the heavy chain comprises SEQ ID NO: 13 and the light chain comprises SEQ ID NO: 15.

9. The method of claim 1, wherein the heavy chain comprises SEQ ID NO: 13, 14, 16, or 17, and the light chain comprises SEQ ID NO: 15, 19, 21, or 22.

10. The method of claim 1, wherein the antibody is an IgG$_4$ antibody whose heavy chain comprises SEQ ID NO: 14 and whose light chain comprises SEQ ID NO: 15.

11. The method of claim 1, wherein the antibody is an IgG$_4$ antibody whose heavy chain comprises SEQ ID NO: 17 and whose light chain comprises SEQ ID NO: 15.

12. The method of claim 1, wherein the heavy chain comprises a variable domain in SEQ ID NO: 2 and the light chain comprises a variable domain in SEQ ID NO: 6.

13. The method of claim 1, wherein the heavy chain comprises SEQ ID NO: 2, 3, 4, or 5, and the light chain comprises SEQ ID NO: 6, 8, 11, or 12.

* * * * *